(12) United States Patent
Galan Garcia et al.

(10) Patent No.: US 12,108,664 B2
(45) Date of Patent: Oct. 1, 2024

(54) COMPOUND AND ORGANIC SEMICONDUCTING LAYER, ORGANIC ELECTRONIC DEVICE, DISPLAY DEVICE AND LIGHTING DEVICE COMPRISING THE SAME

(71) Applicant: Novaled GmbH, Dresden (DE)

(72) Inventors: Elena Galan Garcia, Dresden (DE); Benjamin Schulze, Dresden (DE); Jens Wutke, Dresden (DE); Horst Hartmann, Dresden (DE)

(73) Assignee: Novaled GmbH, Dresden (DE)

( * ) Notice: Subject to any disclaimer, the term of this patent is extended or adjusted under 35 U.S.C. 154(b) by 299 days.

(21) Appl. No.: 17/259,762

(22) PCT Filed: Jul. 16, 2019

(86) PCT No.: PCT/EP2019/069132
§ 371 (c)(1),
(2) Date: Jan. 12, 2021

(87) PCT Pub. No.: WO2020/016233
PCT Pub. Date: Jan. 23, 2020

(65) Prior Publication Data
US 2021/0367157 A1    Nov. 25, 2021

(30) Foreign Application Priority Data
Jul. 18, 2018  (EP) .................... 18184297.2

(51) Int. Cl.
*H10K 85/60*       (2023.01)
*C07D 221/18*      (2006.01)
(Continued)

(52) U.S. Cl.
CPC ......... *H10K 85/654* (2023.02); *C07D 221/18* (2013.01); *C07D 251/24* (2013.01);
(Continued)

(58) Field of Classification Search
CPC .. C07D 221/18; C07D 251/24; C07D 405/04; H10K 85/615; H10K 85/654; H10K 85/6572; H10K 85/6574
See application file for complete search history.

(56) References Cited

U.S. PATENT DOCUMENTS 8,940,412 B2 * 1/2015 Takashima ............. C09K 11/06
                                                     548/440
8,993,123 B2   3/2015 Buesing et al.
(Continued)

FOREIGN PATENT DOCUMENTS

CN    101939279 A    1/2011
CN    104904032 A    9/2015
(Continued)

OTHER PUBLICATIONS

Choudhury et al., J. Org. Chem. 2007, 72, 9732-9735.*
(Continued)

*Primary Examiner* — Vu A Nguyen
(74) *Attorney, Agent, or Firm* — Eversheds Sutherland (US) LLP

(57) ABSTRACT

The present invention relates to an organic compound of formula (1), suitable for use as a layer material for electronic devices, and it relates to an organic semiconductor layer comprising at least one compound thereof, as well as to an organic electronic device comprising at least one organic (Continued)

semiconductor layer, and a method of manufacturing the same.

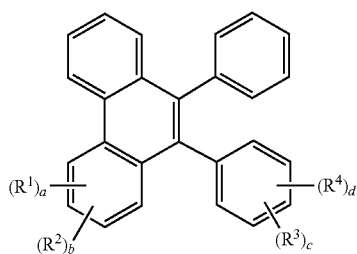

(1)

28 Claims, 2 Drawing Sheets

(51) Int. Cl.
    *C07D 251/24*     (2006.01)
    *C07D 405/04*     (2006.01)
    *H10K 50/16*     (2023.01)
(52) U.S. Cl.
    CPC ......... *C07D 405/04* (2013.01); *H10K 85/615* (2023.02); *H10K 85/6572* (2023.02); *H10K 85/6574* (2023.02); *H10K 50/16* (2023.02)

(56) References Cited

U.S. PATENT DOCUMENTS

| | | | |
|---|---|---|---|
| 9,296,944 B2 * | 3/2016 | Ise | ................ H10K 85/626 |
| 11,312,691 B2 * | 4/2022 | Jung | ................ C09K 11/00 |
| 2006/0024525 A1 | 2/2006 | Jeong | |
| 2012/0319568 A1 | 12/2012 | Ise | |

FOREIGN PATENT DOCUMENTS

| | | | | |
|---|---|---|---|---|
| CN | 107978683 A | | 5/2018 | |
| CN | 108409666 A | * | 8/2018 | |
| EP | 1253179 A1 | | 10/2002 | |
| JP | 2017154988 A | * | 9/2017 | |
| KR | 2015075169 A | * | 7/2015 | ........... C07D 401/10 |
| KR | 2015076503 A | * | 7/2015 | ........... C07D 239/70 |
| KR | 20160082067 A | * | 7/2016 | ........... C07D 403/04 |
| KR | 2018048968 A | | 5/2018 | |
| TW | 201134786 A | | 10/2011 | |
| WO | WO-2012133042 A1 | * | 10/2012 | ........... C07C 255/50 |
| WO | WO-2017036573 A1 | * | 3/2017 | ........... C07B 59/001 |

OTHER PUBLICATIONS

Feng et al., Engew. Chem. Int. Ed. 2007, 46, 3033-3036.*
Gong et al., J. Mater. Chem. C, 2014, 2, 7001-7012.*
Komatsu et al., Bull. Chem. Soc. Jpn., 55, 2470-2479 (1982).*
Navale et al., Org. Lett. 2011, 13(7), 1634-1637.*
Machine-generated English-language translation of WO-2012133042-A1.*
Ma et al., Synlett 2015, 26, 1991-1996.*
G. Dyker and A. Kellner, Journal of Organometallic Chemistry 555 (1998) 141-144.*
Communication pursuant to Article 94(3) EPC issued in European application No. 18184297.2, dated Feb. 10, 2023, 5 pp.
PCT International Search Report and Written Opinion for PCT Application No. PCT/EP2019/069132 mailed Oct. 2, 2019 (9 pages).
Aldred et al., "Fluorescence Quenching and Enhancement of Vitrifiable Oligofluorenes end-Capped with Tetraphenylethene," J. Mater. Chem., 2012, 22:7515-7528.
Gong et al., "Tetraphenylethene-Decorated Carbazoles: Synthesis, Aggregation-Induced Emission, Photo-Oxidatin and Electroluminescence," Journal of Materials Chemistry C, 2013 (13 pages).
Communication pursuant to Article 94(3) EPC issued in European application No. 19739616.1, dated Apr. 25, 2023, 7 pages.
Notification of First Office Action issued in Chinese application No. 201980047472.3, dated May 6, 2023, 15 pages.
Notification of Second Office Action issued in Chinese application No. 201980047472.3, dated Oct. 13, 2023 (9 pages).
Decision of Rejection issued in China application No. 201980047472.3, dated Jun. 3, 2024 (17 pages).
Request for the Submission of an Opinion issued in Korea application No. 10-2021-7004507, dated Jun. 22, 2024 (22 pages).

* cited by examiner

COMPOUND AND ORGANIC SEMICONDUCTING LAYER, ORGANIC ELECTRONIC DEVICE, DISPLAY DEVICE AND LIGHTING DEVICE COMPRISING THE SAME

CROSS REFERENCE TO RELATED APPLICATIONS

This application is a U.S. national phase application of international application no. PCT/EP2019/069132, filed Jul. 16, 2019, which claims priority to European Application No. 18184297.2, filed Jul. 18, 2018. The content of these applications is incorporated herein by reference.

TECHNICAL FIELD

The present invention relates to an organic compound of formula 1, suitable for use as a layer material for electronic devices, and it relates to an organic semiconductor layer comprising at least one compound thereof, as well as to an organic electronic device comprising at least one organic semiconductor layer, and a method of manufacturing the same.

BACKGROUND ART

Organic electronic devices, such as organic light-emitting diodes OLEDs, which are self-emitting devices, have a wide viewing angle, excellent contrast, quick response, high brightness, excellent operating voltage characteristics, and color reproduction. A typical OLED comprises an anode, a hole transport layer HTL, an emission layer EML, an electron transport layer ETL, and a cathode, which are sequentially stacked on a substrate. In this regard, the HTL, the EML, and the ETL are thin films formed from organic compounds.

When a voltage is applied to the anode and the cathode, holes injected from the anode move to the EML, via the HTL, and electrons injected from the cathode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency and/or a long lifetime.

Performance of an organic light emitting diode may be affected by characteristics of the organic semiconductor layer, and among them, may be affected by characteristics of an organic material of the organic semiconductor layer.

There is a need for organic compounds having improved melting point, improved glass transition temperature ($T_g$) and a rate onset temperature ($T_{RO}$) in a range suitable for mass production. Additionally, there is a need for improved performance of organic electronic devices. In particular, there is a need for organic electronic devices having a high efficiency and long lifetime at lower operating voltages. Thereby the power consumption may be decreased and battery life improved, for example of mobile electronic devices.

DISCLOSURE

An aspect of the present invention provides a compound of formula 1:

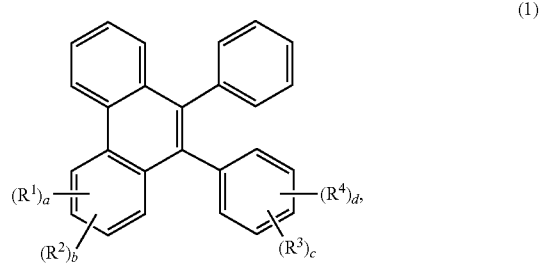

(1)

wherein
$R^1, R^2, R^3$ and $R^4$ are independently selected from hydrogen, substituted or unsubstituted $C_6$ to $C_{38}$ aryl, substituted or unsubstituted $C_3$ to $C_{36}$ heteroaryl or $C_1$ to $C_{16}$ alkyl group, —PO(R')$_2$, D, F, CN, or formula 2;

(2)

wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

R' is independently selected from alkyl, aryl or heteroaryl;
a, b, c, d and e are independently 0, 1 or 2, wherein at least one of a, b, c or d is 1 or 2;
wherein
at least one of $R^1$, $R^2$, $R^3$ or $R^4$ is formula 2;
$Ar^1$ is selected from substituted or unsubstituted $C_6$ to $C_{38}$ arylene, substituted or unsubstituted $C_3$ to $C_{36}$ heteroarylene or $C_1$ to $C_{16}$ alkylene group, wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_{36}$ heteroaryl or $C_1$ to $C_{16}$ alkyl group, wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

wherein
$Ar^1$ does not contain one or more CN substituents when $Ar^2$ is substituted or unsubstituted $C_6$ to $C_{38}$ aryl;

wherein
the following compound 3 is excluded:

(3)

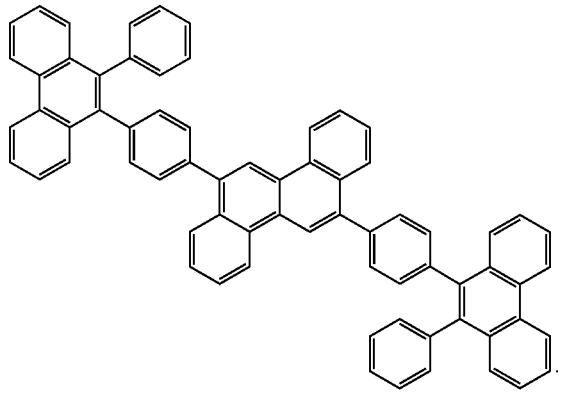

According to another embodiment of the compound of formula 1:

(1)

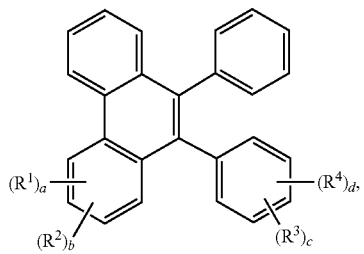

wherein
R$^1$, R$^2$, R$^3$ and R$^4$ are independently selected from hydrogen, substituted or unsubstituted C$_6$ to C$_{38}$ aryl, substituted or unsubstituted C$_3$ to C$_{36}$ heteroaryl or C$_1$ to C$_{16}$ alkyl group, —PO(R')$_2$, D, F, CN, or formula 2;

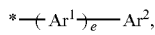 (2)

wherein
the substituents are selected from C$_6$ to C$_{18}$ aryl, C$_3$ to C$_{25}$ heteroaryl, —PO(R')$_2$, D, F or CN, C$_1$ to C$_{16}$ alkyl, partially or perfluorinated C$_1$ to C$_{16}$ alkyl, partially or perdeuterated C$_1$ to C$_{16}$ alkyl, C$_1$ to C$_{16}$ alkoxy, partially or perfluorinated C$_1$ to C$_{16}$ alkoxy, partially or perdeuterated C$_1$ to C$_{16}$ alkoxy;

R' is independently selected from alkyl, aryl or heteroaryl;
a, b, c, d and e are independently 0, 1 or 2, wherein at least one of a, b, c or d is 1 or 2;
wherein
at least one of R$^1$, R$^2$, R$^3$ or R$^4$ is formula 2;
Ar$^1$ is selected from substituted or unsubstituted C$_6$ to C$_{38}$ arylene, substituted or unsubstituted C$_3$ to C$_{36}$ heteroarylene or C$_1$ to C$_{16}$ alkylene group, wherein
the substituents are selected from C$_6$ to C$_{18}$ aryl, C$_3$ to C$_{25}$ heteroaryl, —PO(R')$_2$, D, F or CN, C$_1$ to C$_{16}$ alkyl, partially or perfluorinated C$_1$ to C$_{16}$ alkyl, partially or perdeuterated C$_1$ to C$_{16}$ alkyl, C$_1$ to C$_{16}$ alkoxy, partially or perfluorinated C$_1$ to C$_{16}$ alkoxy, partially or perdeuterated C$_1$ to C$_{16}$ alkoxy;

Ar$^2$ is selected from substituted or unsubstituted C$_6$ to C$_{38}$ aryl, substituted or unsubstituted C$_3$ to C$_{36}$ heteroaryl or C$_1$ to C$_{16}$ alkyl group, wherein
the substituents are selected from C$_6$ to C$_{18}$ aryl, C$_3$ to C$_{25}$ heteroaryl, —PO(R')$_2$, D, F or CN, C$_1$ to C$_{16}$ alkyl, partially or perfluorinated C$_1$ to C$_{16}$ alkyl, partially or perdeuterated C$_1$ to C$_{16}$ alkyl, C$_1$ to C$_{16}$ alkoxy, partially or perfluorinated C$_1$ to C$_{16}$ alkoxy, partially or perdeuterated C$_1$ to C$_{16}$ alkoxy;
wherein
Ar$^1$ does not contain one or more CN substituents when Ar$^2$ is substituted or unsubstituted C$_6$ to C$_{38}$ aryl;
wherein
the following compounds 3, 4, 5, 6 and 7 are excluded:

(3)

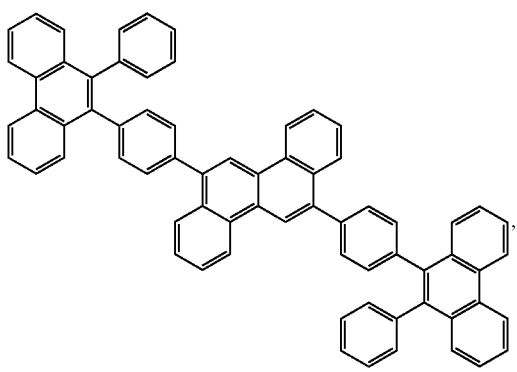

(4)

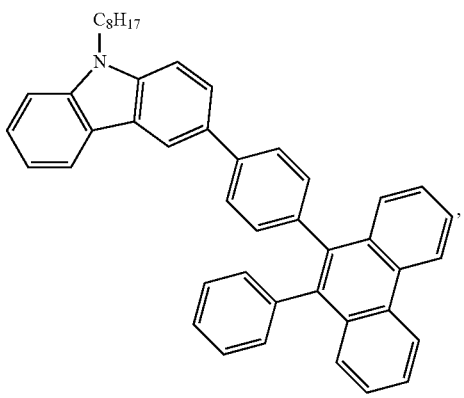

-continued

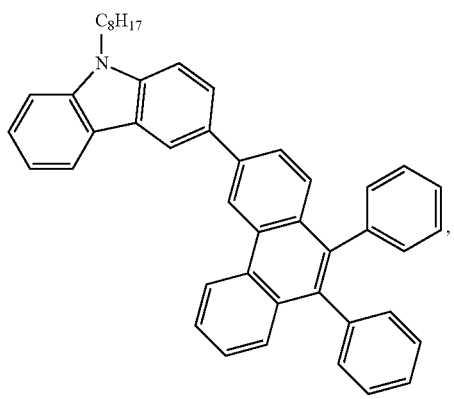

(5)

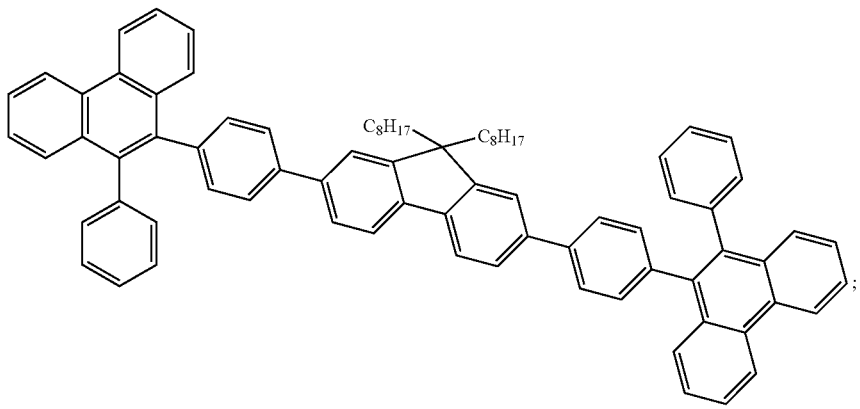

(6)

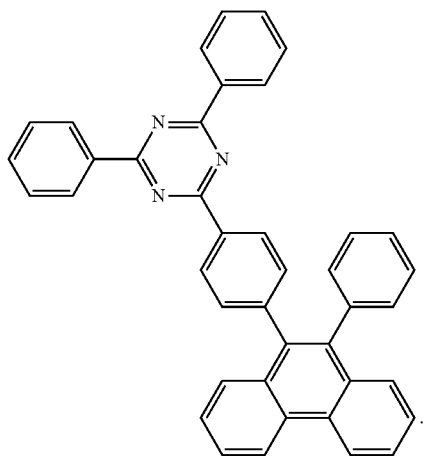

(7)

According to another embodiment according to the compound of formula 1:

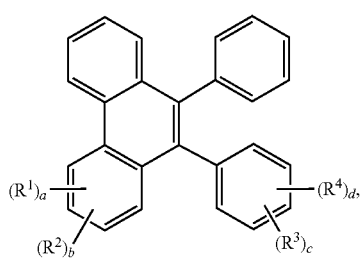

(1)

wherein $R^1$, $R^2$, $R^3$ and $R^4$ are independently selected from hydrogen, substituted or unsubstituted $C_6$ to $C_{38}$ aryl, substituted or unsubstituted $C_3$ to $C_{36}$ heteroaryl, —PO(R')$_2$, D, F, CN, or formula 2;

$$*\!-\!(Ar^1)_e\!-\!Ar^2,$$

(2)

wherein the substituents are selected from $C_6$ to $C_{18}$ aryl, $C_3$ to $C_{25}$ heteroaryl, —PO(R')$_2$, D, F or CN;

R' is independently selected from aryl or heteroaryl;

a, b, c, d and e are independently 0, 1 or 2, wherein at least one of a, b, c or d is 1 or 2;

wherein at least one of $R^1$, $R^2$, $R^3$ or $R^4$ is formula 2;

$Ar^1$ is selected from substituted or unsubstituted $C_6$ to $C_{38}$ arylene, substituted or unsubstituted $C_3$ to $C_{36}$ heteroarylene, wherein the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_{36}$ heteroaryl, wherein the substituents are selected from $C_6$ to $C_{18}$ aryl, $C_3$ to $C_{25}$ heteroaryl, —PO(R')$_2$, D, F or CN;

wherein $Ar^1$ does not contain one or more CN substituents when $Ar^2$ is substituted or unsubstituted $C_6$ to $C_{38}$ aryl;

wherein the following compounds 3 and 7 are excluded:

(3)

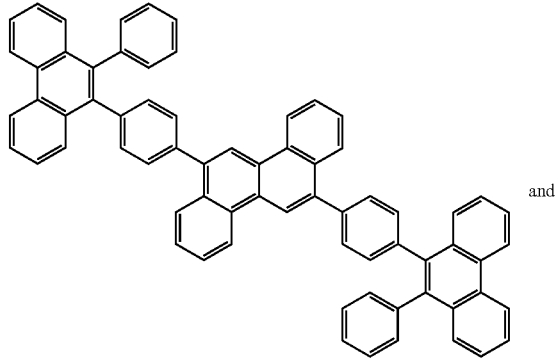

and (7)

According to one embodiment according to the compound of formula 1:

(1)

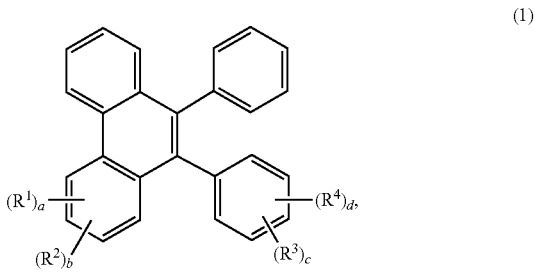

wherein $R^1$, $R^2$, $R^3$ and $R^4$ are independently selected from hydrogen, substituted or unsubstituted $C_6$ to $C_{38}$ aryl, substituted or unsubstituted $C_3$ to $C_{36}$ heteroaryl, —PO(R')$_2$, D, F, CN, or formula 2

$$*\!-\!\!(\!\!-\!\!Ar^1\!\!-\!\!)_e\!\!-\!\!Ar^2, \qquad (2)$$

wherein the substituents are selected from $C_6$ to $C_{18}$ aryl, $C_3$ to $C_{25}$ heteroaryl, —PO(R')$_2$, D, F or CN;

R' is independently selected from aryl or heteroaryl;

a, b, c, d and e are independently 0, 1 or 2, wherein at least one of a, b, c or d is 1 or 2;

wherein e is 1 or 2, if a, b and c are 0;

wherein at least one of $R^1$, $R^2$, $R^3$ or $R^4$ is formula 2;

$Ar^1$ is selected from substituted or unsubstituted $C_6$ to $C_{38}$ arylene, substituted or unsubstituted $C_3$ to $C_{36}$ heteroarylene, wherein the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_{36}$ heteroaryl, wherein the substituents are selected from $C_6$ to $C_{18}$ aryl, $C_3$ to $C_{25}$ heteroaryl, —PO(R')$_2$, D, F or CN;

wherein $Ar^1$ does not contain one or more CN substituents when $Ar^2$ is substituted or unsubstituted $C_6$ to $C_{38}$ aryl;

wherein
the following compound 3 is excluded:

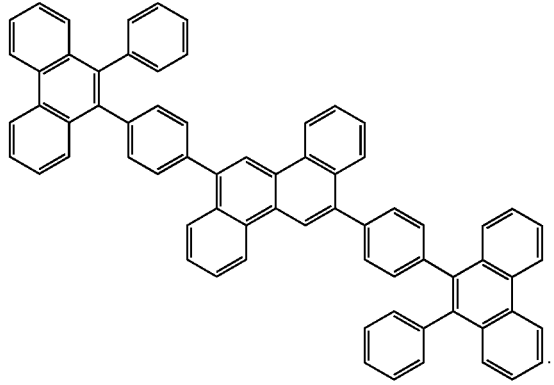

(3)

If not otherwise stated H can represent hydrogen or deuterium.

If not otherwise stated substituents may be selected from $C_1$ to $C_{16}$ alkyl, $C_1$ to $C_{16}$ alkoxy, $C_6$ to $C_{18}$ aryl, $C_3$ to $C_{25}$ heteroaryl, —PO(R')$_2$, D, F or CN, partially or perfluorinated $C_1$ to $C_{16}$ alkyl, partially or perdeuterated $C_1$ to $C_{16}$ alkyl, partially or perfluorinated $C_1$ to $C_{16}$ alkoxy, partially or perdeuterated $C_1$ to $C_{16}$ alkoxy, wherein R' is independently selected from alkyl, aryl or heteroaryl.

According to one embodiment of the compound of formula 1 and/or 2, wherein the substituents may be selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy.

According to one embodiment of the compound of formula 1 and/or 2, wherein the substituents may be preferably selected from $C_6$ to $C_{18}$ aryl, $C_3$ to $C_{25}$ heteroaryl, —PO(R')$_2$, D, F or CN, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy.

According to one embodiment of the compound of formula 1 and/or 2, wherein the substituents may be more preferably selected from $C_6$ to $C_{18}$ aryl, $C_3$ to $C_{25}$ heteroaryl, —PO(R')$_2$, D, F or CN.

According to one embodiment of the compound of formula 1 and/or 2, wherein R' may be independently selected from H, $C_1$ to $C_{16}$ alkyl, substituted or unsubstituted $C_6$ to $C_{18}$ aryl, or substituted or unsubstituted $C_3$ to $C_{25}$ heteroaryl, wherein the substituents are selected from D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy.

The heteroatom of the heteroaryl and heteroarylene can be selected from N, O, S, B, Si, P, Se, preferably from N, O and S. The heteroatom may be preferably selected from N, if not otherwise defined.

Preferably, a 6-member heteroaryl ring and/or 6-member heteroarylene ring comprises as a hetero-atom at least one to three N. Preferably, a 5-member heteroaryl ring and/or 5-member heteroarylene ring comprises as a hetero-atom at least one atom selected from O, S and Se, preferred O or S and more preferred O.

According to one embodiment of the compound of formula 1, wherein a compound having five aromatic six-member rings and one triazine heteroaryl are excluded.

According to one embodiment of the compound of formula 1, wherein the compound of formula 1 may comprises about 6 to about 14 six-member aromatic rings.

According to one embodiment of the compound of formula 1, wherein the compound of formula 1 may comprises about 7 to about 13 six-member aromatic rings.

According to one embodiment of the compound of formula 1, wherein the compound of formula 1 may comprises about 8 to about 12 six-member aromatic rings.

According to one embodiment of the compound of formula 1, wherein the compound of formula 1 may comprises about 9 to about 11 six-member aromatic rings.

According to one embodiment of the compound of formula 1, wherein the compound of formula 1 may comprises about 8 to about 11 six-member aromatic rings.

According to one embodiment of the compound of formula 1, wherein the compound of formula 1 may comprises about 8, about 9, about 10, or about 11 six-member aromatic rings.

According to one embodiment of the compound of formula 1, wherein the compound of formula 1 may comprises about 8 to about 11 six-member aromatic rings, and at least one six-member aromatic ring comprises an N-atom.

According to one embodiment of the compound of formula 1, wherein the compound of formula 1 may comprises about 6 to about 14 six-member aromatic rings, and at least about one 5-member ring.

According to one embodiment of the compound of formula 1, wherein the compound of formula 1 may comprises about 8 to about 11 six-member aromatic rings, and at least about one 5-member ring.

According to one embodiment of the compound of formula 1, wherein the compound of formula 1 may comprises at least about one six-member aromatic ring substituted with CN.

According to one embodiment of the compound of formula 1, wherein the compound of formula 1 may comprises at least about one six-member aromatic ring substituted with $C_1$ to $C_6$-dialkyl phosphine oxide and preferably substituted with dimethyl phospine oxide group.

According to one embodiment of the compound of formula 1, wherein the compound of formula 1 may comprises at least one hetero five-member ring with a heteroatom selected from O or S.

According to one embodiment of the compound of formula 1, wherein the compound of formula 1 may comprises at least one 6-member heteroaryl ring comprises 2 N-atoms to 3 N-atoms, preferably 3 N-atoms.

According to one embodiment of the compound of formula 1, wherein the compound of formula 1 may comprises at least two 6-member heteroaryl rings comprises 2 N-atoms to 3 N-atoms, preferably 3 N-atoms.

According to one embodiment of the compound of formula 1, wherein the compound of formula 1 may comprises at least three 6-member heteroaryl rings comprises 2 N-atoms to 3 N-atoms, preferably 3 N-atoms.

According to one embodiment of the compound of formula 1, wherein the compound of formula 1 may comprises at least four 6-member heteroaryl rings comprises 2 N-atoms to 3 N-atoms, preferably 3 N-atoms.

According to one embodiment of the compound of formula 1, wherein the compound of formula 1 may comprises at least one 5-member heteroaryl ring comprises O as the hetero atom.

According to one embodiment of the compound of formula 1, wherein the compound of formula 1 may comprises at least one 5-member heteroaryl ring comprises S as the hetero atom.

According to one embodiment of the compound of formula 1, wherein the compound of formula 1 may comprises at least one 5-member heteroaryl ring comprises Se as the hetero atom.

According to one embodiment of the compound of formula 1, wherein the compound of formula 1 may comprises at least two 5-member heteroaryl rings comprises O as the hetero atom.

According to one embodiment of the compound of formula 1, wherein the compound of formula 1 may comprises at least two 5-member heteroaryl rings comprises S as the hetero atom.

According to one embodiment of the compound of formula 1:

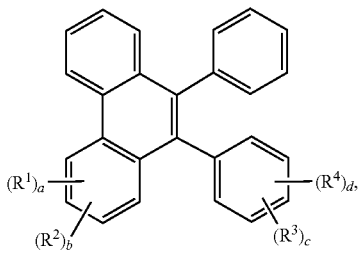

wherein
$R^1$, $R^2$, $R^3$ and $R^4$ are independently selected from hydrogen, substituted or unsubstituted $C_6$ to $C_{38}$ aryl, substituted or unsubstituted $C_3$ to $C_{36}$ heteroaryl or $C_1$ to $C_{16}$ alkyl group, —PO(R')$_2$, D, F, CN, or formula 2;

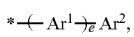

wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

R' is independently selected from $C_1$ to $C_{16}$ alkyl, substituted or unsubstituted $C_6$ to $C_{18}$ aryl, or substituted or unsubstituted $C_3$ to $C_{25}$ heteroaryl,
wherein the substituents are selected from D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

a, b, c, d and e are independently 0, 1 or 2, wherein at least one of a, b, c or d is 1 or 2;

wherein
at least one of $R^1$, $R^2$, $R^3$ or $R^4$ is formula 2;

$Ar^1$ is selected from substituted or unsubstituted $C_6$ to $C_{38}$ arylene, substituted or unsubstituted $C_3$ to $C_{36}$ heteroarylene or $C_1$ to $C_{16}$ alkylene group, wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_{36}$ heteroaryl or $C_1$ to $C_{16}$ alkyl group, wherein
the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

wherein
$Ar^1$ does not contain one or more CN substituents when $Ar^2$ is substituted or unsubstituted $C_6$ to $C_{38}$ aryl;

wherein
the following compound 3 is excluded:

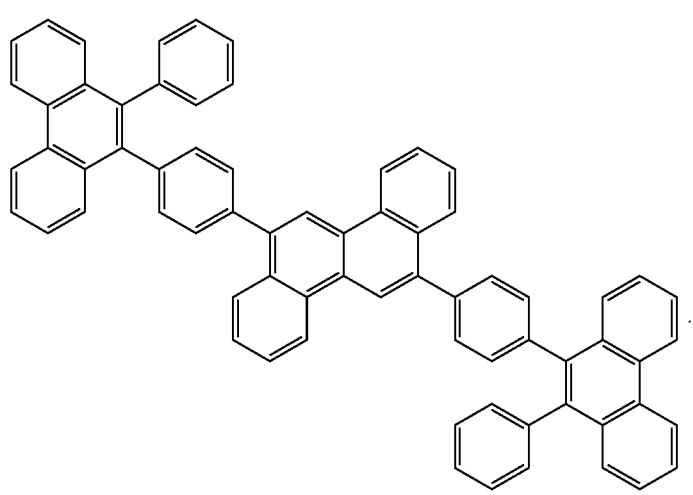

According to one embodiment of the compound of formula 1:

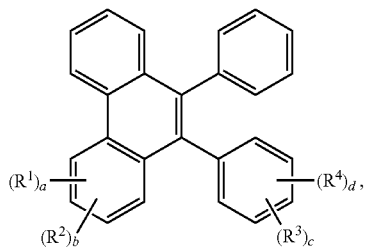

wherein
$R^1$, $R^2$, $R^3$ and $R^4$ are independently selected from hydrogen, substituted or unsubstituted $C_6$ to $C_{30}$ aryl, substituted or unsubstituted $C_3$ to $C_{29}$ heteroaryl or $C_1$ to $C_{12}$ alkyl group, —PO(R')$_2$, D, F, CN, or formula 2;

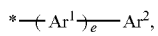

wherein
the substituents are selected from $C_6$ to $C_{12}$ aryl, $C_3$ to $C_{17}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{12}$ alkyl, $C_1$ to $C_{12}$ alkoxy, partially or perfluorinated $C_1$ to $C_{12}$ alkoxy, partially or perdeuterated $C_1$ to $C_{12}$ alkoxy;

R' is independently selected from $C_1$ to $C_{16}$ alkyl, substituted or unsubstituted $C_6$ to $C_{12}$ aryl, or substituted or unsubstituted $C_3$ to $C_{17}$ heteroaryl,
    wherein the substituents are selected from D, F or CN, $C_1$ to $C_{12}$ alkyl, partially or perfluorinated $C_1$ to $C_{12}$ alkyl, partially or perdeuterated $C_1$ to $C_{12}$ alkyl, $C_1$ to $C_{12}$ alkoxy, partially or perfluorinated $C_1$ to $C_{12}$ alkoxy, partially or perdeuterated $C_1$ to $C_{12}$ alkoxy;

a, b, c, d and e are independently 0, 1 or 2, wherein at least one of a, b, c or d is 1 or 2;

wherein
at least one of $R^1$, $R^2$, $R^3$ or $R^4$ is formula 2;
$Ar^1$ is selected from substituted or unsubstituted $C_6$ to $C_{38}$ arylene, substituted or unsubstituted $C_3$ to $C_{36}$ heteroarylene or $C_1$ to $C_{16}$ alkylene group, wherein
    the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_{36}$ heteroaryl or $C_1$ to $C_{16}$ alkyl group, wherein
    the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy;

wherein
$Ar^1$ does not contain one or more CN substituents when $Ar^2$ is substituted or unsubstituted $C_6$ to $C_{38}$ aryl;

wherein
the following compound 3 is excluded:

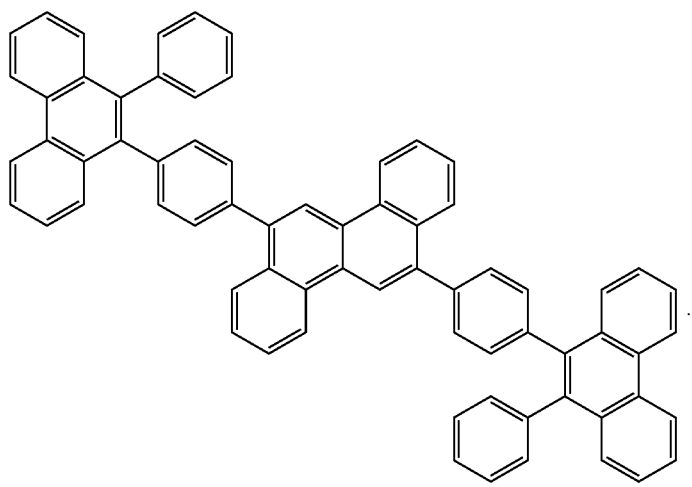

According to one embodiment of the compound of formula 1, wherein compounds having less than 6 six-member rings and more than 14 six-member rings are excluded.

According to one embodiment of the compound of formula 1, wherein compounds having less than 7 six-member rings and more than 13 six-member rings are excluded.

According to one embodiment of the compound of formula 1, wherein compounds having less than 8 six-member rings and more than 12 six-member rings are excluded.

According to one embodiment of the compound of formula 1, wherein compounds having less than 9 six-member rings and more than 11 six-member rings are excluded.

According to one embodiment of the compound of formula 1, wherein compounds having less than 6 six-member rings and more than 14 six-member rings and in addition no-hetero atom are excluded.

According to one embodiment of the compound of formula 1, wherein compounds having less than 6 six-member rings and more than 14 six-member rings and in addition more than 9 hetero atoms are excluded.

According to one embodiment of the compound of formula 1, wherein compounds having less than 8 six-member rings and more than 11 six-member rings and in addition more than 6 hetero atoms are excluded.

According to one embodiment of the compound of formula 1, wherein compounds having less than 8 six-member rings and more than 11 six-member rings and in addition less than 2 hetero atoms and more than 6 hetero atoms are excluded.

According to one embodiment of the compound of formula 1, wherein compounds having less than 6 six-member rings and more than 14 six-member rings and in addition hetero atoms that are different to N, O, P and S are excluded.

According to one embodiment of the compound of formula 1, wherein compounds having less than 6 six-member rings and more than 14 six-member rings and further no hetero atom are excluded.

According to one embodiment of the compound of formula 1, wherein a, b, c, d and e are independently 0, 1 or 2, wherein at least two of a, b, c or d is 1 or 2.

According to one embodiment of the compound of formula 1, wherein a, b, c, d and e are independently 0, 1 or 2, wherein at least two of a, b, c or d is 1.

According to one embodiment of the compound of formula 1, wherein a and e are 1; b, c, d are 0.

According to one embodiment of the compound of formula 1, wherein b and e are 1; a, c, d are 0.

According to one embodiment of the compound of formula 1, wherein c and e are 1; a, b, d are 0.

According to one embodiment of the compound of formula 1, wherein d and e are 1; a, b, c are 0.

According to one embodiment of the compound of formula 1, wherein a, c and e are 1; b and d are 0.

According to one embodiment of the compound of formula 1, wherein a, d and e are 1; b, and c are 0.

According to one embodiment of the compound of formula 1, wherein a and c are 1; b, d, e are 0.

According to one embodiment of the compound of formula 1, wherein a and d are 1; b, c, e are 0.

According to one embodiment of the compound of formula 1, wherein b and c are 1; a, d, e are 0.

According to one embodiment of the compound of formula 1, wherein b and d are 1; a, c, e are 0.

According to one embodiment of the compound of formula 1, wherein a, b, c and e are 1; d is 0.

According to one embodiment of the compound of formula 1, wherein b, c, d and e are 1; a is 0.

According to one embodiment of the compound of formula 1, wherein a, c, d and e are 1; b is 0.

According to one embodiment of the compound of formula 1, wherein a, b, d and e are 1; c is 0.

According to one embodiment of the compound of formula 1, wherein b, c and d are 1; a and e is 0.

According to one embodiment of the compound of formula 1, wherein a, c and d are 1; b and e is 0.

According to one embodiment of the compound of formula 1, wherein a, b and d are 1; c and e is 0.

According to one embodiment of the compound of formula 1, wherein a, b and c are 1; d and e is 0.

According to one embodiment of the compound of formula 1, wherein at least one of $R^1$, $R^2$, $R^3$ and $R^4$ are independently selected from substituted or unsubstituted heteroaryl selected from a group comprising of pyridine, pyrimidine, triazine, quinoline, quinoxaline, benzo acridine, dibenzo acridine, phenanthroline, carbazole, dibenzofurane, dibenzothiophene.

According to one embodiment of the compound of formula 1, wherein $R^1$ and $R^3$, or $R^2$ and $R^4$, or $R^1$ and $R^4$, or $R^2$ and $R^4$ are independently selected from substituted or unsubstituted heteroaryl selected from a group comprising of pyridine, pyrimidine, triazine, quinoline, quinoxaline, benzo acridine, dibenzo acridine, phenanthroline, carbazole, dibenzofurane, dibenzothiophene.

According to one embodiment of the compound of formula 1, wherein $R^1$ and $R^3$ are independently selected from substituted or unsubstituted heteroaryl selected from a group comprising of pyridine, pyrimidine, triazine, quinoline, quinoxaline, benzo acridine, dibenzo acridine, phenanthroline, carbazole, dibenzofurane, dibenzothiophene; and $R^2$ and $R^4$ are hydrogen.

According to one embodiment of the compound of formula 1, wherein $R^2$ and $R^3$ are independently selected from substituted or unsubstituted heteroaryl selected from a group comprising of pyridine, pyrimidine, triazine, quinoline, quinoxaline, benzo acridine, dibenzo acridine, phenanthroline, carbazole, dibenzofurane, dibenzothiophene; and $R^1$ and $R^4$ are hydrogen.

According to one embodiment of the compound of formula 1, wherein one of $R^1$, $R^2$, $R^3$ and $R^4$ is selected from substituted or unsubstituted heteroaryl selected from a group comprising of pyridine, pyrimidine, triazine, quinoline, quinoxaline, benzo acridine, dibenzo acridine, phenanthroline, carbazole, dibenzofurane, dibenzothiophene; and the other are hydrogen.

According to one embodiment of the compound of formula 1 and/or 2, wherein the substituents on $Ar^1$ may be selected from $C_6$ to $C_{18}$ aryl, $C_3$ to $C_{25}$ heteroaryl, —PO(R')$_2$, D, F or CN.

According to one embodiment of the compound of formula 1 and/or 2, wherein the substituents on $Ar^2$ may be selected from $C_6$ to $C_{18}$ aryl, $C_3$ to $C_{25}$ heteroaryl, —PO(R')$_2$, D, F or CN.

According to one embodiment the compound of formula 1 may comprises at least three to six phenyl rings that are part of a fused ring system.

According to one embodiment the compound of formula 1 may comprises at least 3 to 10 phenyl rings that are part of a fused ring system, or at least 5 to 8 phenyl rings that are part of a fused ring system.

According to one embodiment of the compound of formula 1, wherein
  at least two of a, b, c or d are 0, 1 or 2, preferably at least two of a, b, c or d are 0 or 1; or
  a and b are 0 and c or d is independently selected from 1 or 2, preferably a and b are 0 and c or d is 1; or
  c and d are 0 and a or b is independently selected from 1 or 2, preferably c and d are 0 and a orb is 1; or
  a and c are 0 and b or d is independently selected from 1 or 2, preferably a and c are 0 and b or d is 1; or
  b and d are 0 and a or c is independently selected from 1 or 2, preferably b and d are 0 and a or c is 1; or
  at least three selected from a, b, c and d are 0 and one selected from a, b, c or d is 1; or
  at least three selected from a, b, c and d are 1 or 2, preferably at least two of a, b, c and d is 1.

According to another embodiment, wherein for formula 2 e can be 0, 1 or 2, further preferred 1 or 2 and more preferred 2.

According to another embodiment, wherein for formula 1 at least two of $R^1$, $R^2$, $R^3$ and $R^4$ are selected same when a+b+c+d≥2, preferably $R^1$ and $R^2$ or $R^3$ and $R^4$ are selected same when a+b+c+d≥2, further preferred $R^1$ and $R^3$ or $R^2$ and $R^4$ are selected same when a+b+c+d≥2.

According to another embodiment, wherein for formula 1 $R^1$, $R^2$, $R^3$ and $R^4$ are independently selected from H, nitrile, phenyl, naphthyl, biphenyl, pyridinyl, dibenzofuran, dibenzothiophene or carbazole; preferably at least one of $R^1$, $R^2$, $R^3$ or $R^4$ is independently selected from nitrile, phenyl, naphthyl, biphenyl, pyridinyl, dibenzofuran, dibenzothiophene or carbazole; preferably at least two of $R^1$, $R^2$, $R^3$ and $R^4$ are independently selected from nitrile, phenyl, naphthyl, biphenyl, pyridinyl, dibenzofuran, dibenzothiophene or carbazole; further preferred at least three of $R^1$, $R^2$, $R^3$ and $R^4$ are independently selected from nitrile, phenyl, naphthyl, biphenyl, pyridinyl, dibenzofuran, dibenzothiophene or carbazole; in addition preferred at least three of $R^1$, $R^2$, $R^3$ and $R^4$ are independently selected from nitrile, phenyl, naphthyl, biphenyl, pyridinyl, dibenzofuran, dibenzothiophene or carbazole.

According to another embodiment, wherein for formula 1 at most one of $R^1$, $R^2$, $R^3$ or $R^4$ is H; preferably at most two of $R^1$, $R^2$, $R^3$ and $R^4$ are H; and more preferred at most three of $R^1$, $R^2$, $R^3$ and $R^4$ are H.

According to another embodiment of formula 1, wherein two of $R^1$, $R^2$, $R^3$ and $R^4$ are formula 2, preferably one of $R^1$, $R^2$, $R^3$ or $R^4$ is formula 2.

According to another embodiment of formula 2, wherein $Ar^1$ is selected from substituted or unsubstituted phenylene, biphenylene, terphenylene, naphthylene, phenanthrylene, triphenylene, anthracenylene, wherein the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy.

According to another embodiment of formula 2, wherein $Ar^2$ is selected from substituted or unsubstituted aryl selected from a group consisting of anthracenyl, fluoranthenyl, pyrenyl, substituted or unsubstituted heteroaryl selected from a group consisting of pyridine, pyrimidine, triazine, quinoline, quinoxaline, benzoacridine, dibenzoacridine, phenanthroline, carbazole, dibenzofurane, dibenzothiophene, wherein the substituents are selected from $C_6$ to $C_{18}$ aryl, $C_3$ to $C_{25}$ heteroaryl, —PO(R')$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy.

According to another embodiment of formula 1, wherein $R^1$, $R^2$, $R^3$ and $R^4$ are independently selected from hydrogen, CN, or D1 to D54:

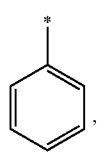

D1

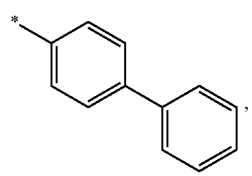

D2

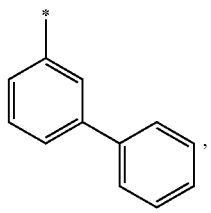

D3

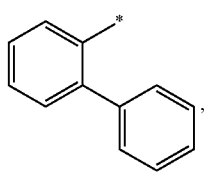

D4

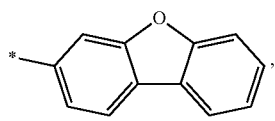

D5

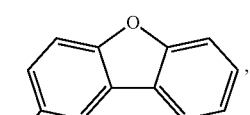

D6

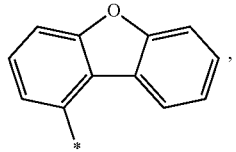

D7

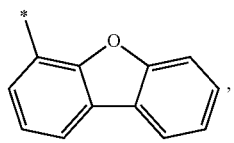

D8

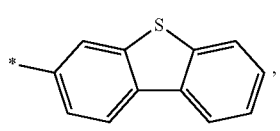

D9

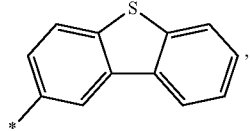

D10

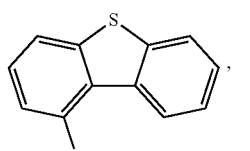

D11

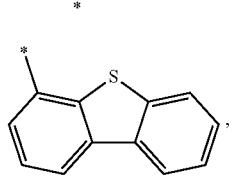

D12

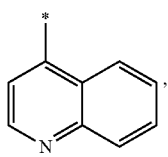 D13
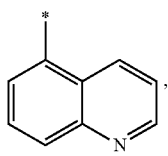 D14
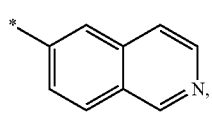 D15
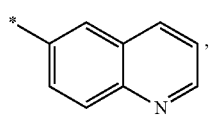 D16
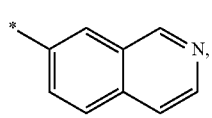 D17
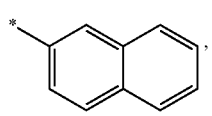 D18
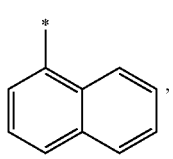 D19
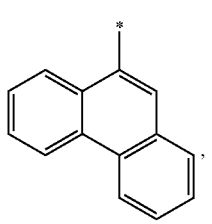 D20
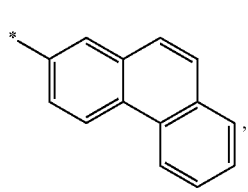 D21
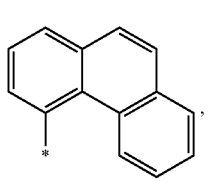 D22
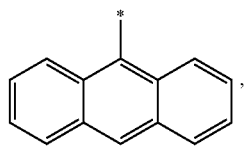 D23
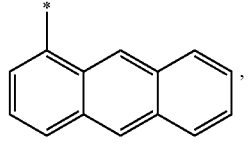 D24
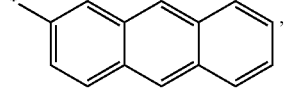 D25
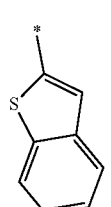 D26
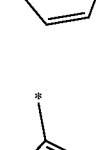 D27
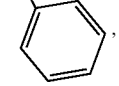 D28
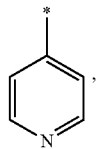 D29
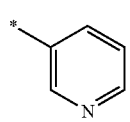 D30
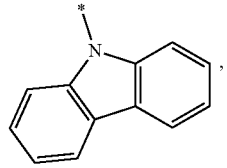 D31

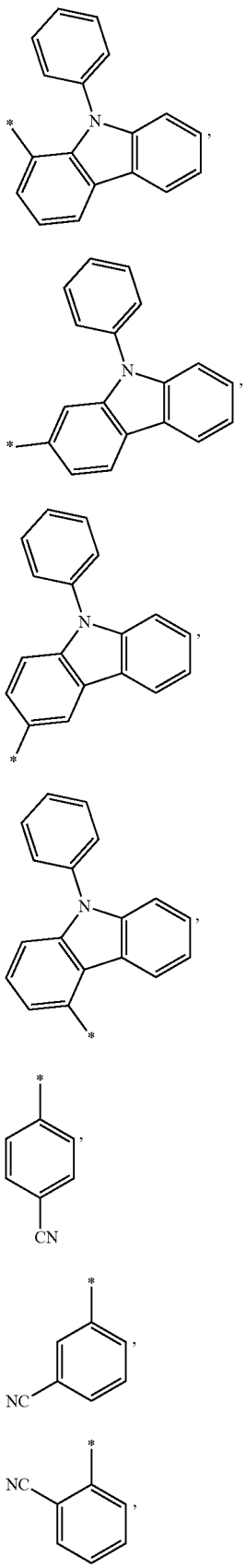
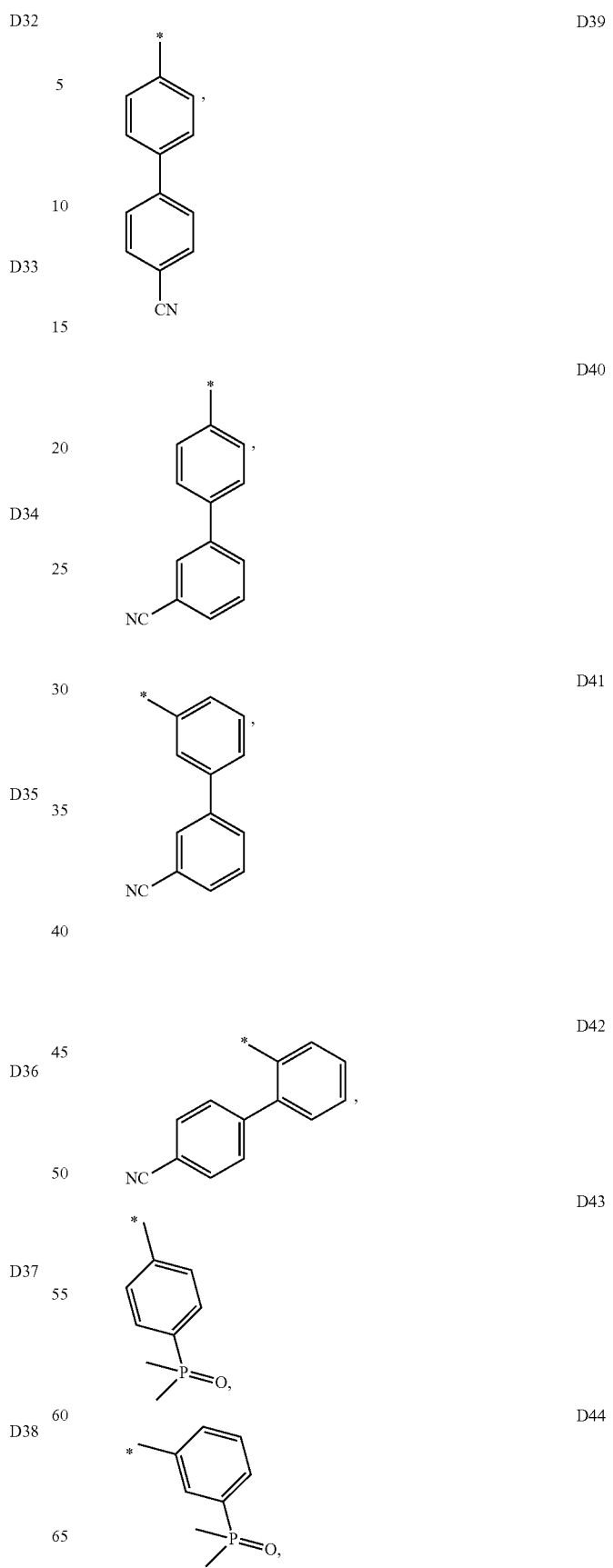

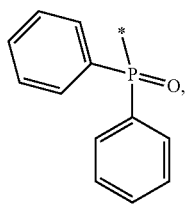
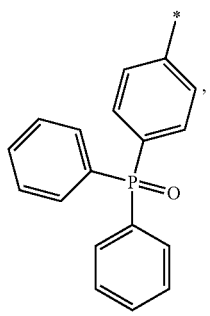
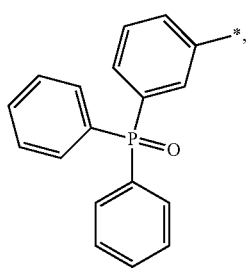
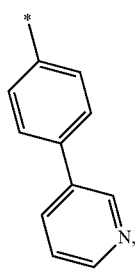
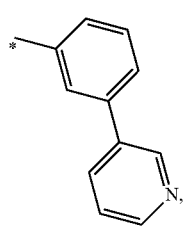
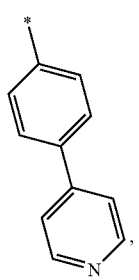
D45
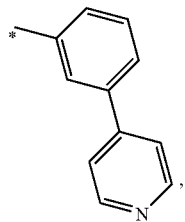
D46
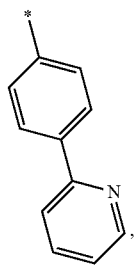
D47
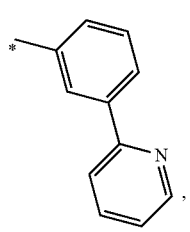
D48
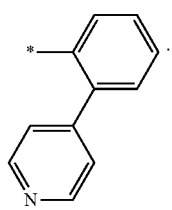
D49
D50
D51
D52
D53
D54
According to another embodiment of formula 2, wherein $Ar^1$ is selected from E1 to E14:
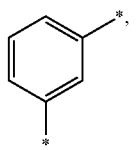  E1
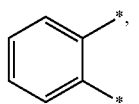  E2
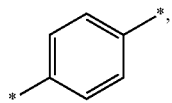  E3

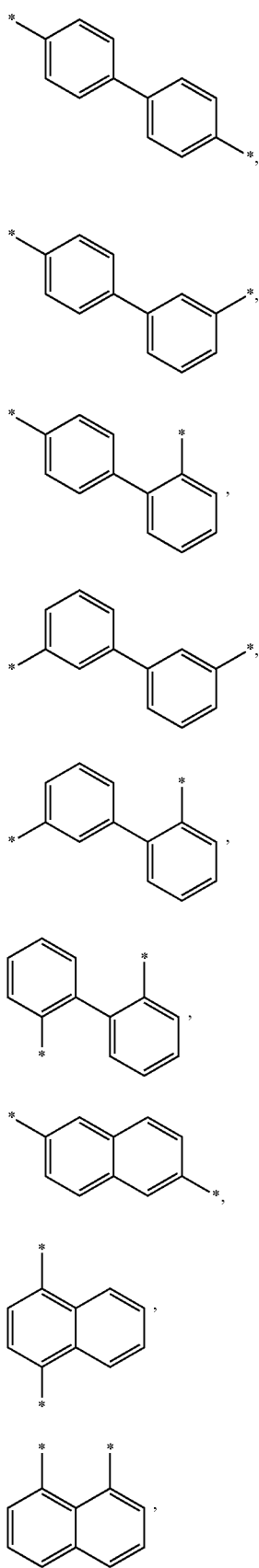
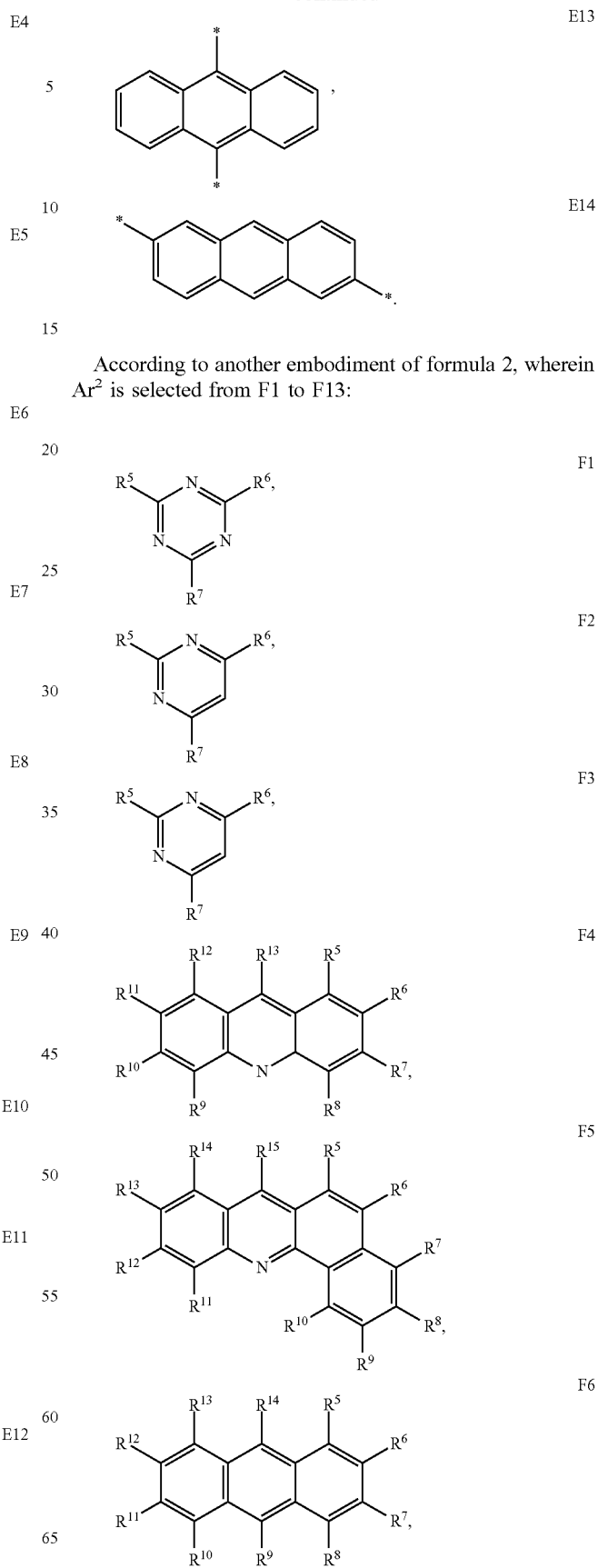
According to another embodiment of formula 2, wherein Ar² is selected from F1 to F13:

-continued

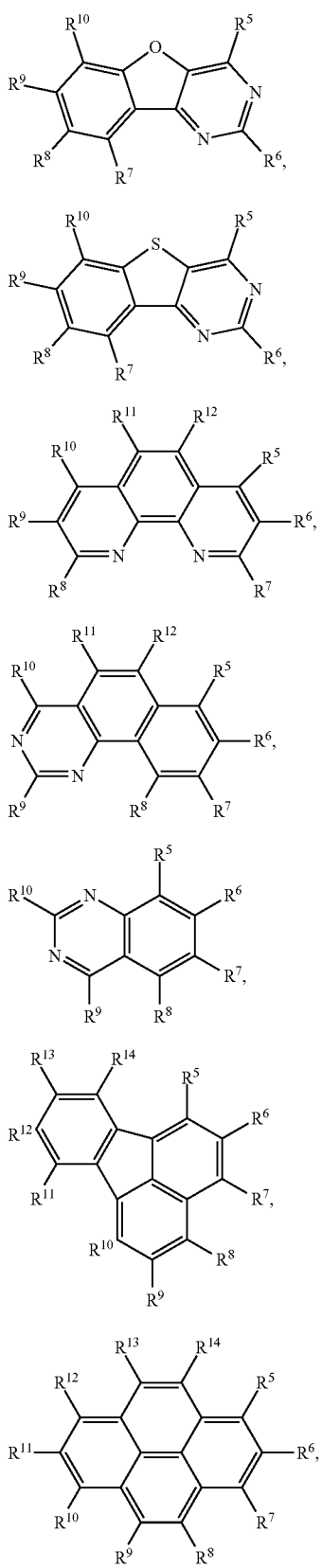

wherein $R^5$, $R^6$, $R^7$, $R^8$, $R^9$, $R^{10}$, $R^{11}$, $R^{12}$, $R^{13}$, $R^{14}$ are independently selected from single bond, hydrogen, substituted or unsubstituted phenyl, naphthyl, biphenyl, pyridinyl, dibenzofuryl, benzofuranyl, dibenzothienyl, benzothiophenyl, anthracenyl, phenanthryl, carbazolyl, wherein the substituents are selected from $C_6$ to $C_{18}$ aryl, $C_3$ to $C_{25}$ heteroaryl, —POR'$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy; and wherein one of $R^5$, $R^6$, $R^7$, $R^8$, $R^9$, $R^{10}$, $R^{11}$, $R^{12}$, $R^{13}$, $R^{14}$ represents a single bond only, and the single bond is the single bond that bonds $Ar^2$ to $Ar^1$.

According to another embodiment of formula 2, wherein $Ar^2$ is selected from F1 to F13 wherein when two or more of $R^5$, $R^6$, $R^7$, $R^8$, $R^9$, $R^{10}$, $R^{11}$, $R^{12}$, $R^{13}$, $R^{14}$ are independently selected from substituted or unsubstituted phenyl, naphthyl, biphenyl, pyridinyl, dibenzofuryl, benzofuranyl, dibenzothienyl, benzothiophenyl, anthracenyl, phenanthryl, carbazolyl, the two or more of $R^5$, $R^6$, $R^7$, $R^8$, $R^9$, $R^{10}$, $R^{11}$, $R^{12}$, $R^{13}$, $R^{14}$ are same or different and more preferably different, wherein the substituents are selected from $C_6$ to $C_{18}$ aryl, $C_3$ to $C_{25}$ heteroaryl, —POR'$_2$, D, F or CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, partially or perdeuterated $C_1$ to $C_{16}$ alkoxy; and wherein one of $R^5$, $R^6$, $R^7$, $R^8$, $R^9$, $R^{10}$, $R^{11}$, $R^{12}$, $R^{13}$, $R^4$ represents a single bond only, and the single bond is the single bond that bonds $Ar^2$ to $Ar^1$.

According to another embodiment of formula 2, wherein $R^5$, $R^6$, $R^7$, $R^8$, $R^9$, $R^{10}$, $R^{11}$, $R^{12}$, $R^{13}$, $R^4$ are independently selected from G1 to G72:

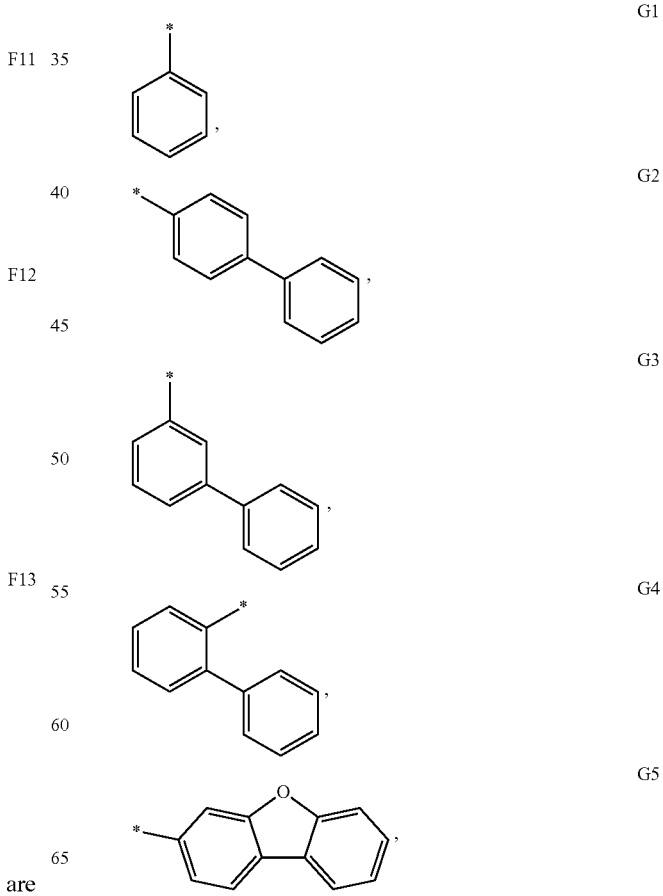

-continued
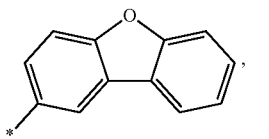, G6
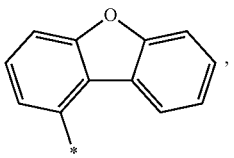, G7
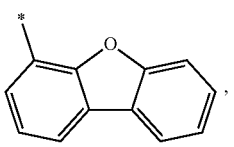, G8
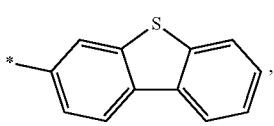, G9
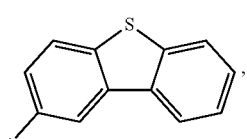, G10
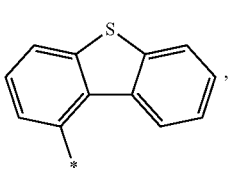, G11
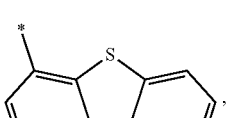, G12
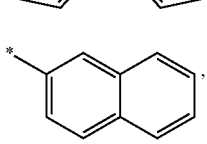, G13
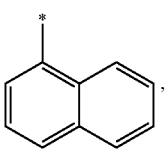, G14
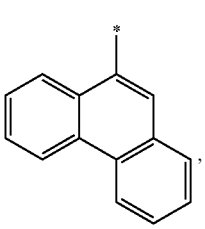, G15
-continued
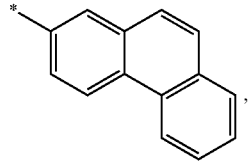, G16
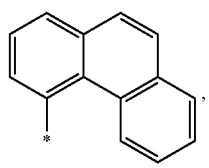, G17
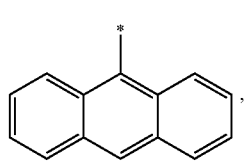, G18
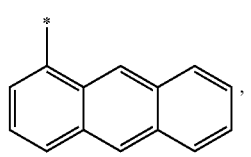, G19
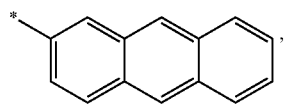, G20
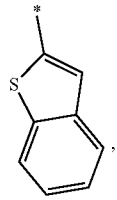, G21
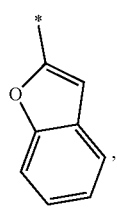, G22
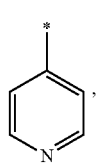, G23
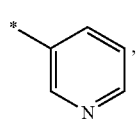, G24
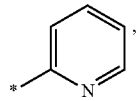, G25

-continued
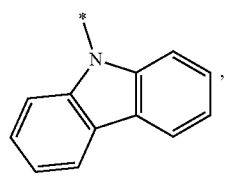
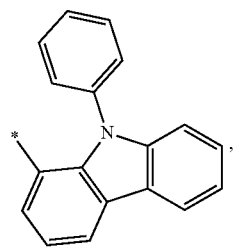
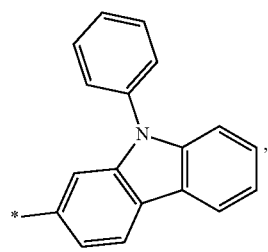
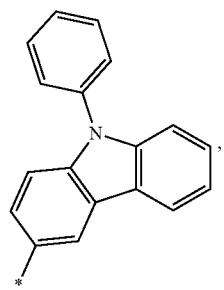
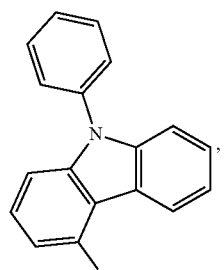
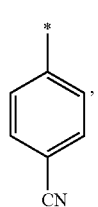
-continued
G26 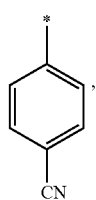
G27 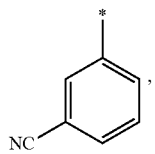
G28 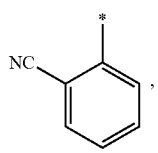
G29 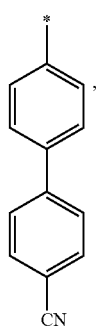
G30 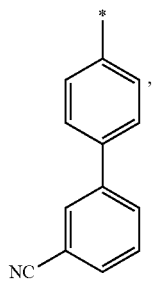
G31 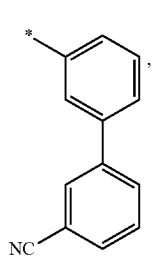
G32
G33
G34
G35
G36
G37
G38 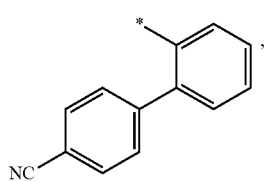

-continued
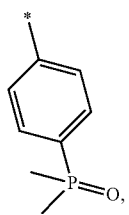
G39
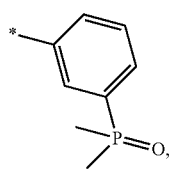
G40
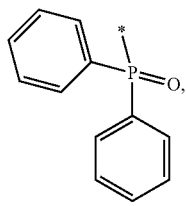
G41
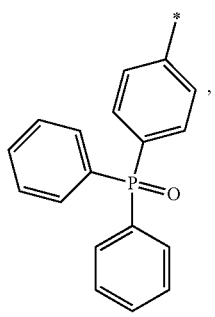
G42
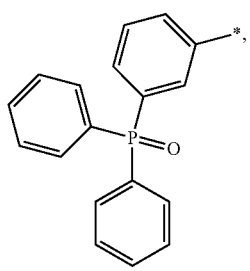
G43
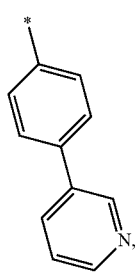
G44
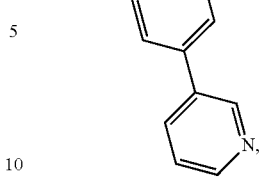
G45
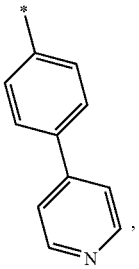
G46
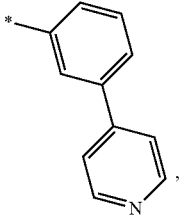
G47
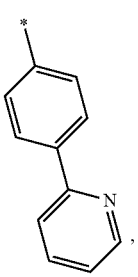
G48
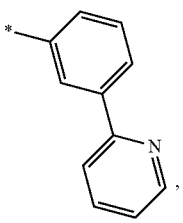
G49
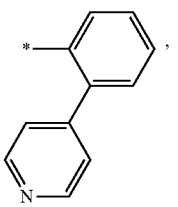
G50
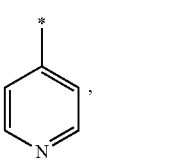
G51

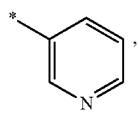
G52
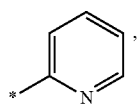
G53
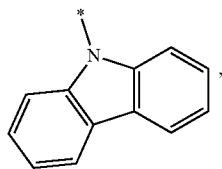
G54
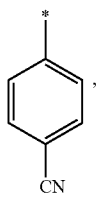
G55
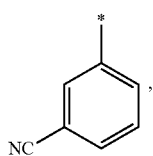
G56
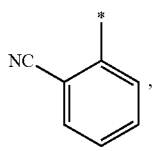
G57
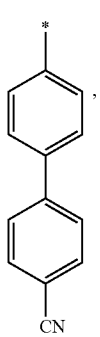
G58
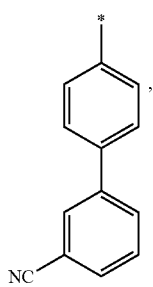
G59
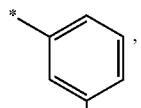
G60
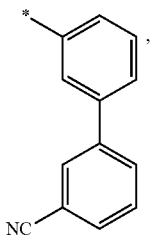
G61
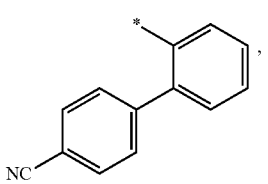
G62
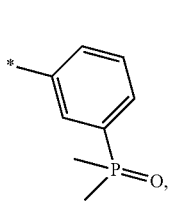
G63
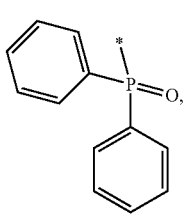
G64
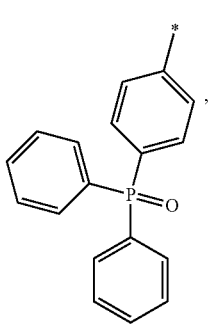
G65
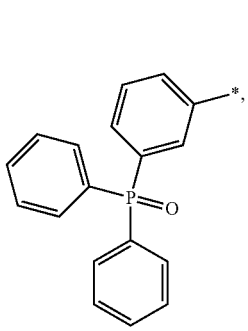

G66
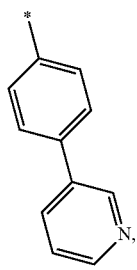
G67
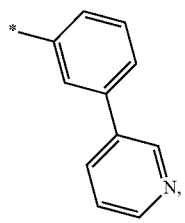
G68
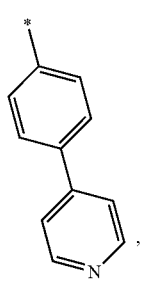
G69
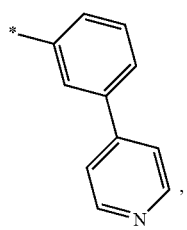
G70
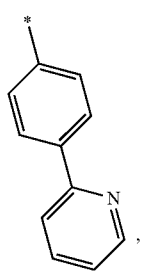
G71
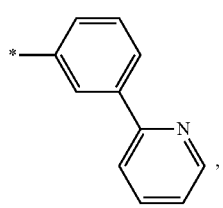
G72
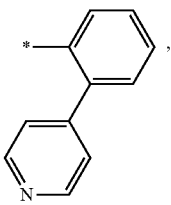
According to another embodiment of formula 2, wherein Ar² is selected from H1 to H92:
H1
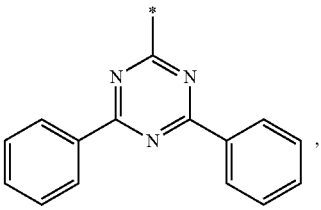
H2
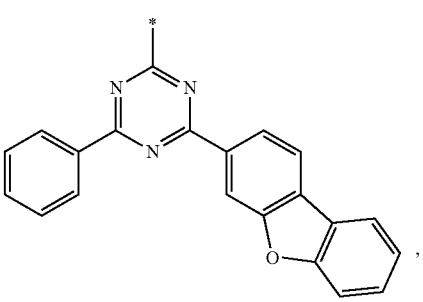
H3
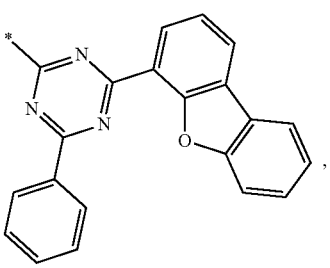
H4
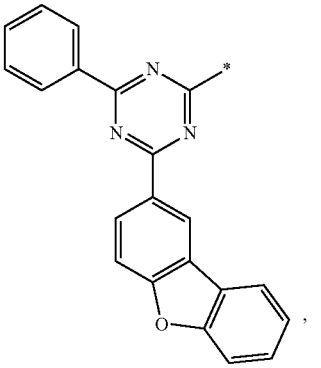

H5
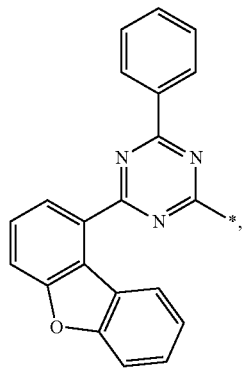
H6
H7
H8
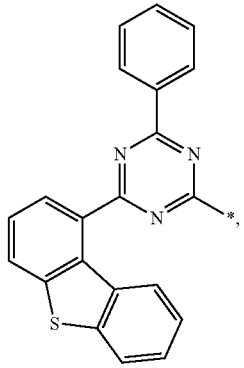
H9
H10
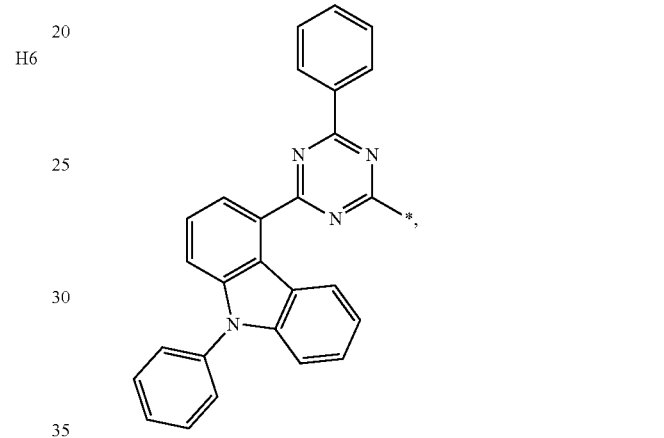
H11
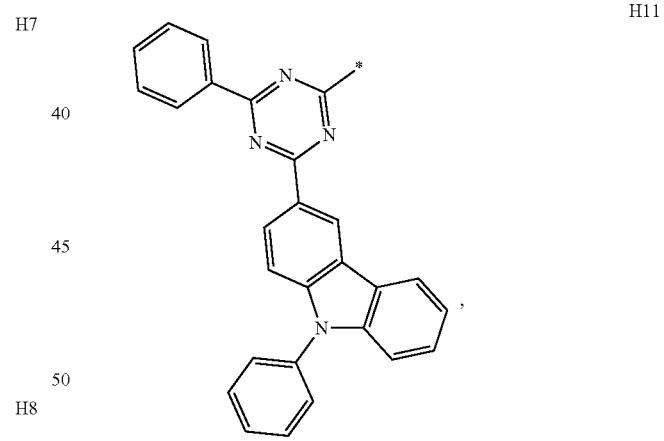
H12
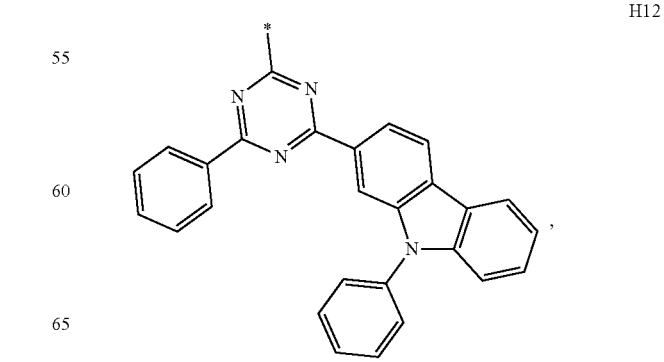

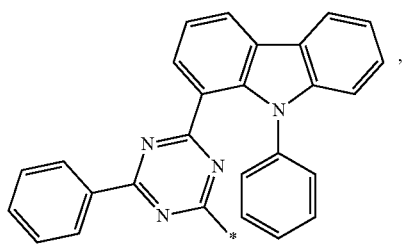
H13
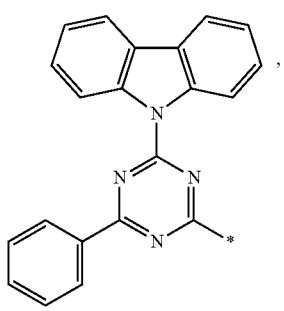
H14
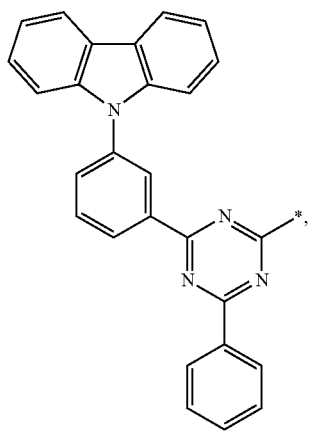
H15
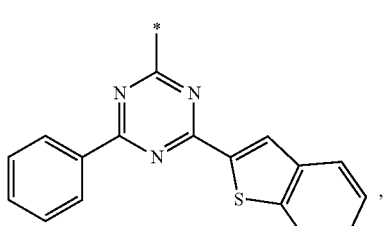
H16
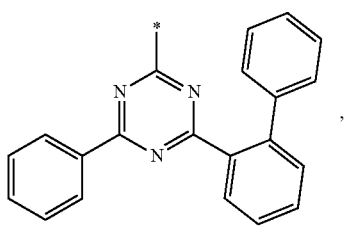
H17
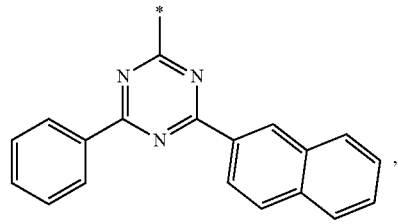
H18
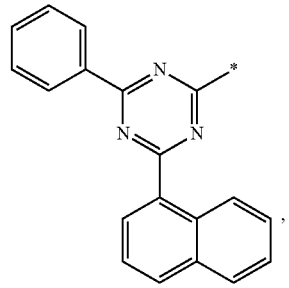
H19
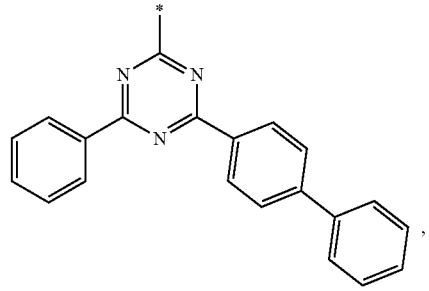
H20
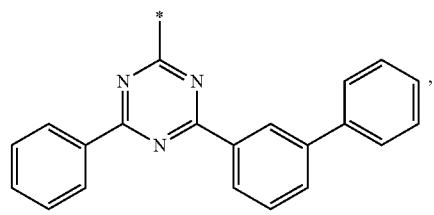
H21
H22
H23
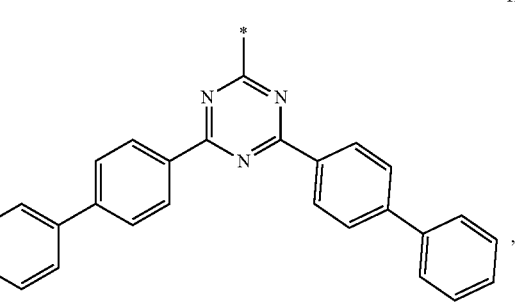

H24
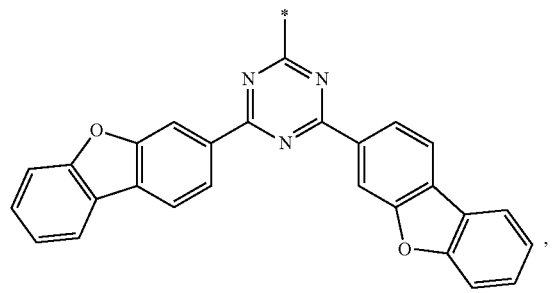
H25
H26
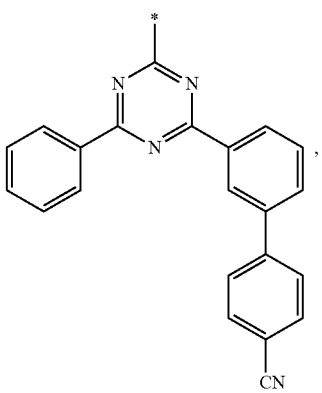
H27
H28
H29
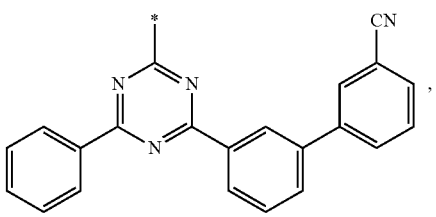
H30
H31
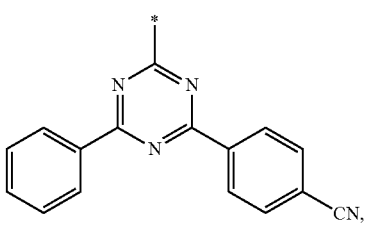
H32
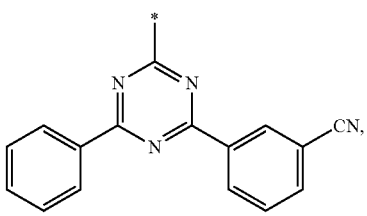
H33
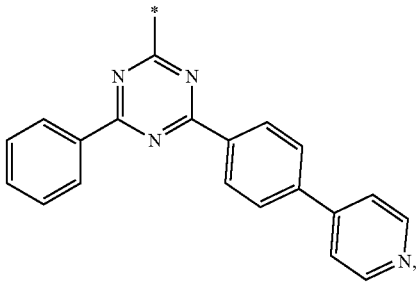
H34
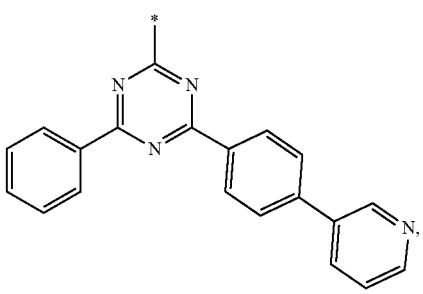

-continued
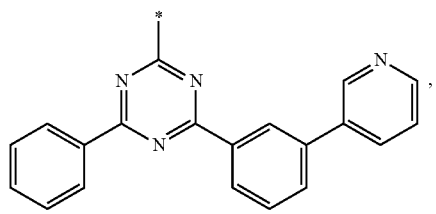
H35
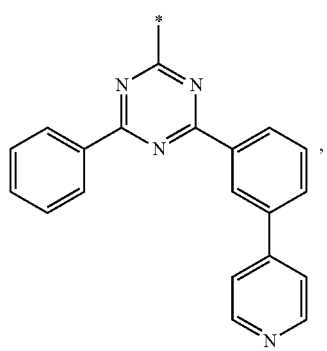
H36
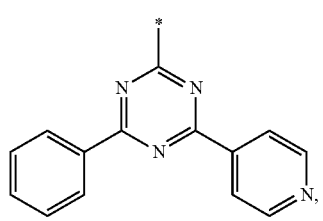
H37
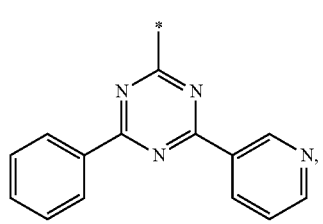
H38
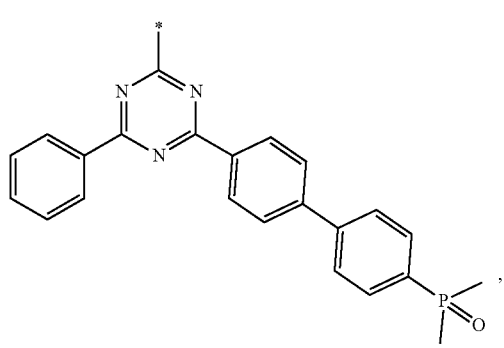
H39
-continued
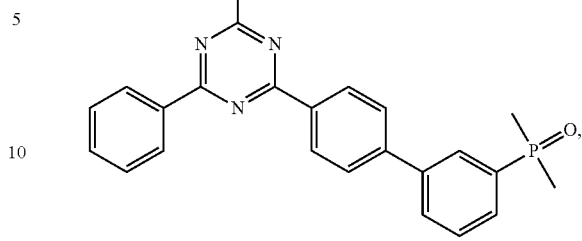
H40
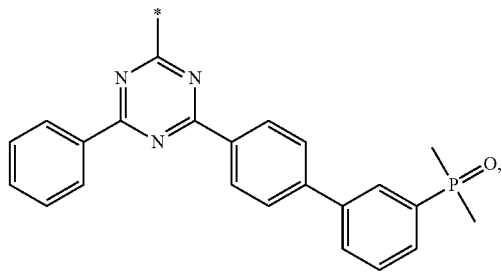
H41
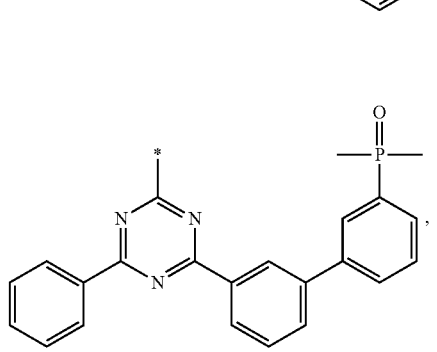
H42
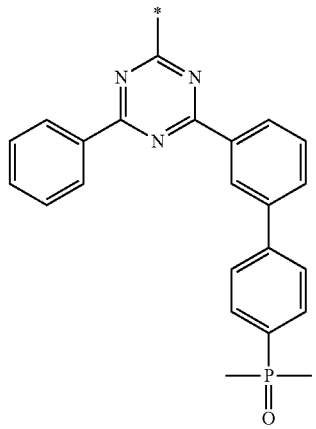
H43
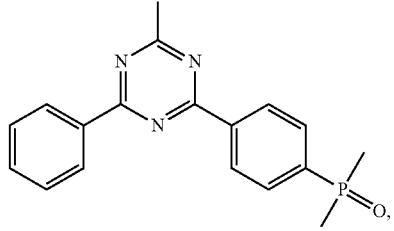
H44
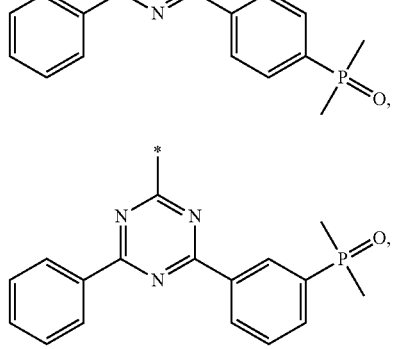

| | |
|---|---|
| H45 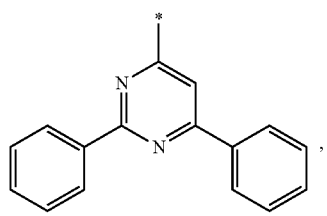 | H52 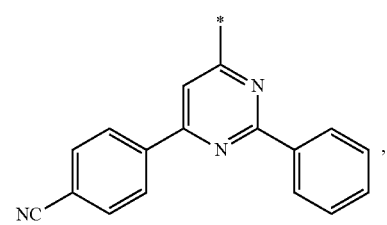 |
| H46 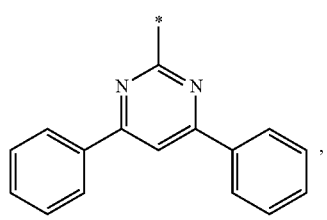 | H53 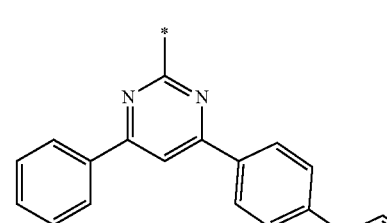 |
| H47 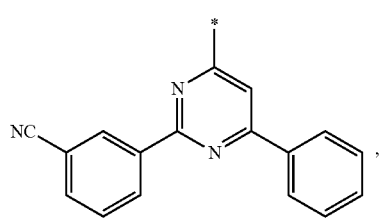 | H54 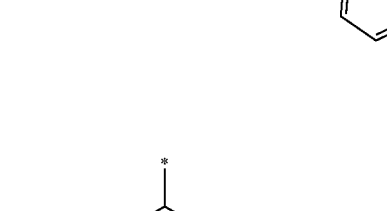 |
| H48 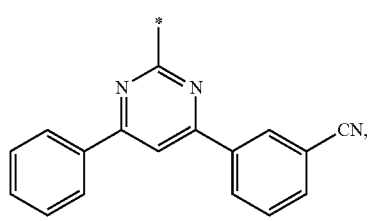 | H55 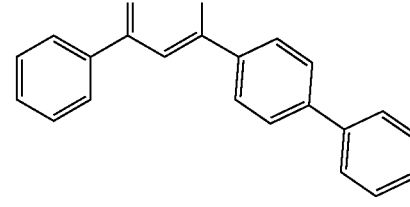 |
| H49 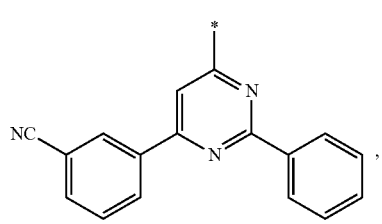 | |
| H50 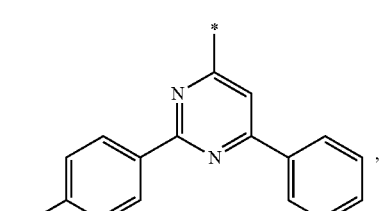 | H56 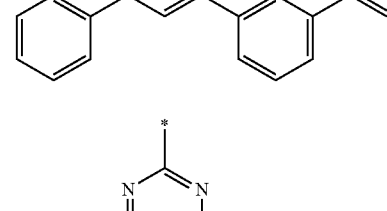 |
| H51 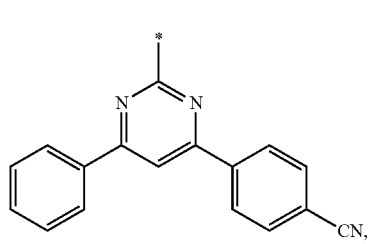 | |

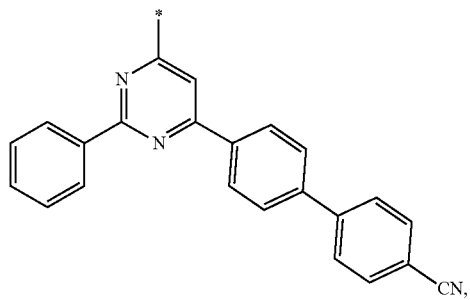
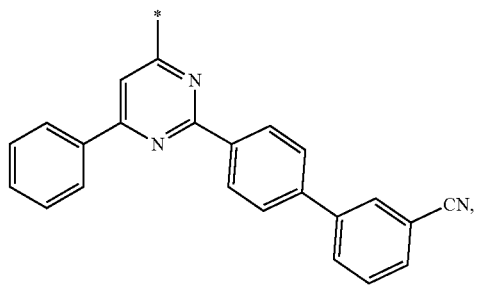

H67 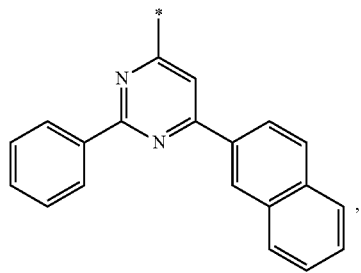
H68 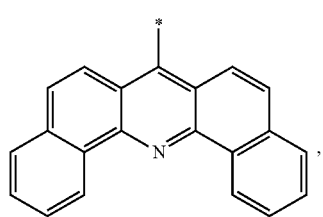
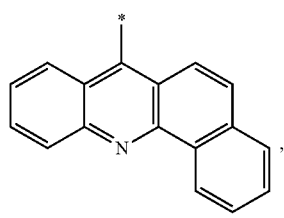
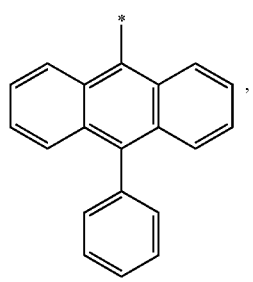
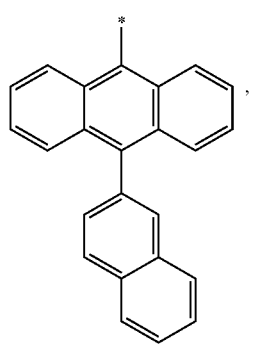
H72 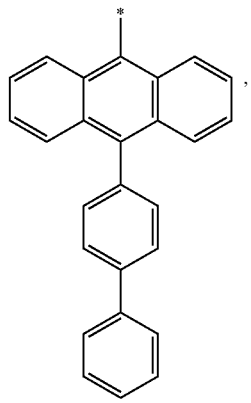
H73 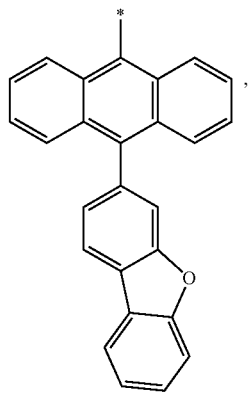
H74 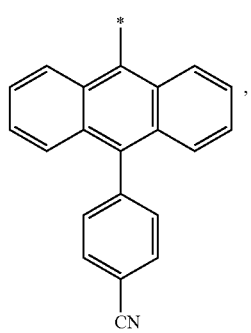
H75 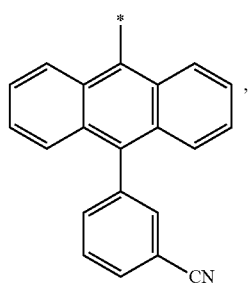

H76 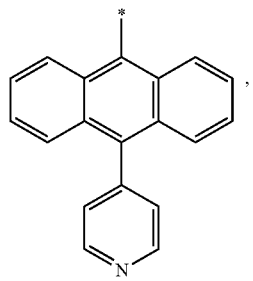
H77 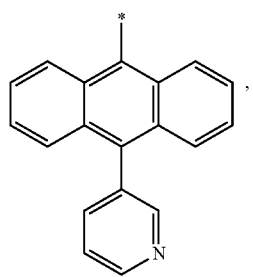
H78 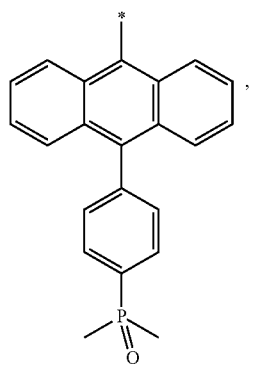
H79 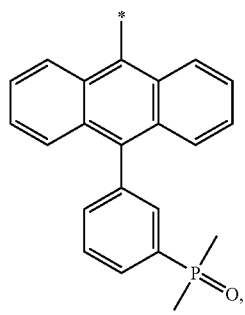
H80 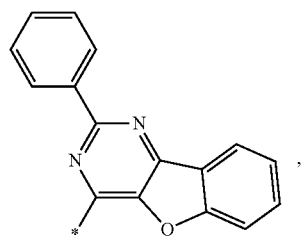
H81 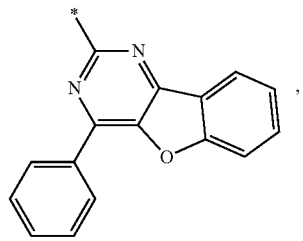
H82 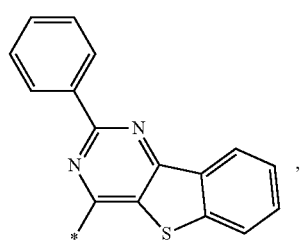
H83 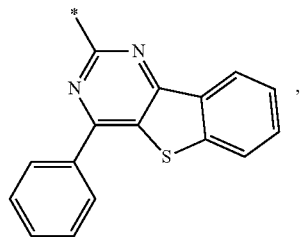
H84 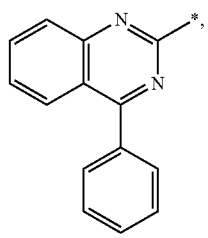
H85 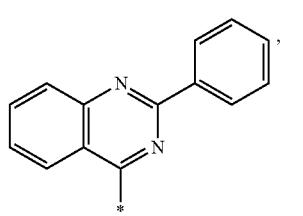
H86 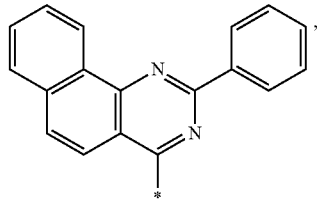

H87 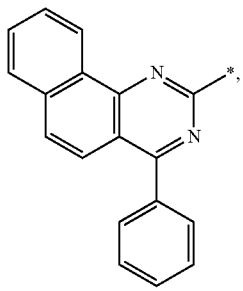
H88 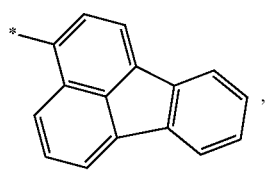
H89 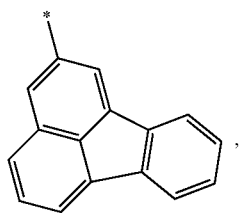
H90 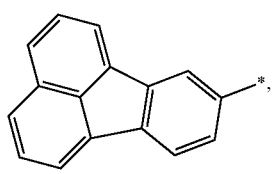
H91 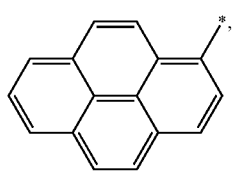
H92 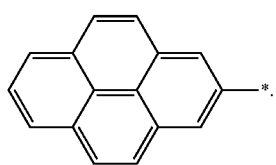
J1 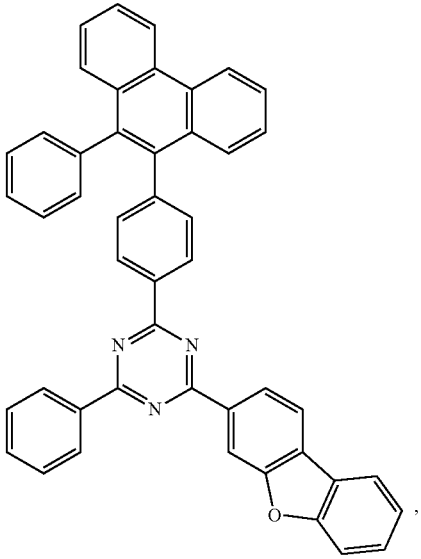
J2 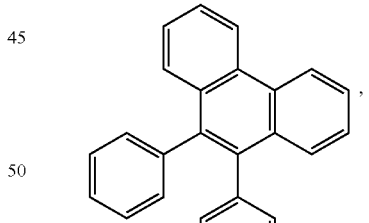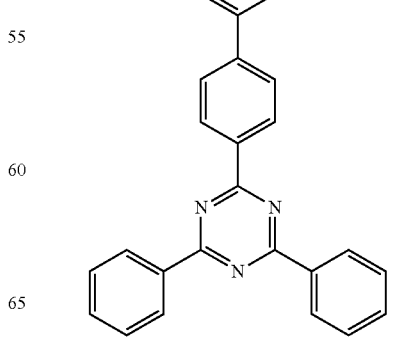
According to another embodiment, wherein the compound of formula 1 is selected from J1 to J53:

J3
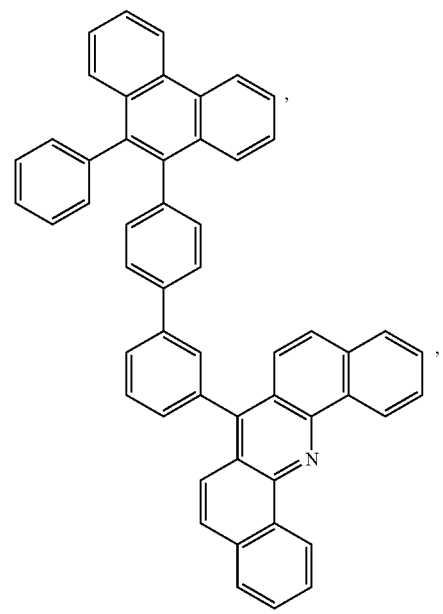
J4
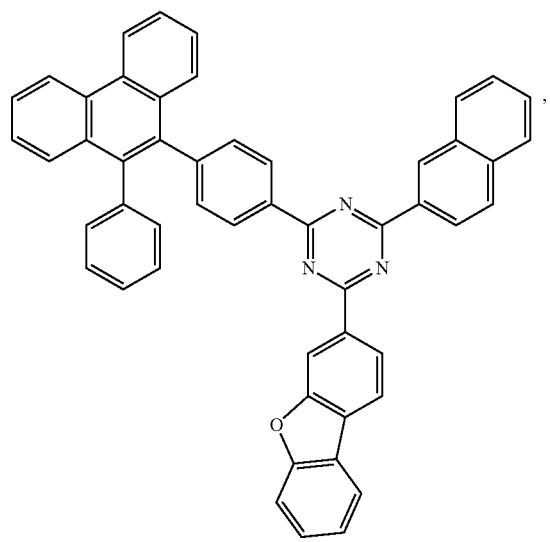
J5
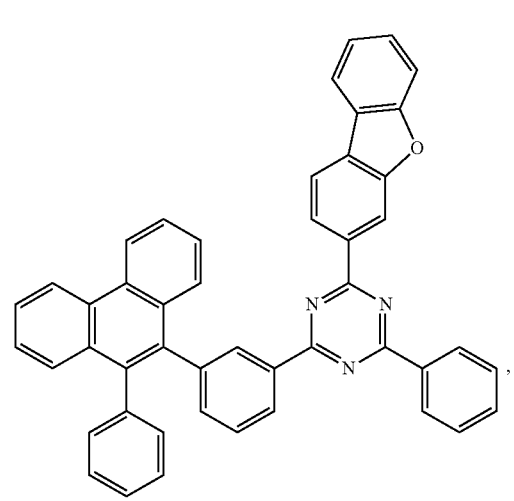
J6
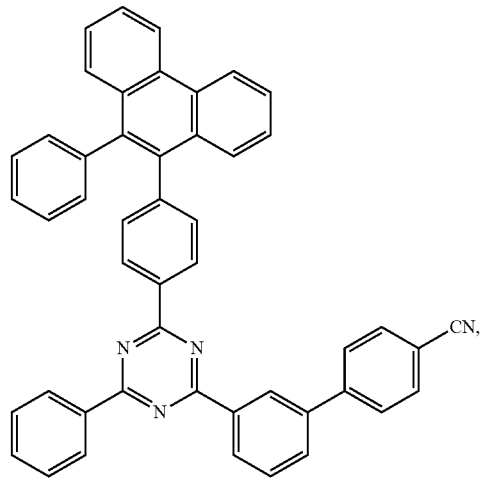
J7
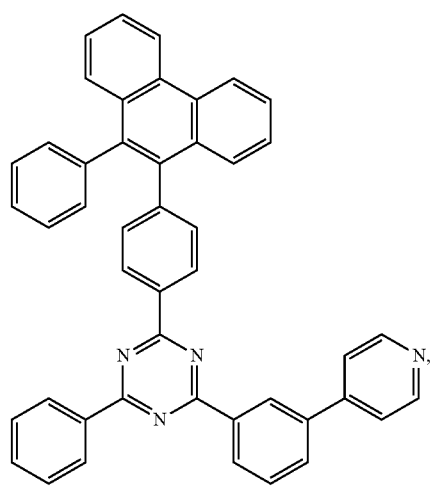
J8
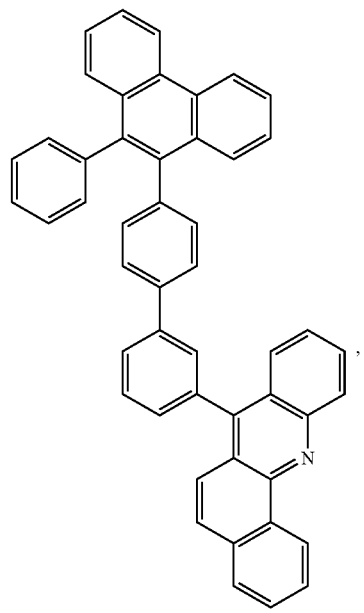

J9
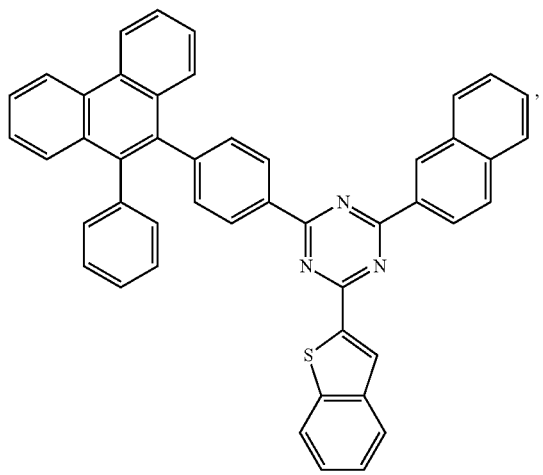
J10
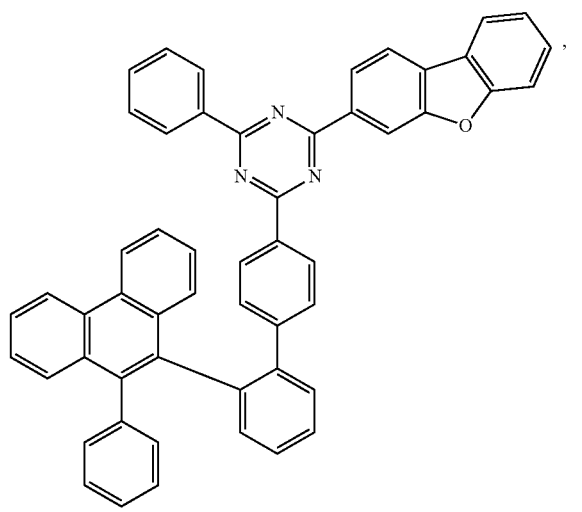
J11
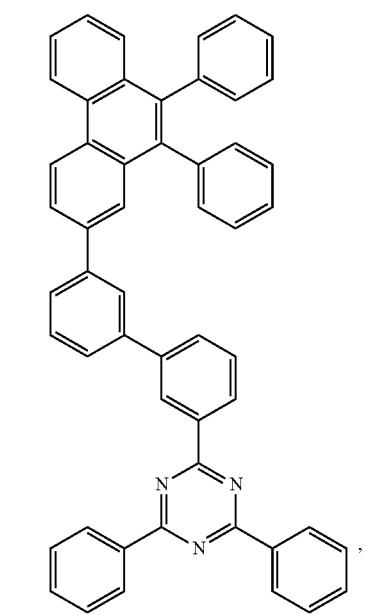
J12
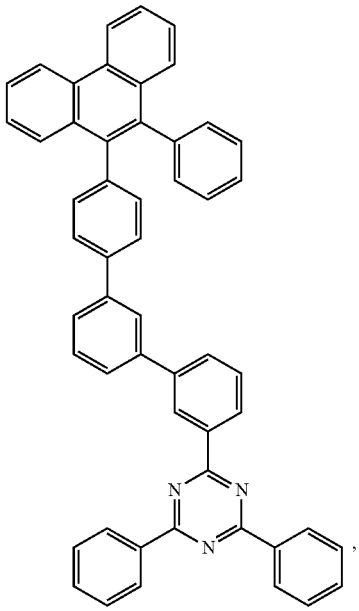
J13
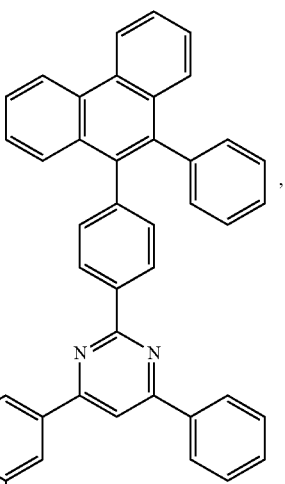
J14
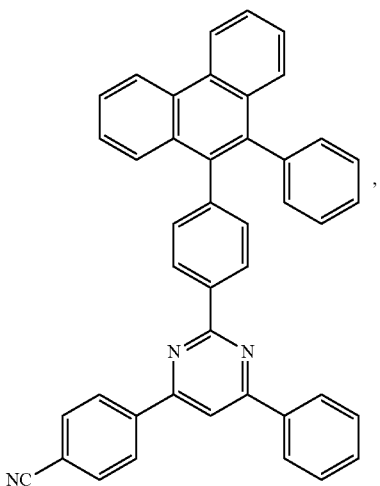

J15
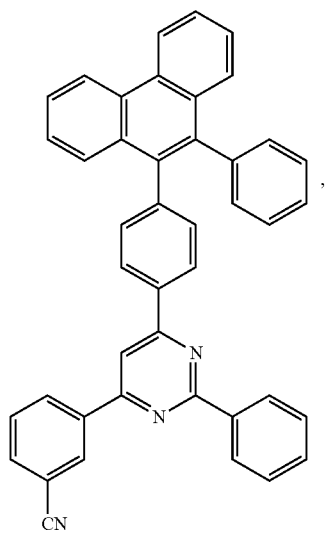
J16
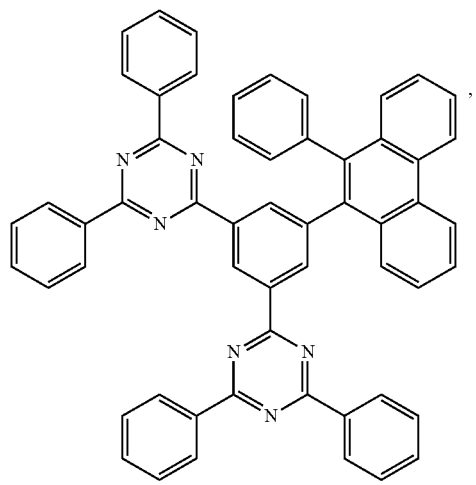
J17
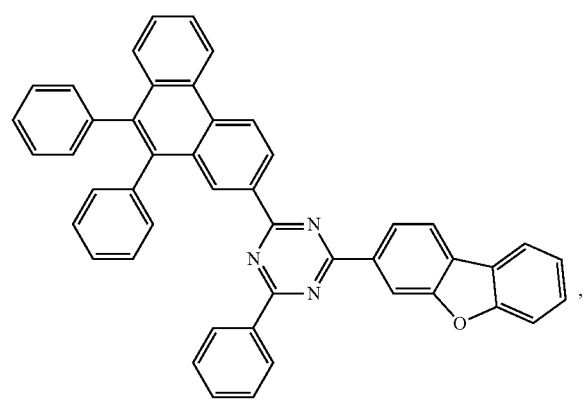
J18
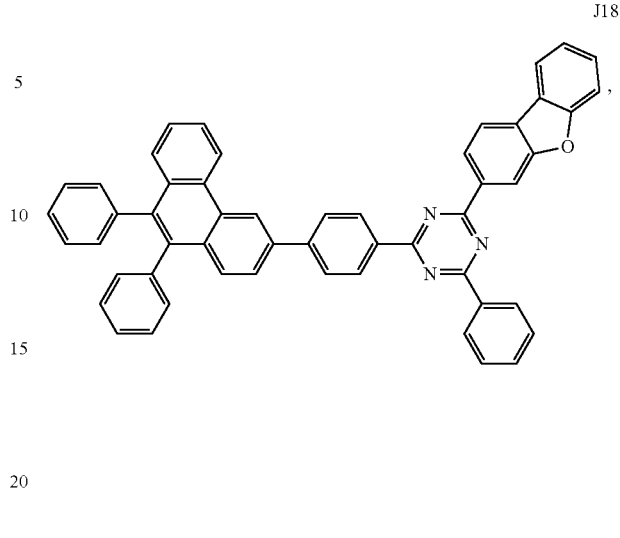
J19
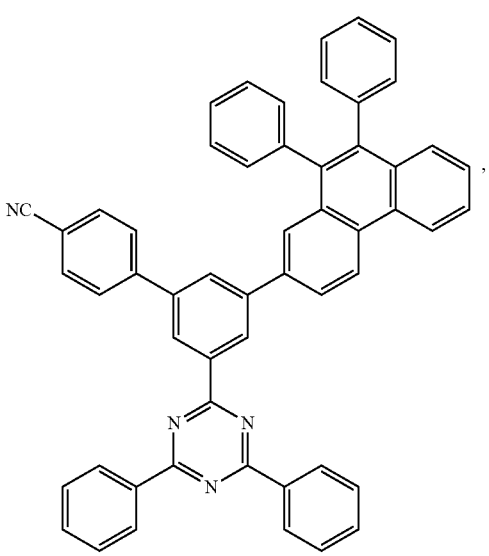
J20
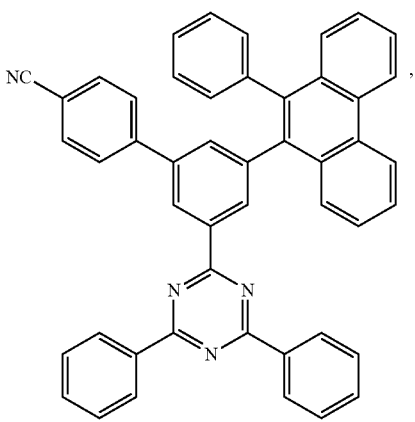

J21
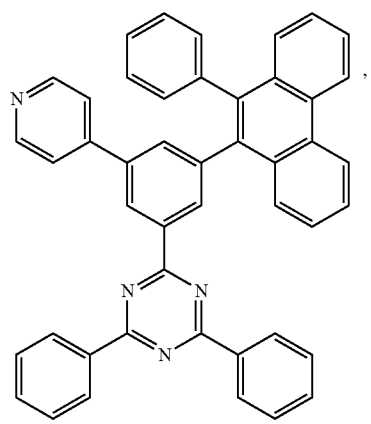
J24
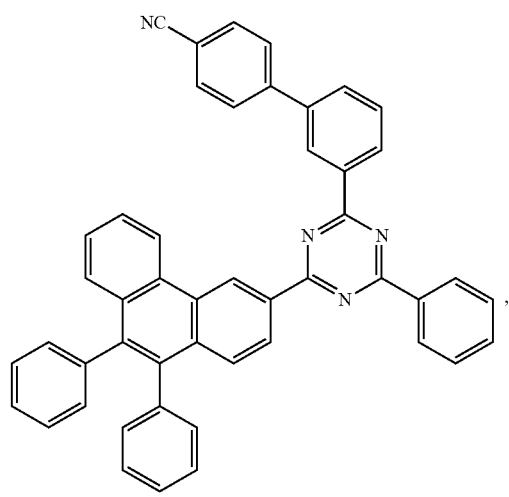
J22
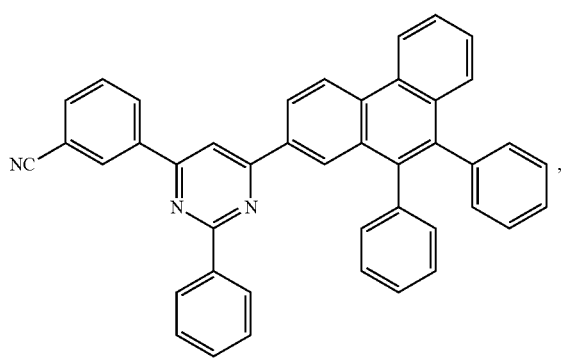
J25
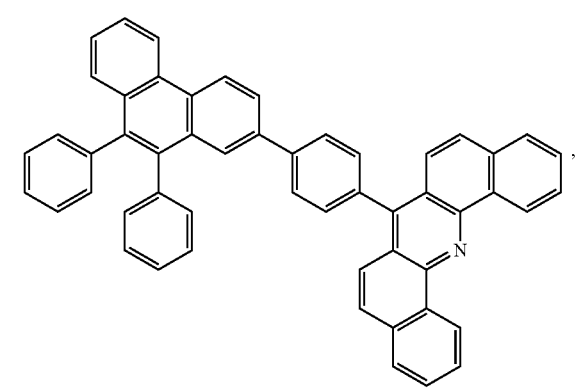
J23
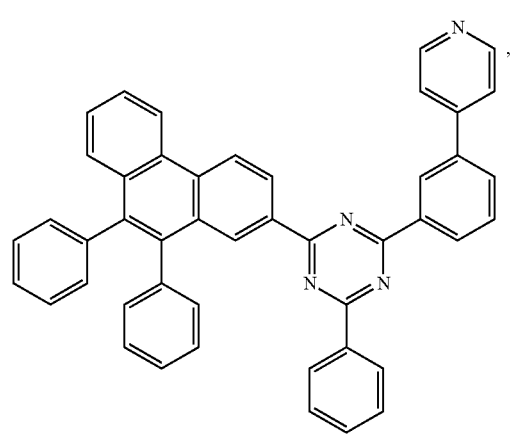
J26
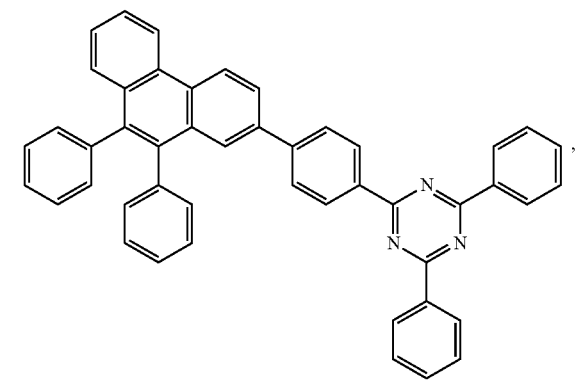

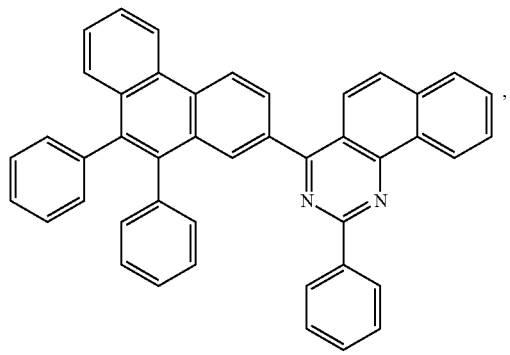
J27
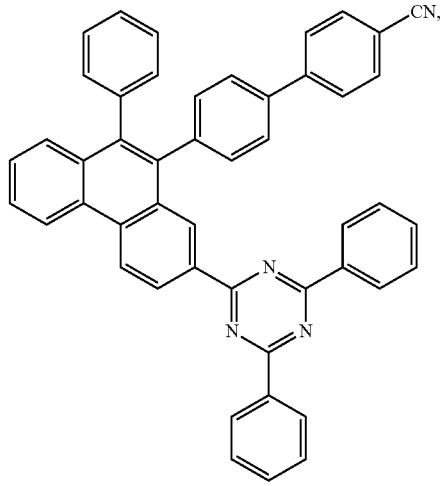
J30
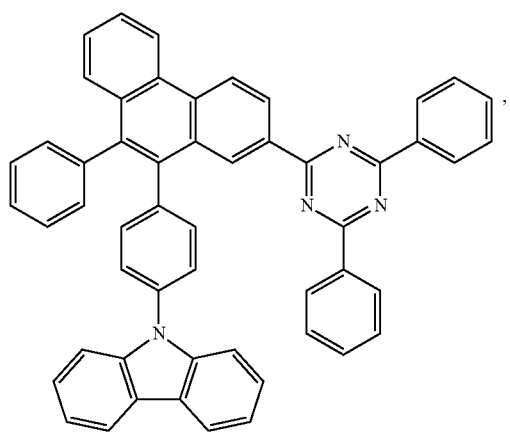
J28
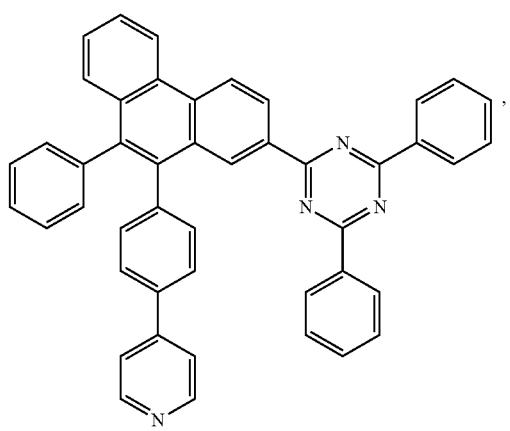
J31
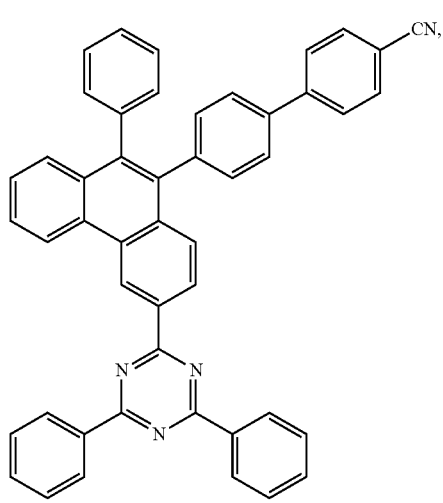
J29
J32

J33
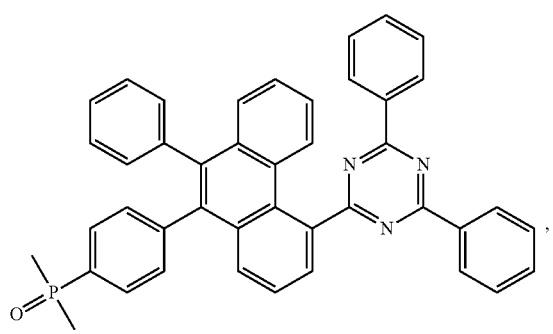
J34
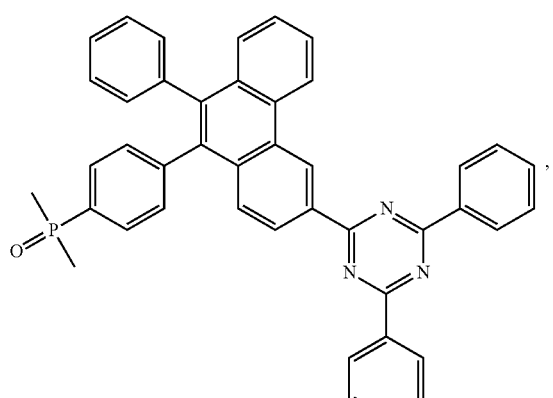
J35
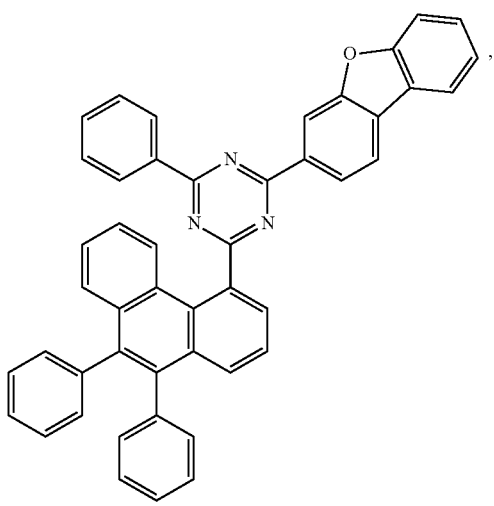
J36
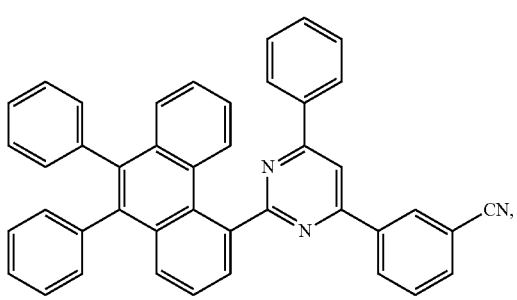
J37
J38
J39
J40

J41
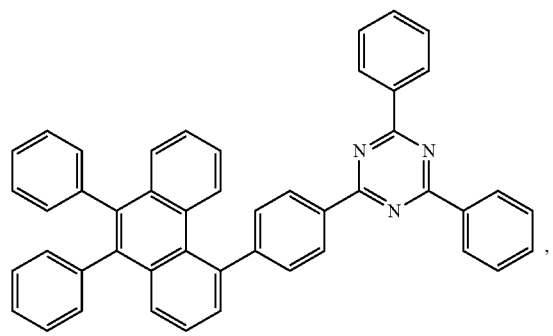
J42
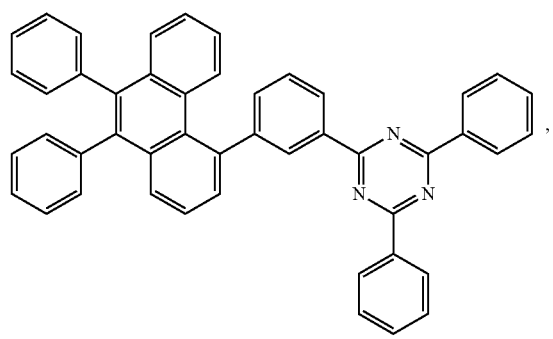
J43
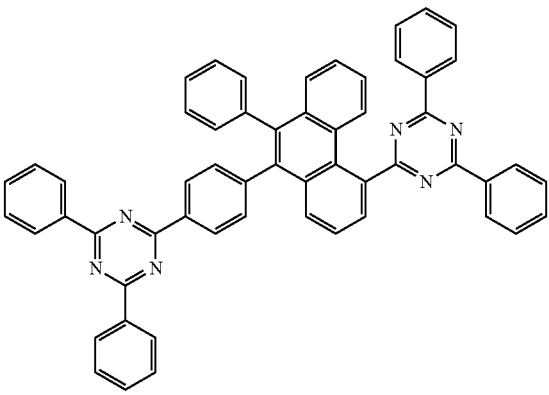
J44
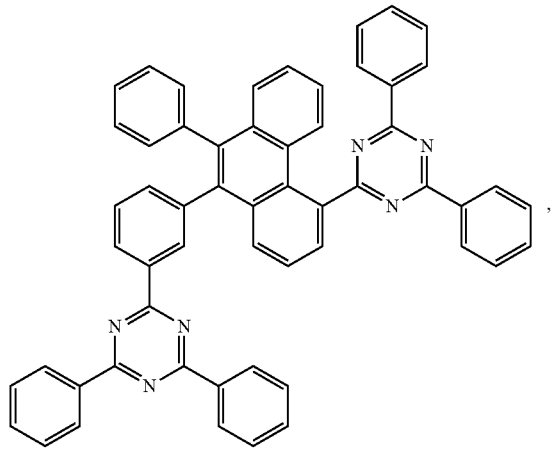
J45
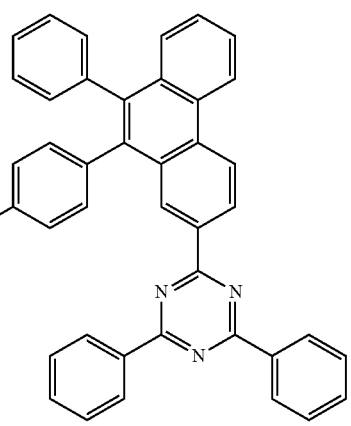
J46
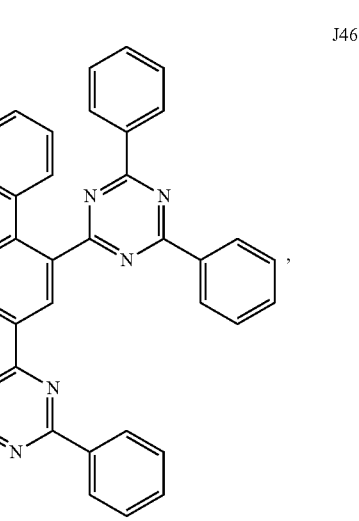
J47
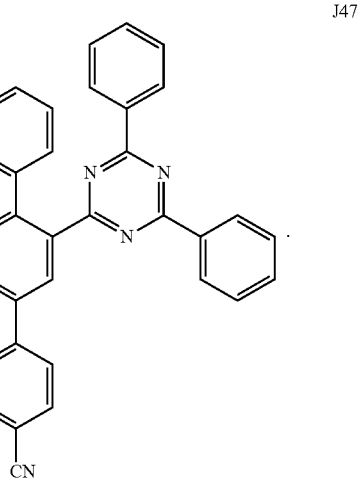

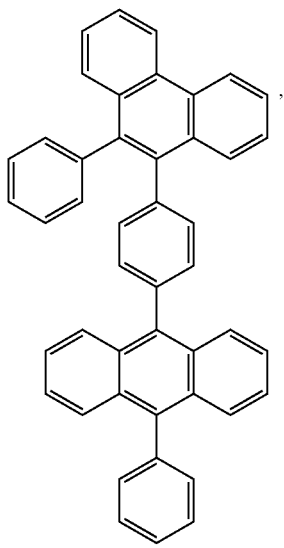
J48
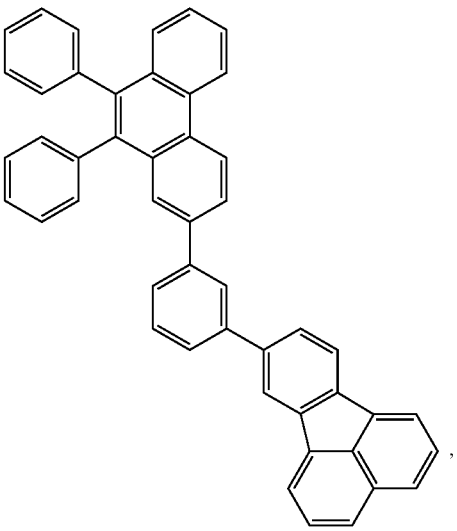
J51
J49
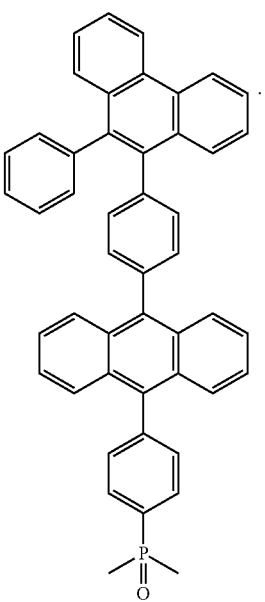
J52
J50

-continued

J53

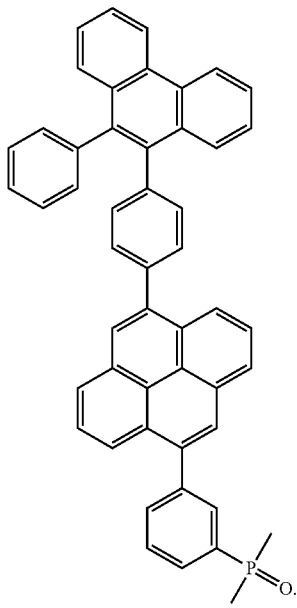

According to an aspect the compound of formula 1 can be used as a matrix material for a dopant material.

According to one embodiment an organic semiconductor layer may comprises at least one compound of formula 1.

According to an aspect the layer material can be an organic semiconductor layer, which is used for an organic electronic device. For example, the organic electronic device can be an OLED or there like.

The compounds represented by formula 1 may have strong electron transport characteristics to increase charge mobility and/or stability and thereby to improve luminance efficiency, voltage characteristics, and/or lifetime characteristics.

The compounds represented by formula 1 may have high electron mobility and a low operating voltage.

In the description the expression "auxiliary ETL" and "first ETL" are synonymously used. ETL means electron transport layer.

The compounds represented by formula 1 and an organic semiconductor layer comprising or consisting of a compound of formula 1 may be non-emissive.

In the context of the present specification the term "non-emissive", "essentially non-emissive" or "non-emitting" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the compound of formula 1 and the organic semiconductor layer comprising or consisting of the compound of formula 1 is essentially non-emissive or non-emitting.

The term "free of", "does not contain", "does not comprise" does not exclude impurities which may be present in the compounds prior to deposition. Impurities have no technical effect with respect to the object achieved by the present invention.

The operating voltage, also named U, is measured in Volt (V) at 10 milliAmpere per square be centimeter (mA/cm2).

The candela per Ampere efficiency, also named cd/A efficiency, is measured in candela per ampere at 10 milli-Ampere per square centimeter (mA/cm2).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The rate onset temperature $T_{RO}$ is measured in ° C. and describes the VTE source temperature at which measurable evaporation of a compound commences at a pressure of less than $10^{-5}$ mbar.

The term "OLED", "organic light emitting diode", "organic light emitting device", "organic optoelectronic device" and "organic light-emitting diode" are simultaneously used and have the same meaning.

The term "transition metal" means and comprises any element in the d-block of the periodic table, which comprises groups 3 to 12 elements on the periodic table.

The term "group III to VI metal" means and comprises any metal in groups III to VI of the periodic table.

As used herein, "weight percent", "wt.-%", "percent by weight", "% by weight", and variations thereof refer to a composition, component, substance or agent as the weight of that composition, component, substance or agent of the respective electron transport layer divided by the total weight of the composition thereof and multiplied by 100. It is understood that the total weight percent amount of all components, substances or agents of the respective electron transport layer may be selected such that it does not exceed 100 wt.-%.

As used herein, "volume percent", "vol.-%", "percent by volume", "% by volume", and variations thereof refer to an elemental metal, a composition, component, substance or agent as the volume of that elemental metal, component, substance or agent of the respective electron transport layer divided by the total volume of the respective electron transport layer thereof and multiplied by 100. It is understood that the total volume percent amount of all elemental metal, components, substances or agents of the respective cathode electrode layer may be selected such that it does not exceed 100 vol.-%.

All numeric values are herein assumed to be modified by the term "about", whether or not explicitly indicated. As used herein, the term "about" refers to variation in the numerical quantity that can occur.

Whether or not modified by the term "about", the claims include equivalents to the quantities.

It should be noted that, as used in this specification and the appended claims, the singular forms "a", "an", and "the" include plural referents unless the content clearly dictates otherwise.

It should be noted that, as used in this specification and the appended claims, "*" if not otherwise defined indicates the chemical bonding position.

The anode electrode and cathode electrode may be described as anode electrode/cathode electrode or anode electrode/cathode electrode or anode electrode layer/cathode electrode layer.

According to another aspect, an organic optoelectronic device comprises an anode layer and a cathode layer facing each other and at least one organic semiconductor layer between the anode layer and the cathode layer, wherein the organic semiconductor layer comprises or consists of the compound of formula 1.

According to yet another aspect, a display device comprising the organic electronic device, which can be an organic optoelectronic device, is provided.

In the present specification, when a definition is not otherwise provided, an "alkyl group" may refer to an aliphatic hydrocarbon group. The alkyl group may refer to "a saturated alkyl group" without any double bond or triple bond. The alkyl group may be a linear, cyclic or branched alkyl group.

The term "alkyl group" includes $C_1$ to $C_{16}$ alkyl, $C_3$ to $C_{16}$ branched alkyl, and $C_3$ to $C_{16}$ cyclic alkyl.

The alkyl group may be a $C_1$ to $C_{16}$ alkyl group, or preferably a $C_1$ to $C_{12}$ alkyl group. More specifically, the alkyl group may be a $C_1$ to $C_{14}$ alkyl group, or preferably a $C_1$ to $C_{10}$ alkyl group or a $C_1$ to $C_6$ alkyl group. For example, a $C_1$ to $C_4$ alkyl group comprises 1 to 4 carbons in alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a tert-butyl group, a pentyl group, a hexyl group, a cyclopropyl group, a cyclobutyl group, a cyclopentyl group, a cyclohexyl group, and the like.

In the present specification "arylene group" may refer to a group comprising at least one hydrocarbon aromatic moiety, and all the elements of the hydrocarbon aromatic moiety may have p-orbitals which form conjugation, for example a phenyl group, a naphthyl group, an anthracenyl group, a phenanthrenyl group, a pyrenyl group, a fluorenyl group and the like, if not otherwise defined.

The terms "heteroarylene", "heteroaryl" may refer to aromatic heterocycles with at least one heteroatom, and all the elements of the hydrocarbon heteroaromatic moiety may have p-orbitals which form conjugation, if not otherwise defined.

The terms "heteroarylene", "heteroaryl" may refer to antiaromatic heterocycles with at least one heteroatom, for examples azepines.

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a <1 mm hole is pierced into the lid).

According to another embodiment the compound of formula 1 may have a melting point of about ≥305° C. and about ≤400° C., preferably about ≥310° C. and about ≤370° C., further preferred about ≥315° C. and about ≤360° C.

Glass Transition Temperature

The glass transition temperature is measured under nitrogen and using a heating rate of 10 K per min in a Mettler Toledo DSC 822e differential scanning calorimeter as described in DIN EN ISO 11357, published in March 2010.

According to another embodiment the compound of formula 1 may have a glass transition temperature Tg of about ≥115° C. and about ≤280° C., preferably about ≥130° C. and about ≤250° C., further preferred about ≥135° C. and about ≤220° C., in addition preferred about ≥140° C. and about ≤190° C.

Rate Onset Temperature

The rate onset temperature $T_{RO}$ is determined by loading 100 mg compound into a VTE source. As VTE source a point source for organic materials is used as supplied by Kurt J. Lesker Company (www.lesker.com) or CreaPhys GmbH (http://www.creaphys.com). The VTE source is heated at a constant rate of 15 K/min at a pressure of less than $10^{-5}$ mbar and the temperature inside the source measured with a thermocouple. Evaporation of the compound is detected with a QCM detector which detects deposition of the compound on the quartz crystal of the detector. The deposition rate on the quartz crystal is measured in Angstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200° C. to 260° C. If the rate onset temperature is below 200° C. the evaporation may be too rapid and therefore difficult to control. If the rate onset temperature is above 260° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

According to another embodiment the compound of formula 1 may have a rate onset temperature $T_{RO}$ of about ≥200° C. and about ≤350° C., preferably about ≥220° C. and about ≤350° C., further preferred about ≥250° C. and about ≤300° C.

Dipole Moment

The dipole moment $|\vec{\mu}|$ of a molecule containing N atoms is given by:

$$\vec{\mu} = \sum_i^N q_i \vec{r}_i$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method. The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy may be selected to determine the bond lengths of the molecules.

According to one embodiment the compounds according to formula 1 may have a dipole moment (Debye) in the range from about ≥0.1 to about ≤1.50, preferably from about ≥0.3 to about ≤1.

Calculated HOMO and LUMO

The HOMO and LUMO are calculated with the program package TURBOMOLE V6.5. The optimized geometries and the HOMO and LUMO energy levels of the molecular structures are determined by applying the hybrid functional B3LYP with a 6-31G* basis set in the gas phase. If more than one conformation is viable, the conformation with the lowest total energy may be selected.

According to one embodiment the compounds according to formula 1 may have a HOMO energy level (eV) in the range from about −6.00 eV to about −4.50 eV, preferably from about −5.85 eV to about −5.00 eV.

According to one embodiment the compounds according to formula 1 may have a LUMO energy level (eV) in the range from about −2.30 eV to about −1.70 eV, preferably from about −1.8 eV to about −2.2 eV.

Molar Mass

The molar mass (MM) of a compound_in g/mol is given by the sum of the standard atomic weight (namely, the standard relative atomic mass) of the atoms which form the compound multiplied by the molar mass constant, $M_u$. $M_u$ is $1 \times 10^{-3}$ kg/mol=1 g/mol.

According to one embodiment the compounds according to formula 1 may have a molar mass (g/mol) in the range from about 600 g/mol, to about 1800 g/mol, preferably from about 650 to about 1600 g/mol, further preferred from about 700 g/mol, to about 1500 g/mol.

Technical Effect

It has surprisingly been found by the inventors that compounds of formula 1 with the structure element 4:

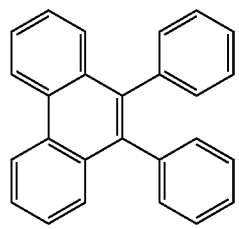

(4)

have an improved glass transition temperature compared to the same compounds having instead of the structure element 4 the structure element 5:

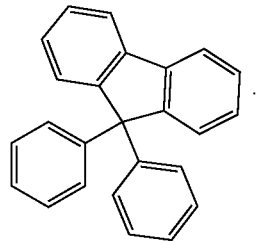

(5)

The higher glass transition temperature of the compounds according to formula 1 have the benefit for improved properties in high temperature applications, as the morphology of the organic semiconductor layer is less likely to deteriorate.

Furthermore, the compounds according to formula 1 and the organic electronic devices comprising at least one compound of formula 1 solve the problem underlying the present invention by being superior over the organic electroluminescent devices and compounds known in the art, in particular with respect to operating voltage, which is important for reducing power consumption and increasing battery life, for example of a mobile display device. At the same time the cd/A efficiency, also referred to as current efficiency is kept at a similar or even improved level. Long lifetime at high current density is important for the longevity of a device which is run at high brightness.

The inventors have surprisingly found that particular good performance can be achieved when using the organic electroluminescent device as a fluorescent blue device.

The specific arrangements mentioned herein as preferred were found to be particularly advantageous.

Likewise, some compounds falling within the scope of the broadest definition of the present invention have surprisingly be found to be particularly well performing with respect to the mentioned property of glass transition temperature, rate onset temperature and/or operating voltage in organic electronic devices. These compounds are discussed herein to be particularly preferred.

Further an organic optoelectronic device having high efficiency and/or long lifetime may be realized.

Anode

A material for the anode may be a metal or a metal oxide, or an organic material, preferably a material with work function above about 4.8 eV, more preferably above about 5.1 eV, most preferably above about 5.3 eV. Preferred metals are noble metals like Pt, Au or Ag, preferred metal oxides are transparent metal oxides like ITO or IZO which may be advantageously used in bottom-emitting OLEDs having a reflective cathode.

In devices comprising a transparent metal oxide anode or a reflective metal anode, the anode may have a thickness from about 50 nm to about 100 nm, whereas semitransparent metal anodes may be as thin as from about 5 nm to about 15 nm, and non-transparent metal anodes may have a thickness from about 15 nm to about 150 nm.

Hole Injection Layer (HIL)

The hole injection layer may improve interface properties between the anode and an organic material used for the hole transport layer, and is applied on a non-planarized anode and thus may planarize the surface of the anode. For example, the hole injection layer may include a material having a median value of the energy level of its highest occupied molecular orbital (HOMO) between the work function of the anode material and the energy level of the HOMO of the hole transport layer, in order to adjust a difference between the work function of the anode and the energy level of the HOMO of the hole transport layer.

When the hole transport region comprises a hole injection layer 36, the hole injection layer may be formed on the anode by any of a variety of methods, for example, vacuum deposition, spin coating, casting, Langmuir-Blodgett (LB) method, or the like.

When hole injection layer is formed using vacuum deposition, vacuum deposition conditions may vary depending on the material that is used to form the hole injection layer, and the desired structure and thermal properties of the hole injection layer to be formed and for example, vacuum deposition may be performed at a temperature of about 100° C. to about 500° C., a pressure of about $10^{-6}$ Pa to about $10^{-1}$ Pa, and a deposition rate of about 0.1 to about 10 nm/sec, but the deposition conditions are not limited thereto.

When the hole injection layer is formed using spin coating, the coating conditions may vary depending on the material that is used to form the hole injection layer, and the desired structure and thermal properties of the hole injection layer to be formed. For example, the coating rate may be in the range of about 2000 rpm to about 5000 rpm, and a temperature at which heat treatment is performed to remove a solvent after coating may be in a range of about 80° C. to about 200° C., but the coating conditions are not limited thereto.

The hole injection layer may further comprise a p-dopant to improve conductivity and/or hole injection from the anode.

p-Dopant

In another aspect, the p-dopant may be homogeneously dispersed in the hole injection layer.

In another aspect, the p-dopant may be present in the hole injection layer in a higher concentration closer to the anode and in a lower concentration closer to the cathode.

The p-dopant may be one of a quinone derivative or a radialene compound but not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), 4,4′,4″-((1E,1′E,1″E)-cyclopropane-1,2,3-triylidenetris(cyanomethanylylidene))-tris(2,3,5,6-tetrafluorobenzonitrile).

According to another embodiment, the device comprising a compound of formula 1 may further comprise a layer comprising a radialene compound and/or a quinodimethane compound.

In another embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have formula (XX) and/or the quinodimethane compound may have formula (XXIa) or (XXIb):

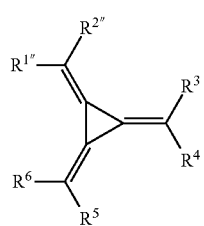

(XX)

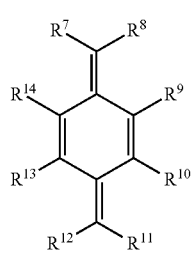

(XXIa)

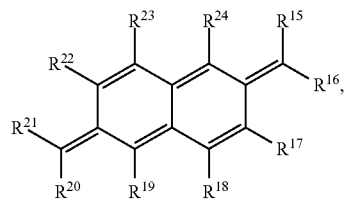

(XXIb)

wherein $R^{1''}$, $R^{2''}$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from an electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and electron withdrawing groups. Electron withdrawing group that can be suitable used are above mentioned.

Hole Transport Layer (HTL)

Conditions for forming the hole transport layer and the electron blocking layer may be defined based on the above-described formation conditions for the hole injection layer.

A thickness of the hole transport part of the charge transport region may be from about 10 nm to about 1000 nm, for example, about 10 nm to about 100 nm. When the hole transport part of the charge transport region comprises the hole injection layer and the hole transport layer, a thickness of the hole injection layer may be from about 10 nm to about 1000 nm, for example about 10 nm to about 100 nm and a thickness of the hole transport layer may be from about 5 nm to about 200 nm, for example about 10 nm to about 150 nm. When the thicknesses of the hole transport part of the charge transport region, the HIL, and the HTL are within these ranges, satisfactory hole transport characteristics may be obtained without a substantial increase in operating voltage.

Hole transport matrix materials used in the hole transport region are not particularly limited. Preferred are covalent compounds comprising a conjugated system of at least 6 delocalized electrons, preferably organic compounds comprising at least one aromatic ring, more preferably organic compounds comprising at least two aromatic rings, even more preferably organic compounds comprising at least three aromatic rings, most preferably organic compounds comprising at least four aromatic rings. Typical examples of hole transport matrix materials which are widely used in hole transport layers are polycyclic aromatic hydrocarbons, triarylene amine compounds and heterocyclic aromatic compounds.

Suitable ranges of frontier orbital energy levels of hole transport matrices useful in various layer of the hole transport region are well-known. In terms of the redox potential of the redox couple HTL matrix/cation radical of the HTL matrix, the preferred values (if measured for example by cyclic voltammetry against ferrocene/ferrocenium redox couple as reference) may be in the range 0.0-1.0 V, more preferably in the range 0.2-0.7 V, even more preferably in the range 0.3-0.5 V.

Buffer Layer

The hole transport part of the charge transport region may further include a buffer layer.

Buffer layer that can be suitable used are disclosed in U.S. Pat. Nos. 6,140,763, 6,614,176 and in US2016/248022.

The buffer layer may compensate for an optical resonance distance of light according to a wavelength of the light emitted from the EML, and thus may increase efficiency.

Emission Layer (EML)

The emission layer may be formed on the hole transport region by using vacuum deposition, spin coating, casting, LB method, or the like. When the emission layer is formed using vacuum deposition or spin coating, the conditions for deposition and coating may be similar to those for the formation of the hole injection layer, though the conditions for the deposition and coating may vary depending on the material that is used to form the emission layer. The emission layer may include an emitter host (EML host) and an emitter dopant (further only emitter).

A thickness of the emission layer may be about 100 Å to about 1000 Å, for example about 200 Å to about 600 Å. When the thickness of the emission layer is within these ranges, the emission layer may have improved emission characteristics without a substantial increase in operating voltage.

Emitter Host

According to another embodiment, the emission layer comprises compound of formula 1 as emitter host.

The emitter host compound has at least three aromatic rings, which are independently selected from carbocyclic rings and heterocyclic rings.

Other compounds that can be used as the emitter host is an anthracene matrix compound represented by formula 400 below:

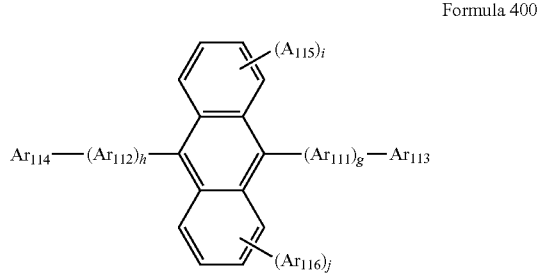

Formula 400

In formula 400, $Ar_{111}$ and $Ar_{112}$ may be each independently a substituted or unsubstituted $C_6$-$C_{60}$ arylene group; $Ar_{113}$ to $Ar_{116}$ may be each independently a substituted or unsubstituted $C_1$-$C_{10}$ alkyl group or a substituted or unsubstituted $C_6$-$C_{60}$ arylene group; and g, h, i, and j may be each independently an integer from 0 to 4.

In some embodiments, $Ar_{111}$ and $Ar_{112}$ in formula 400 may be each independently one of a phenylene group, a naphthalene group, a phenanthrenylene group, or a pyrenylene group; or a phenylene group, a naphthalene group, a phenanthrenylene group, a fluorenyl group, or a pyrenylene group, each substituted with at least one of a phenyl group, a naphthyl group, or an anthryl group.

In formula 400, g, h, i, and j may be each independently an integer of 0, 1, or 2.

In formula 400, $Ar_{113}$ to $Ar_{116}$ may be each independently one of a $C_1$-$C_{10}$ alkyl group substituted with at least one of a phenyl group, a naphthyl group, or an anthryl group;

a phenyl group, a naphthyl group, an anthryl group, a pyrenyl group, a phenanthrenyl group, or a fluorenyl group;

a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group

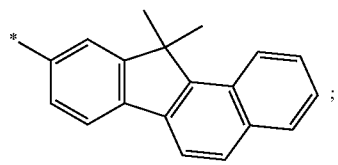 [SMILES: *c1ccc2c(c1)C(C)(C)c1c-2ccc2ccccc12]

or formulas 7 or 8

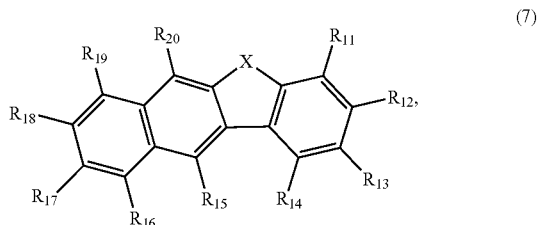

(7)

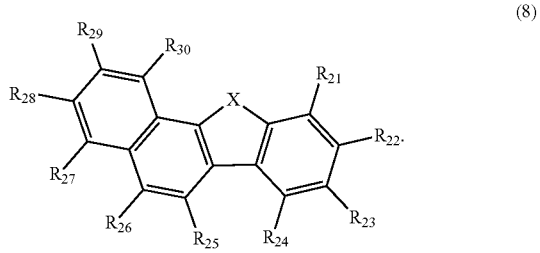

(8)

Wherein in the formulas 7 and 8, X may be selected form an oxygen atom and a sulfur atom, but embodiments of the invention are not limited thereto.

In the formula 7, any one of $R_{11}$ to $R_{14}$ is used for bonding to $Ar_{111}$. $R_{11}$ to $R_{14}$ that are not used for bonding to $Ar_{111}$ and $R_{15}$ to $R_{20}$ are the same as $R_1$ to $R_8$.

In the formula 8, any one of $R_{21}$ to $R_{24}$ is used for bonding to $Ar_{111}$. $R_{21}$ to $R_{24}$ that are not used for bonding to $Ar_{111}$ and $R_{25}$ to $R_{30}$ are the same as $R_1$ to $R_8$.

Preferably, the EML host comprises between one and three heteroatoms selected from the group comprising of N, O or S. More preferred the EML host comprises one heteroatom selected from S or O.

Emitter Dopant

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The emitter may be a red, green, or blue emitter.

The dopant may be a fluorescent dopant, for example ter-fluorene, the structures are shown below. 4.4'-bis(4-diphenyl aminostyryl)biphenyl (DPAVBI, 2,5,8,11-tetra-tert-butyl perylene (TBPe), and Compound 8 below are examples of fluorescent blue dopants.

Compound 8

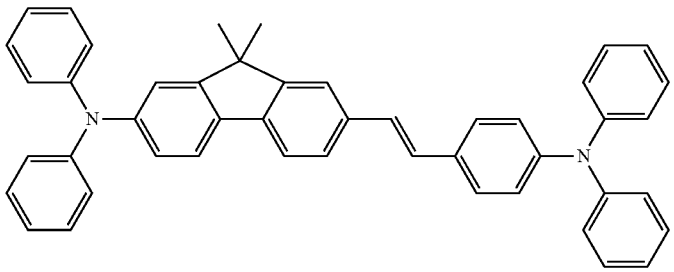

The dopant may be a phosphorescent dopant, and examples of the phosphorescent dopant may be an organic metal compound comprising Ir, Pt, Os, Ti, Zr, Hf, Eu, Tb, Tm, Fe, Co, Ni, Ru, Rh, Pd, or a combination thereof. The phosphorescent dopant may be, for example a compound represented by formula Z, but is not limited thereto:

$$J_2MX \qquad (Z).$$

In formula Z, M is a metal, and J and X are the same or different, and are a ligand to form a complex compound with M.

The M may be, for example Ir, Pt, Os, Ti, Zr, Hf, Eu, Tb, Tm, Fe, Co, Ni, Ru, Rh, Pd or a combination thereof, and the J and X may be, for example a bidendate ligand.

One or more emission layers may be arranged between the anode and the cathode. To increase overall performance, two or more emission layers may be present.

Charge Generation Layer

A charge generation layer (also named CGL) may be arranged between the first and the second emission layer, and second and third emission layer, if present. Typically, the CGL comprises a n-type charge generation layer (also named n-CGL or electron generation layer) and a p-type charge generation layer (also named p-CGL or hole generation layer). An interlayer may be arranged between the n-type CGL and the p-type CGL.

In one aspect, the n-type CGL may comprise a compound of formula 1. The n-type CGL further comprises a metal, metal salt or organic metal complex, preferably a metal. The metal may be selected from an alkali, alkaline earth or rare earth metal.

The p-type CGL may comprise a dipyrazino[2,3-f:2',3'-h]quinoxaline, a quinone compound or a radialene compound, preferably dipyrazino[2,3-f:2',3'-h]quinoxaline-2,3,6,7,10,11-hexacarbonitrile or a compound or formula (XX) and/or a compound of formula (XXIa) or (XXIb) as mentioned above.

In another aspect, the n-type and p-type CGL are in direct contact.

Electron Transport Layer (ETL)

According to another embodiment, the organic semiconductor layer that comprises compound of formula 1 is an electron transport layer. In another embodiment the electron transport layer may consist of compound of formula 1.

For example, an organic light emitting diode according to an embodiment of the present invention comprises at least one electron transport layer, and in this case, the electron transport layer comprises at least one compound of formula 1, or preferably of at least one compound of formulae J1 to J53, preferably of J1 or J2.

In another embodiment, the organic electronic device comprises an electron transport region of a stack of organic layers formed by two or more electron transport layers, wherein at least one electron transport layer comprises a compound of formula 1.

The electron transport layer may include one or two or more different electron transport compounds.

According to another embodiment, a first electron transport layer (ETL1) comprises at least one compound of formula 1 according to the invention and a second electron transport layer (ETL2) comprises a matrix compound, which may be selected different to the compound of formula 1 according to the invention, and may be selected from:
- an anthracene based compound or a hetero substituted anthracene based compound, preferably 2-(4-(9,10-di(naphthalen-2-yl)anthracene-2-yl)phenyl)-1-phenyl-1H-benzo[d]imidazole and/or N4,N4''-di(naphthalen-1-yl)-N4,N4''-diphenyl-[1,1': 4',1''-terphenyl]-4,4''-diamine and/or
- a triazine based compound, preferably the triazine based compound comprising aryl and/or heteroaryl substituents, preferably aryl substituents, and/or
- a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide; or
- a substituted phenanthroline compound, preferably 2,4,7,9-tetraphenyl-1,10-phenanthroline or 2,9-di(biphenyl-4-yl)-4,7-diphenyl-1,10-phenanthroline.

According to another embodiment a first electron transport layer comprises at least one compound of formula 1 according to the invention and a second electron transport layer comprises a matrix compound, which may be selected different to the compound of formula 1 according to the invention, and may be selected from a phosphine oxide based compound, preferably (3-(dibenzo[c,h]acridin-7-yl)phenyl)diphenylphosphine oxide and/or phenyl bis(3-(pyren-1-yl)phenyl)phosphine oxide and/or 3-Phenyl-3H-benzo[b]dinaphtho[2,1-d:1',2'-f]phosphepine-3-oxide.

The first electron transport layer may also be described as auxiliary electron transport layer or a hole blocking layer.

According to another embodiment, a first and a second electron transport layers comprise compound of formula 1, wherein the compound of formula 1 is not selected the same.

According to another embodiment, a second electron transport layer (ETL2) comprises at least one compound of formula 1 according to the invention and a first electron transport layer (ETL1) comprises an azine compound, The thickness of the electron transport layer may be from about 0.5 nm to about 100 nm, for example about 2 nm to about 40 nm, preferably 2 to 10 nm. The thickness of the first electron transport layer may be from about 0.5 nm to about 100 nm, for example about 2 nm to about 40 nm, preferably 2 to 10 nm.

A thickness of an optional second electron transport layer may be about 1 nm to about 100 nm, for example about 2 nm to about 50 nm, preferably 10 to 40 nm. When the thickness of the electron transport layer is within these ranges, the electron transport layer may have satisfactory electron transporting ability without a substantial increase in operating voltage.

The electron transport layer may further comprise a monovalent or divalent metal halide or an organic monovalent or divalent metal complex, preferably an alkali halide and/or alkali organic complex.

According to another embodiment, the first and second electron transport layers comprise compound of formula 1, wherein the second electron transport layer further comprises an alkali halide and/or alkali organic complex.

Alkali Halide

Alkali halides, also known as alkali metal halides, are the family of inorganic compounds with the chemical formula MX, where M is an alkali metal and X is a halogen.

M can be selected from Li, Na, Potassium, Rubidium and Cesium.

X can be selected from F, Cl, Br and J.

According to various embodiments of the present invention a lithium halide may be preferred. The lithium halide can be selected from the group comprising LiF, LiCl, LiBr and LiJ. However, most preferred is LiF.

The alkali halide is essentially non-emissive or non-emissive.

Alkali Organic Complex

The alkali organic complex comprises an alkali metal and at least one organic ligand. The alkali metal is preferably selected from lithium.

According to various embodiments of the present invention the organic ligand of the lithium organic complex is a quinolate, a borate, a phenolate, a pyridinolate or a Schiff base ligand;

preferably the lithium quinolate complex has the formula III, IV or V:

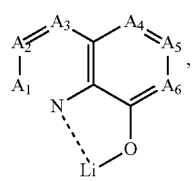

(III)

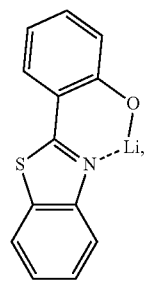

(IV)

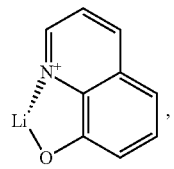

(V)

wherein
  $A_1$ to $A_6$ are same or independently selected from CH, CR, N and O;
  R is same or independently selected from hydrogen, halogen, alkyl or arylene or heteroarylene with 1 to 20 carbon atoms; and more preferred A1 to A6 are CH;
  preferably the borate based organic ligand is a tetra(1H-pyrazol-1-yl)borate;
  preferably the phenolate is a 2-(pyridin-2-yl)phenolate, a 2-(diphenylphosphoryl)phenolate, an imidazol phenolates, or 2-(pyridin-2-yl)phenolate and more preferred 2-(1-phenyl-1H-benzo[d]imidazol-2-yl)phenolate;
  preferably the pyridinolate is a 2-(diphenylphosphoryl)pyridin-3-olate.

According to various embodiments of the present invention the organic ligand of the alkali organic complex, preferably of a lithium organic complex, can be a quinolate. Quinolates that can be suitable used are disclosed in WO 2013079217 A1 and incorporated by reference.

According to various embodiments of the present invention the organic ligand of the lithium organic complex can be a borate based organic ligand, Preferably the lithium organic complex is a lithium tetra(1H-pyrazol-1-yl)borate. Borate based organic ligands that can be suitable used are disclosed in WO 2013079676 A1 and incorporated by reference.

According to various embodiments of the present invention the organic ligand of the lithium organic complex can be a phenolate ligand, Preferably the lithium organic complex is a lithium 2-(diphenylphosphoryl)phenolate. Phenolate ligands that can be suitable used are disclosed in WO 2013079678 A1 and incorporated by reference.

Further, phenolate ligands can be selected from the group of pyridinolate, preferably 2-(diphenylphosphoryl)pyridin-3-olate. Pyridine phenolate ligands that can be suitable used are disclosed in JP 2008195623 and incorporated by reference.

In addition, phenolate ligands can be selected from the group of imidazol phenolates, preferably 2-(1-phenyl-1H-benzo[d]imidazol-2-yl)phenolate. Imidazol phenolate ligands that can be suitable used are disclosed in JP 2001291593 and incorporated by reference.

Also, phenolate ligands can be selected from the group of oxazol phenolates, preferably 2-(benzo[d]oxazol-2-yl)phenolate. Oxazol phenolate ligands that can be suitable used are disclosed in US 20030165711 and incorporated by reference.

The alkali organic complex may be essentially non-emissive.

Electron Injection Layer (EIL)

According to another aspect of the invention, the organic electroluminescent device may further comprise an electron injection layer between the electron transport layer (first-ETL) and the cathode.

The electron injection layer (EIL) may facilitate injection of electrons from the cathode.

According to another aspect of the invention, the electron injection layer comprises:

(i) an electropositive metal selected from alkali metals, alkaline earth metals and rare earth metals in substantially elemental form, preferably selected from Li, Na, K, Rb, Cs, Mg, Ca, Sr, Ba, Eu and Yb, more preferably from Li, Na, Mg, Ca, Sr and Yb, even more preferably from Li and Yb, most preferably Yb; and/or (ii) an alkali metal complex and/or alkali metal salt, preferably the Li complex and/or salt, more preferably a Li quinolinolate, even more preferably a lithium 8-hydroxyquinolinolate, most preferably the alkali metal salt and/or complex of the second electron transport layer (second-ETL) is identical with the alkali metal salt and/or complex of the injection layer.

The electron injection layer may include at least one selected from LiF, NaCl, CsF, $Li_2O$, and BaO.

A thickness of the EIL may be from about 0.1 nm to about 10 nm, or about 0.3 nm to about 9 nm. When the thickness of the electron injection layer is within these ranges, the electron injection layer may have satisfactory electron injection ability without a substantial increase in operating voltage.

The electron injection layer may comprise a compound of formula 1.

Cathode

A material for the cathode may be a metal, an alloy, or an electrically conductive compound that have a low work function, or a combination thereof. Specific examples of the material for the cathode may be lithium (Li), magnesium (Mg), aluminum (Al), aluminum-lithium (Al—Li), calcium (Ca), magnesium-indium (Mg—In), magnesium-silver (Mg—Ag), silver (Ag) etc. In order to manufacture a top-emission light-emitting device having a reflective anode deposited on a substrate, the cathode may be formed as a light-transmissive electrode from, for example, indium tin oxide (ITO), indium zinc oxide (IZO) or silver (Ag).

In devices comprising a transparent metal oxide cathode or a reflective metal cathode, the cathode may have a thickness from about 50 nm to about 100 nm, whereas semitransparent metal cathodes may be as thin as from about 5 nm to about 15 nm.

Substrate

A substrate may be further disposed under the anode or on the cathode. The substrate may be a substrate that is used in a general organic light emitting diode and may be a glass substrate or a transparent plastic substrate with strong mechanical strength, thermal stability, transparency, surface smoothness, ease of handling, and water resistance.

Hereinafter, the embodiments are illustrated in more detail with reference to examples. However, the present disclosure is not limited to the following examples.

DESCRIPTION OF THE DRAWINGS

These and/or other aspects and advantages of the present invention will become apparent and more readily appreciated from the following description of the exemplary embodiments, taken in conjunction with the accompanying drawings, of which.

Figure 1:
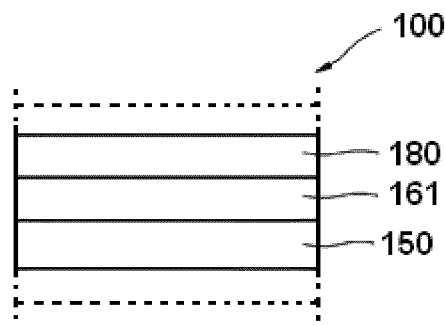
FIG. 1 is a schematic sectional view of an organic light-emitting diode (OLED), according to an exemplary embodiment of the present invention with an emission layer, one electron transport layer and an electron injection layer.

Reference will now be made in detail to the exemplary aspects, examples of which are illustrated in the accompanying drawings, wherein like reference numerals refer to the like elements throughout. The exemplary embodiments are described below, in order to explain the aspects, by referring to the figures.

Herein, when a first element is referred to as being formed or disposed "on" a second element, the first element can be disposed directly on the second element, or one or more other elements may be disposed there between. When a first element is referred to as being formed or disposed "directly on" a second element, no other elements are disposed there between.

The term "contacting sandwiched" refers to an arrangement of three layers whereby the layer in the middle is in direct contact with the two adjacent layers.

The organic light emitting diodes according to an embodiment of the present invention may include a hole transport region; an emission layer; and a first electron transport layer comprising a compound according to formula 1.

FIG. 1 is a schematic sectional view of an organic light-emitting diode 100, according to an exemplary embodiment of the present invention. The OLED 100 comprises an emission layer 150, an electron transport layer (ETL) 161 comprising compound of formula 1 and an electron injection layer 180, whereby the first electron transport layer 161 is disposed directly on the emission layer 150 and the electron injection layer 180 is disposed directly on the first electron transport layer 161.

Figure 2:
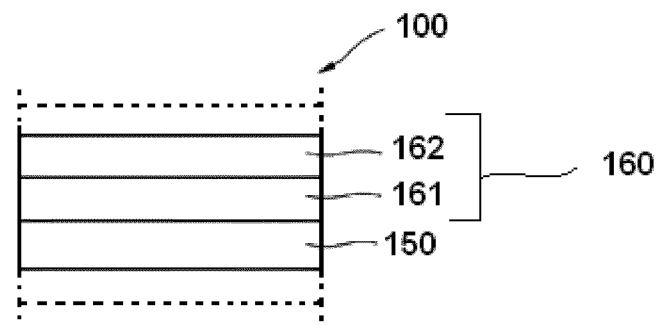
FIG. 2 is a schematic sectional view of an organic light-emitting diode (OLED), according to an exemplary embodiment of the present invention with an emission layer and two electron transport layers.

FIG. 2 is a schematic sectional view of an organic light-emitting diode 100, according to an exemplary embodiment of the present invention. The OLED 100 comprises an emission layer 150 and an electron transport layer stack (ETL) 160 comprising a first electron transport layer (ETL1) 161 comprising compound of formula 1 and a second electron transport layer (ETL2) 162, whereby the second electron transport layer 162 is disposed directly on the first electron transport layer 161. Alternatively, the electron transport layer stack (ETL) 160 comprises a first electron transport layer 161 and a second electron transport layer 162 comprising a compound of formula 1, whereby the second electron transport layer 162 is disposed directly on the first electron transport layer 161.

Figure 3:
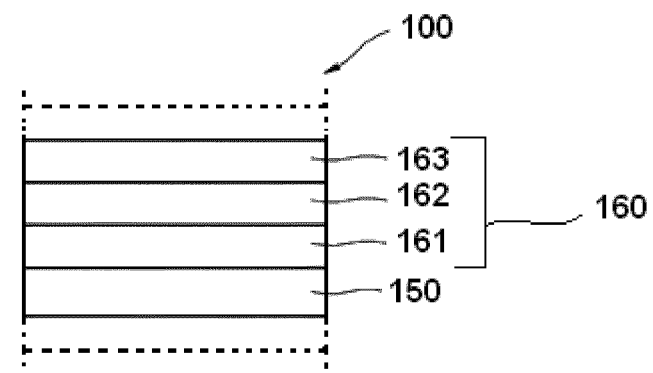
FIG. 3 is a schematic sectional view of an OLED, according to an exemplary embodiment of the present invention with an emission layer and three electron transport layers.

FIG. 3 is a schematic sectional view of an organic light-emitting diode 100, according to an exemplary embodiment of the present invention. The OLED 100 comprises an emission layer 150 and an electron transport layer stack (ETL) 160 comprising a first electron transport layer (ETL1) 161 that comprises compound of formula 1, a second electron transport layer (ETL2) 162 that comprises compound of formula 1 but different to the compound of the first electron transport layer, and a third electron transport layer (ETL3) 163, whereby the second electron transport layer 162 is disposed directly on the first electron transport layer 161 and the third electron transport layer 163 is disposed directly on the first electron transport layer 162.

Figure 4:
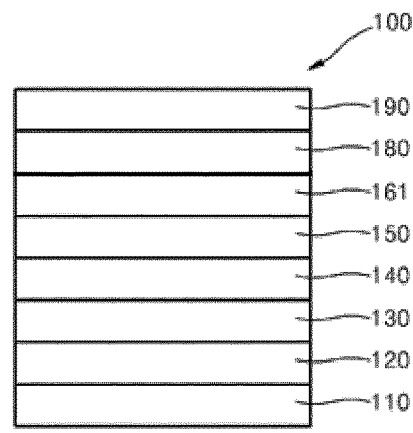
FIG. 4 is a schematic sectional view of an organic light-emitting diode (OLED), according to an exemplary embodiment of the present invention with an emission layer and one electron transport layer.

FIG. 4 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, one first electron transport layer (ETL1) 161, an electron injection layer (EIL) 180, and a cathode electrode 190. The first electron transport layer (ETL1) 161 comprises compound of formula 1 and optionally an alkali halide or alkali organic complex. The electron transport layer (ETL1) 161 is formed directly on the EML 150.

Figure 5:
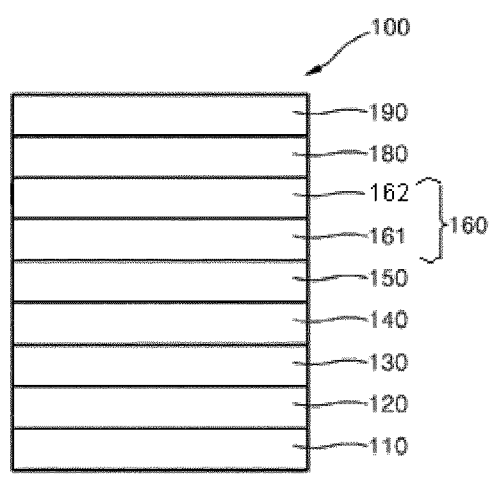
FIG. 5 is a schematic sectional view of an organic light-emitting diode (OLED), according to an exemplary embodiment of the present invention with an emission layer and two electron transport layers.

FIG. 5 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a cathode electrode 190. The electron transport layer (ETL) 160 comprises a first electron transport layer 161 and a second electron transport layer 162, wherein the first electron transport layer is arranged near to the anode (120) and the second electron transport layer is arranged near to the cathode (190). The first and/or the second electron transport layer comprise compound of formula 1 and optionally an alkali halide or alkali organic complex.

Figure 6:
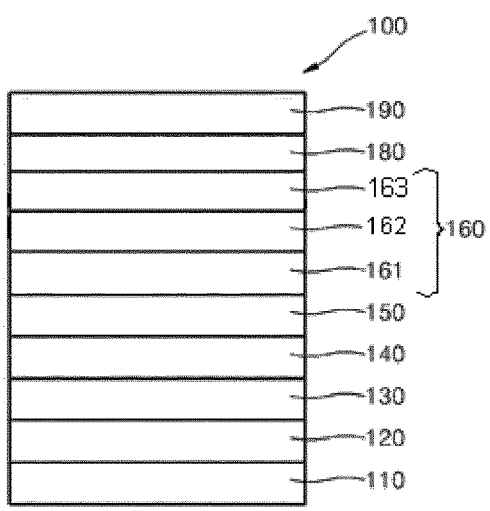
FIG. 6 is a schematic sectional view of an OLED, according to an exemplary embodiment of the present invention with an emission layer and three electron transport layers.

FIG. 6 is a schematic sectional view of an organic light-emitting diode 100, according to an exemplary embodiment of the present invention. The OLED 100 comprises a substrate 110, a first anode electrode 120, a hole injection layer (HIL) 130, a hole transport layer (HTL) 140, an emission layer (EML) 150, an electron transport layer stack (ETL) 160, an electron injection layer (EIL) 180, and a second cathode electrode 190. The electron transport layer stack (ETL) 160 comprises a first electron transport layer (ETL1) 161, a second electron transport layer (ETL2) 162 and a third electron transport layer (ETL3) 163. The first electron transport layer 161 is formed directly on the emission layer (EML) 150. The first, second and/or third electron transport layer comprise compound of formula 1 that is different for each layer, and optionally an alkali halide or alkali organic complex.

Organic Semiconductor Layer

According to another aspect an organic semiconductor layer may comprise at least one compound of formula 1.

According to one embodiment the organic semiconductor layer may comprises at least one compound of formula 1 and further comprises a metal, metal salt or organic alkali metal complex, preferably alkali metal complex, more preferably LiQ or alkali borate.

According to one embodiment the organic semiconductor layer may comprises at least one compound of formula 1 and further comprises a metal, metal salt or organic metal complex, preferably an organic monovalent or divalent metal complex, more preferably LiQ or alkali borate.

According to one embodiment the organic semiconductor layer may comprises at least one compound of formula 1 and LiQ.

According to one embodiment the organic semiconductor layer may comprises at least one compound of formula 1 and alkali borate.

According to one embodiment, wherein at least one organic semiconductor layer is arranged between the emission layer and the cathode, preferably between the electron injection layer and the cathode.

In another embodiment, the organic semiconductor layer is a first electron transport layer and it is arranged between the emission layer and the second electron transport layer.

According to one embodiment, the organic semiconductor layer is arranged between the first and second emission layer. The organic semiconductor layer can be an electron transport layer, an emission layer, a hole blocking layer, a charge generation layer and/or an electron injection layer, preferably an electron transport layer or a charge generation layer, and more preferred an electron transport layer.

According to one embodiment, the organic semiconductor layer can be arranged between a photoactive layer and a cathode layer, preferably between an emission layer or light-absorbing layer and the cathode layer, preferably the organic semiconductor layer is an electron transport layer.

According to one embodiment, the organic semiconductor layer may comprise at least one alkali halide or alkali organic complex.

An organic semiconductor layer comprises a compound according to formula 1, 1a or 1b is essentially non-emissive or non-emitting.

Organic Electronic Device

An organic electronic device comprising an anode layer, a cathode layer and at least one organic semiconductor layer according, wherein the at least one organic semiconductor layer comprises a compound of formula 1.

An organic electronic device according to one embodiment, which comprises at least one organic semiconductor layer that comprises a compound according to formula 1, wherein this layer is essentially non-emissive or non-emitting.

According to one embodiment, the organic electronic device may comprises at least one organic semiconductor layer comprising compound of formula 1 that is an electron transport layer, an emission layer, a hole blocking layer, a charge generation layer and/or an electron injection layer, preferably an electron transport layer or a charge generation layer, more preferred an electron transport layer.

The organic electronic device according to according to one embodiment may comprises at least one organic semiconductor layer, wherein the organic semiconductor layer comprising compound of formula 1 is arranged between a photoactive layer and a cathode layer, preferably between an emission layer or light-absorbing layer and the cathode layer, preferably the organic semiconductor layer is an electron transport layer The organic electronic device according to one embodiment may comprises at least one organic semiconductor layer comprising compound of formula 1, wherein the at least one organic semiconductor layer further comprises at least one alkali halide or alkali organic complex.

An organic electronic device according to one embodiment comprises at least one organic semiconductor layer comprising at least one compound of formula 1, at least one anode layer, at least one cathode layer and at least one emission layer, wherein the organic semiconductor layer comprising at least one compound of formula 1 is preferably arranged between the emission layer and the cathode layer.

An organic electronic device according to one embodiment comprises at least one organic semiconductor layer comprising at least one compound of formula 1, at least one anode layer, at least one cathode layer, at least one emission layer and at least one auxiliary electron transport layer, wherein the organic semiconductor layer comprising at least one compound of formula 1 is preferably arranged between the auxiliary electron transport layer and the cathode layer.

An organic electronic device according to one embodiment comprises at least one organic semiconductor layer comprising at least one compound of formula 1 and further comprises at least one alkali halide or alkali organic complex.

An organic light-emitting diode (OLED) according to the invention may include an anode, a hole transport layer (HTL), an emission layer (EML), an electron transport layer (ETL) comprising at least one compound of formula 1, and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device. A light emitting device can be an OLED.

According to one embodiment the OLED may have the following layer structure, wherein the layers having the following order:
an anode layer, a hole injection layer, optional a first hole transport layer, optional a second hole transport layer, an emission layer, an electron transport layer comprising compound of formula 1 according to the invention, an electron injection layer, and a cathode layer.

According to another aspect of the present invention, there is provided a method of manufacturing an organic electronic device, the method using:
  at least one deposition source, preferably two deposition sources and more preferred at least three deposition sources.

The methods for deposition that can be suitable comprise:
deposition via vacuum thermal evaporation;
deposition via solution processing, preferably the processing may be selected from spin-coating, printing, casting; and/or
slot-die coating.

According to various embodiments of the present invention, there is provided a method using:
  a first deposition source to release the compound of formula 1 according to the invention, and
  a second deposition source to release the alkali halide or alkali organic complex, preferably a lithium halide or lithium organic complex;
the method comprising the steps of forming the electron transport layer stack; whereby for an organic light-emitting diode (OLED):
  the first electron transport layer is formed by releasing the compound of formula 1 according to the invention from the first deposition source and the alkali halide or alkali organic complex, preferably a lithium halide or lithium organic complex from the second deposition source.

According to various embodiments of the present invention, the method may further include forming on the anode electrode an emission layer and at least one layer selected from the group comprising of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
  on a substrate a first anode electrode is formed,
  on the first anode electrode an emission layer is formed,
  on the emission layer an electron transport layer stack is formed, preferably a first electron transport layer is formed on the emission layer and a second electron transport layer is formed on the first electron transport layer and the second electron transport layer comprises a compound of formula 1,
  and finally a cathode electrode is formed,
  optional a hole injection layer, a hole transport layer, and a hole blocking layer, formed in that order between the first anode electrode and the emission layer,
  optional an electron injection layer is formed between the electron transport layer stack and the cathode electrode.

According to various embodiments of the present invention, the method may further include forming an electron injection layer on a first electron transport layer. However, according to various embodiments of the OLED of the present invention, the OLED may not comprise an electron injection layer.

According to various embodiments, the OLED may have the following layer structure, wherein the layers having the following order:
an anode, first hole transport layer, second hole transport layer, emission layer, optional second electron transport layer, first electron transport layer comprising compound of formula 1 according to the invention, optional a second electron transport layer, optional an electron injection layer, and a cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

Hereinafter, the embodiments are illustrated in more detail with reference to examples. However, the present disclosure is not limited to the following examples. Reference will now be made in detail to the exemplary aspects.

Preparation of Compounds of Formula 1

Compounds of formula 1 may be prepared as described below.

Preparation of 2-(dibenzo[b,d]furan-3-yl)-4-phenyl-6-(4-(10-phenylphenanthren-9-yl)phenyl)-1,3,5-triazine (J1)

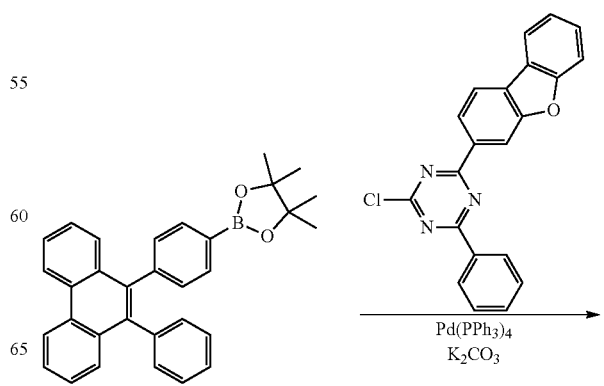

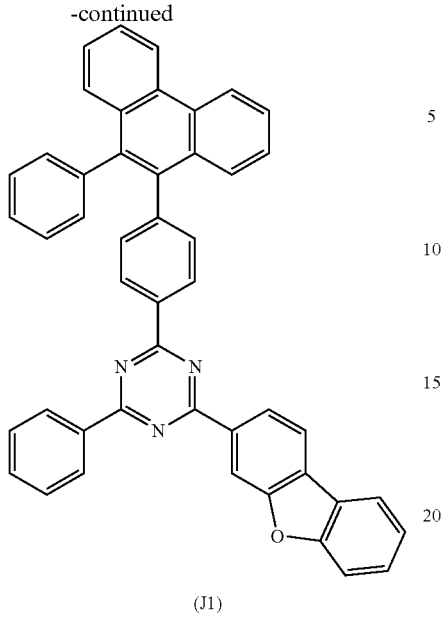

(J1)

A flask was flushed with nitrogen and charged with 2-chloro-4-(dibenzo[b,d] furan-3-yl)-6-phenyl-1,3,5-triazine (3.3 g, 9.2 mmol), 4,4,5,5-tetramethyl-2-(4-(10-phenylphenanthren-9-yl)phenyl)-1,3,2-dioxaborolane (4.6 g, 10.1 mmol), Pd(PPh3)4 (0.21 g, 0.18 mmol), and K2CO3 (2.5 g, 18.3 mmol). A mixture of deaerated tetrahydrofurane/water (4:1, 45 mL) was added and the reaction mixture was heated to 75° C. under a nitrogen atmosphere overnight. Then, additional Pd(PPh3)4 (0.03 g, 0.03 mmol) was added and the reaction mixture was heated to 75° C. under a nitrogen atmosphere overnight. After cooling down to 5° C., the resulting precipitate was isolated by suction filtration and washed with tetrahydrofurane (2×5 mL) and hexane (3×10 mL). The crude product was then dissolved in dichloromethane (4 L) and the organic phase was washed with water (3×500 mL). After drying over MgSO4, the organic phase was filtered through a silica gel pad. After rinsing with additional dichloromethane/methanol (100/1, 700 mL), the filtrate was concentrated under reduced pressure to 30 mL and hexane (30 mL) was added. The precipitate was collected by suction filtration and recrystallized (×2) in chlorobenzene (100 mL). The precipitate was collected by suction filtration to yield 4.3 g (72%). Final purification was achieved by sublimation. HPLC/ESI-MS: >99%, m/z=652 ([M+H]+).

Preparation of 2,4-diphenyl-6-(4'-(10-phenylphenanthren-9-yl)-[1,1'-biphenyl]-4-yl)-1,3,5-triazine (J2)

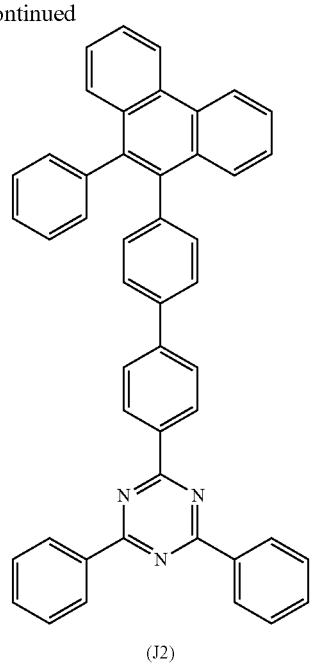

(J2)

A flask was flushed with nitrogen and charged with 2,4-diphenyl-6-(4-(4,4,5,5-tetramethyl-1,3,2-dioxaborolan-2-yl)phenyl)-1,3,5-triazine (7.8 g, 18.0 mmol), 9-(4-bromophenyl)-10-phenylphenanthrene (7.4 g, 18.0 mmol), Pd(PPh3)4 (0.62 g, 0.54 mmol), and K$_2$CO$_3$ (5.0 g, 35.9 mmol). A mixture of deaerated dioxane/water (10:1, 198 mL) was added and the reaction mixture was heated to reflux under a nitrogen atmosphere overnight. After cooling down to room temperature, the resulting precipitate was isolated by suction filtration and washed with water and methanol. The crude product was then dissolved in chloroform (600 mL) and filtered through a silica gel pad. After rinsing with additional chloroform (200 mL), the filtrate was concentrated under reduced pressure to 200 mL and n-hexane (200 mL) was added. The precipitate was collected by suction filtration to yield 6.1 g (52%). Final purification was achieved by sublimation. HPLC/ESI-MS: >99%, m/z=638 ([M+H]+).

Preparation of 7-(4'-(10-phenylphenanthren-9-yl)-[1,1'-biphenyl]-3-yl)dibenzo[c,h]acridine (J3)

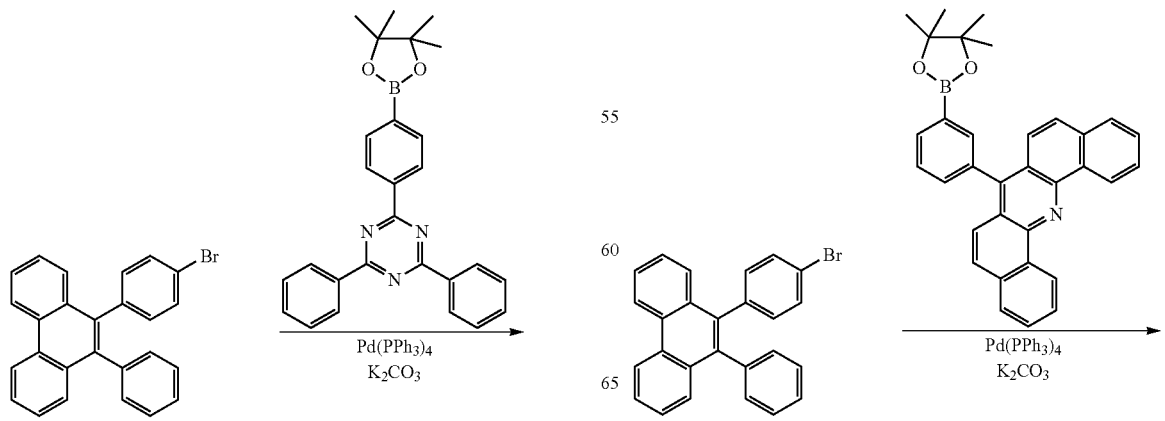

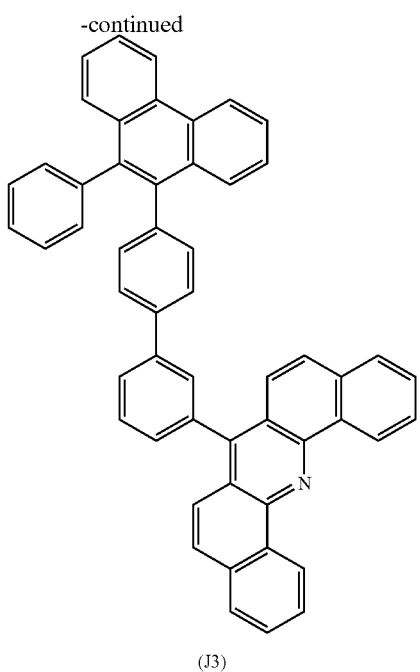

(J3)

A flask was flushed with nitrogen and charged with 7-(3-(4,4,5,5-tetramethyl-1,3,2-dioxaborolan-2-yl)phenyl) dibenzo[c,h]acridine (8.5 g, 17.6 mmol), 9-(4-bromophenyl)-10-phenylphenanthrene (8.0 g, 19.5 mmol), Pd(PPh3)4 (0.68 g, 0.59 mmol), and K2CO3 (5.4 g, 39.1 mmol). A mixture of deaerated dioxane/water (10:1, 215 mL) was added and the reaction mixture was heated to reflux under a nitrogen atmosphere overnight. After cooling down to room temperature, the resulting precipitate was isolated by suction filtration and washed with water (till neutral pH) and methanol. The crude product was then dissolved in hot chloroform (250 mL) and the organic phase was filtered through a silica gel pad. After rinsing with additional chloroform (200 mL), the filtrate was concentrated under reduced pressure. The precipitate was collected by suction filtration to yield 7.3 g (55%). Final purification was achieved by sublimation. HPLC/ESI-MS: 99.95%, m/z=684 ([M+H]+).

The chemical structure, molar mass, calculated HOMO, LUMO, dipole moment, melting point, glass transition temperature and rate onset temperature of compounds of formula 1 of example 1, example 2 and example 3 and comparative example 1 of C and $C_2$ are shown in Table 1.

TABLE 1

| Referred to as: | Structure | MW (g/mol) | mp (° C.) | Tg (° C.) | $T_{RO}$ (° C.) | HOMO (eV) | LUMO (eV) | Dipole moment (Debye) |
|---|---|---|---|---|---|---|---|---|
| C1 Comparative example 1 | 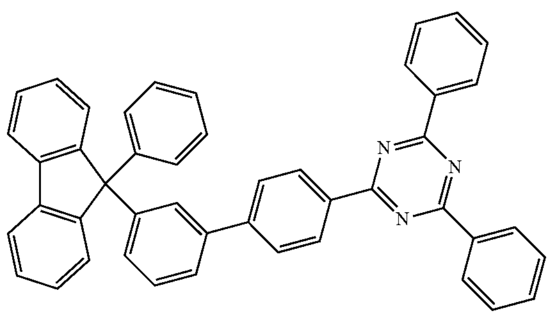 [SMILES: c1ccc(-c2nc(-c3ccccc3)nc(-c3ccc(-c4cccc(C5(c6ccccc6)c6ccccc6-c6ccccc65)c4)cc3)n2)cc1] | 625.25 | 304 | 123 | 268 | −5.81 | −1.85 | 0.58 |
| C2 Comparative example 2 | 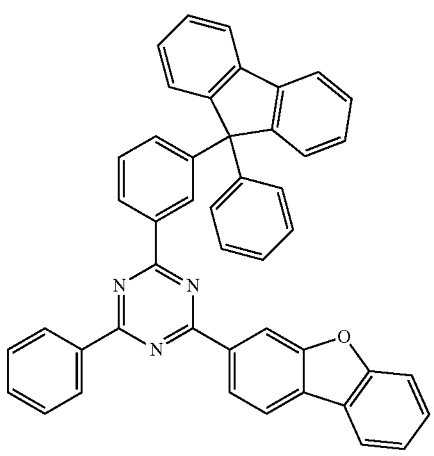 [SMILES: c1ccc(-c2nc(-c3cccc(C4(c5ccccc5)c5ccccc5-c5ccccc54)c3)nc(-c3ccc4c(c3)oc3ccccc34)n2)cc1] | 639.23 | — | 126 | 237 | −5.81 | −1.90 | 0.68 |

TABLE 1-continued

| Referred to as: | Structure | MW (g/mol) | mp (° C.) | Tg (° C.) | T$_{RO}$ (° C.) | HOMO (eV) | LUMO (eV) | Dipole moment (Debye) |
|---|---|---|---|---|---|---|---|---|
| J1 Example 1 | 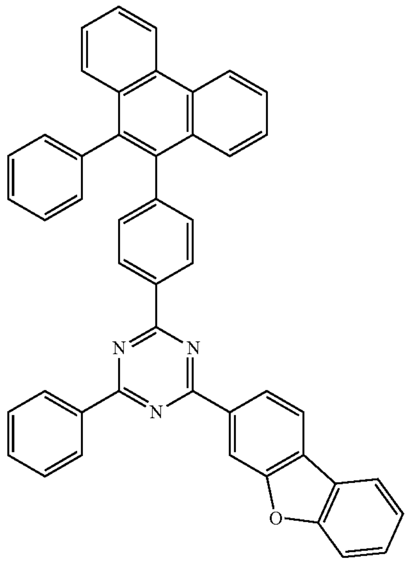 [SMILES: c1ccc(-c2nc(-c3ccc(-c4c(-c5ccccc5)c5ccccc5c5ccccc45)cc3)nc(-c3ccc4c(c3)oc3ccccc34)n2)cc1] | 651.23 | 318 | 161 | 258 | −5.65 | −1.93 | 0.83 |
| J2 Example 2 | 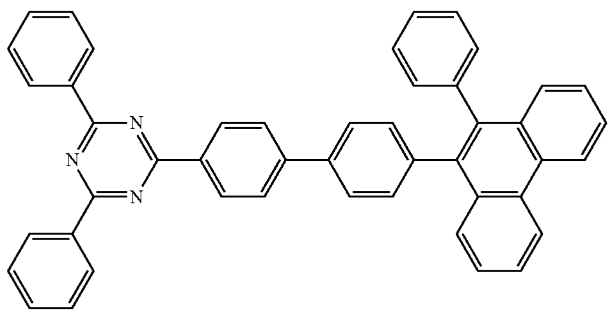 [SMILES: c1ccc(-c2nc(-c3ccccc3)nc(-c3ccc(-c4ccc(-c5c(-c6ccccc6)c6ccccc6c6ccccc56)cc4)cc3)n2)cc1] | 637.25 | 330 | 142 | 278 | −5.65 | −1.88 | 0.39 |
| J3 Example 3 | 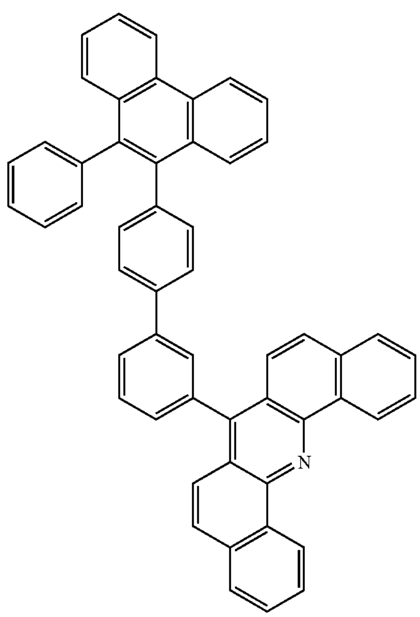 [SMILES: c1ccc(-c2c(-c3ccc(-c4cccc(-c5c6ccc7ccccc7c6nc6c5ccc5ccccc56)c4)cc3)c3ccccc3c3ccccc23)cc1] | 683.26 | 334 | 170 | 270 | −5.63 | −1.73 | 513 |

General Procedure for Fabrication of OLEDs

For top emission devices, Example 1 and 2 of compounds J1 and J2 and comparative examples $C_1$, a glass substrate was cut to a size of 50 mm×50 mm×0.7 mm, ultrasonically cleaned with isopropyl alcohol for 5 minutes and then with pure water for 5 minutes, and cleaned again with UV ozone for 30 minutes. 100 nm Ag were deposited on the glass substrate as anode at a pressure of $10^{-5}$ to $10^{-7}$ mbar to form the anode.

Then, 92 vol.-% Biphenyl-4-yl(9,9-diphenyl-9H-fluoren-2-yl)-[4-(9-phenyl-9H-carbazol-3-yl)phenyl]-amine (CAS 1242056-42-3) with 8 vol.-% 2,2',2''-(cyclopropane-1,2,3-triylidene)tris(2-(p-cyanotetrafluorophenyl)acetonitrile) was vacuum deposited on the anode, to form a hole injection layer (HIL) having a thickness of 10 nm. Then, Biphenyl-4-yl(9,9-diphenyl-9H-fluoren-2-yl)-[4-(9-phenyl-9H-carbazol-3-yl)phenyl]-amine was vacuum deposited on the HIL, to form a hole transport layer (HTL) having a thickness of 118 nm.

Then, N,N-bis(4-(dibenzo[b,d]furan-4-yl)phenyl)-[1,1':4',1''-terphenyl]-4-amine (CAS 1198399-61-9) was vacuum deposited on the HTL, to form an electron blocking layer (EBL) having a thickness of 5 nm.

Then 97 vol.-% ABH 113 (Sun Fine Chemicals, Korea) as EML host and 3 vol.-% NUBD370 (Sun Fine Chemicals, Korea) as fluorescent blue dopant were deposited on the EBL, to form a blue-emitting EML with a thickness of 20 nm.

Then, a first electron transport layer (ETL1) is formed on the EML with a thickness of 5 nm by depositing 2,4-diphenyl-6-(4',5',6'-triphenyl-[1,1': 2',1'': 3'',1''':3''',1''''-quinquephenyl]-3''''-yl)-1,3,5-triazine on the emission layer with a thickness of 5 nm, see Table 2.

Then, the second electron transport layer (ETL2) is formed on the first electron transport layer (ETL1) with a thickness of 31 nm by depositing 50 vol.-% of a compound selected from J1 for example 1 and J2 for example 2 of formula 1 as matrix compound and 50 vol.-% of alkali organic complex LiQ, see Table 2; as well as for the comparative example C1 the second electron transport layer is formed on the first electron transport layer with a thickness of 31 nm by depositing 50 vol.-% of the compound of the comparative example C1 as matrix compound and 50 vol.-% of alkali organic complex LiQ, see Table 2.

TABLE 2

Performance of an organic electroluminescent device comprising a first electron transport layer (ETL1) and second electron transport layer (ETL2) comprising a compound of formula 1 of J1 and J2 as well as for the comparative example compound C1.

|  | Matrix compound | Concentration of matrix compound in ETL 2 (vol.-%) | Alkali organic complex | Concentration of alkali organic complex (vol.-%) | Thickness electron transport layer (nm) | Operating voltage at 10 mA/cm$^2$ (V) | cd/A efficiency at 10 mA/cm$^2$ (cd/A) | LT97 at 30 mA/cm$^2$ (h) |
|---|---|---|---|---|---|---|---|---|
| Comparative example 1 | C1 | 50 | LiQ | 50 | 31 | 3.7 | 8.0 | 33 |
| Example 1 | J1 | 50 | LiQ | 50 | 31 | 3.4 | 7.9 | 32 |
| Example 2 | J2 | 50 | LiQ | 50 | 31 | 3.5 | 7.9 | 42 |

Then, the electron injection layer is formed on the electron transporting layer by deposing Yb with a thickness of 2 nm.

Then, Ag is evaporated at a rate of 0.01 to 1 Å/s at $10^{-7}$ mbar to form a cathode with a thickness of 11 nm.

A cap layer of Biphenyl-4-yl(9,9-diphenyl-9H-fluoren-2-yl)-[4-(9-phenyl-9H-carbazol-3-yl)phenyl]-amine is formed on the cathode with a thickness of 75 nm.

The OLED stack is protected from ambient conditions by encapsulation of the device with a glass slide. Thereby, a cavity is formed, which includes a getter material for further protection.

To assess the performance of the inventive examples compared to the prior art, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in cd/m$^2$ using an Instrument Systems CAS-140CT array spectrometer for each of the voltage values.

The cd/A efficiency at 10 mA/cm$^2$ is determined by interpolating the luminance-voltage and current-voltage characteristics, respectively.

Lifetime LT of the device is measured at ambient conditions (20° C.) and 30 mA/cm$^2$, using a Keithley 2400 source meter, and recorded in hours.

The brightness of the device is measured using a calibrated photo diode. The lifetime LT is defined as the time till the brightness of the device is reduced to 97% of its initial value.

Technical Effect of the Invention

Compound $C_1$ is a state of the art compound. As can be seen in Table 1, the compounds of formula 1 of the example 1, 2 and 3 have a higher melting point and higher glass transition temperature as compared to the comparative example 1. The rate onset temperature is in a range suitable for mass production.

As can be seen in Table 2, the operating voltage at 10 mA/cm$^2$ of organic electronic devices comprising the compound of formula 1 is improved; see examples 1 and 2, over organic electronic devices comprising the compound C1 of the comparative example.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound according to formula 1:

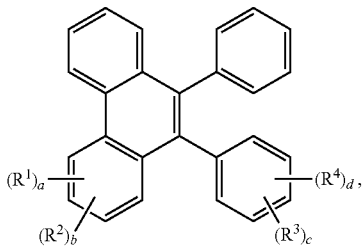

wherein $R^1$, $R^2$, $R^3$ and $R^4$ are independently selected from hydrogen, substituted or unsubstituted $C_6$ to $C_{38}$ aryl, substituted or unsubstituted $C_3$ to $C_{36}$ heteroaryl, substituted or unsubstituted $C_1$ to $C_{16}$ alkyl group, —PO(R')$_2$, D, F, CN, or formula 2;

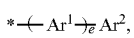

wherein the substituents are selected from $C_6$ to Cis aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

R' is independently selected from alkyl, aryl or heteroaryl;

a, b, c, d and e are independently 0, 1 or 2, wherein at least one of a, b, c and d is 1 or 2;

wherein at least one of $R^1$, $R^2$, $R^3$ and $R^4$ is formula 2, $Ar^1$ is selected from substituted or unsubstituted $C_6$ to $C_{38}$ arylene, substituted or unsubstituted $C_3$ to $C_6$ or $C_8$ to $C_{36}$ heteroarylene or substituted or unsubstituted $C_1$ to $C_{16}$ alkylene group, wherein the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_6$ or $C_8$ to $C_{36}$ heteroaryl, or substituted or unsubstituted $C_1$ to $C_{16}$ alkyl group, wherein the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

wherein $Ar^1$ does not contain one or more CN substituents when $Ar^2$ is substituted or unsubstituted $C_6$ to $C_{38}$ aryl;

wherein the following compound 3 is excluded:

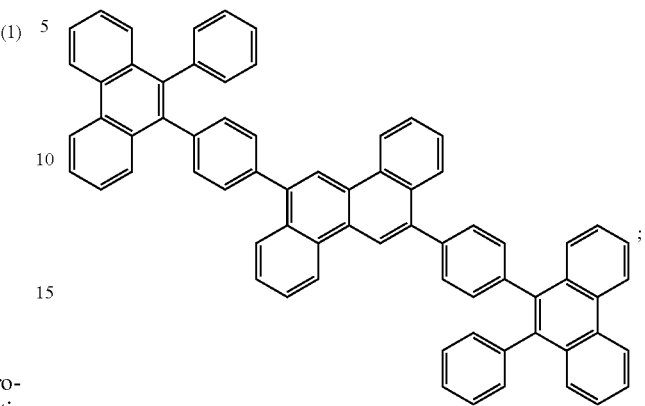

wherein, when present, $R^1$, $R^2$, or both $R^1$ and $R^2$, independently, (i) comprises a triazine moiety, or (ii) comprises a cyano substituent, or (iii) is formula 2 at the 1-, 2-, or 4-position of the 9,10-diphenylphenanthrene moiety of formula 1, wherein e is 1 or 2, or (iv) a combination thereof;

wherein, when present, $R^3$ (i) is not CN, (ii) is not an unsubstituted phenyl, (iii) is not an unsubstituted ethyl, (iv) is not a 4,6-diphenyl-1,3,5-triazin-2-yl, and (v) does not include a phenanthrenylene moiety; and wherein, when present, $R^4$ (i) is not CN, (ii) is not an unsubstituted phenyl, (iii) is not an unsubstituted ethyl, (iv) is not a 4,6-diphenyl-1,3,5-triazin-2-yl, and (v) does not include a phenanthrenylene moiety.

2. The compound of formula 1 according to claim 1, wherein at least two of a, b, c and d are 1 or 2; or a and b are 0 and c or d is independently selected from 1 or 2; or c and d are 0 and a or b is independently selected from 1 or 2; or a and c are 0 and b or d is independently selected from 1 or 2; or b and d are 0 and a or c is independently selected from 1 or 2; or at least three selected from a, b, c and d are 0 and one selected from a, b, c and d is 1; or at least three selected from a, b, c and d are 1 or 2.

3. The compound of formula 1 according to claim 1, wherein e is selected from 1 or 2.

4. The compound of formula 1 according to claim 1, wherein at least two of $R^1$, $R^2$, $R^3$ and $R^4$ are selected same when a+b+c+d≥2.

5. The compound of formula 1 according to claim 1, wherein at least one of $R^1$, $R^2$, $R^3$ and $R^4$ is independently selected from H, nitrile, phenyl, naphthyl, biphenyl, pyridinyl, dibenzofuran, dibenzothiophene or carbazole.

6. The compound of formula 1 according to claim 1, wherein one, two, or three of $R^1$, $R^2$, $R^3$ and $R^4$ is H.

7. The compound of formula 1 according to claim 1, wherein one or two of $R^1$, $R^2$, $R^3$ and $R^4$ are formula 2.

8. The compound of formula 1 according to claim 1, wherein $Ar^1$ is selected from substituted or unsubstituted phenylene, biphenylene, terphenylene, naphthylene, phenanthrylene, triphenylene, or anthracenylene, wherein the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy.

9. The compound of formula 1 according to claim 1, wherein $Ar^2$ is selected from substituted or unsubstituted aryl selected from a group consisting of anthracenyl, fluoranthenyl, and pyrenyl, or substituted or unsubstituted heteroaryl selected from a group consisting of pyridine, pyrimidine, triazine, quinoline, quinoxaline, benzoacridine, dibenzoacridine, phenanthroline, carbazole, dibenzofurane, and dibenzothiophene, wherein the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy.

10. The compound of formula 1 according to claim 1, wherein $R^1$, $R^2$, $R^3$ and $R^4$ are independently selected from hydrogen, CN, or D1 to D54:

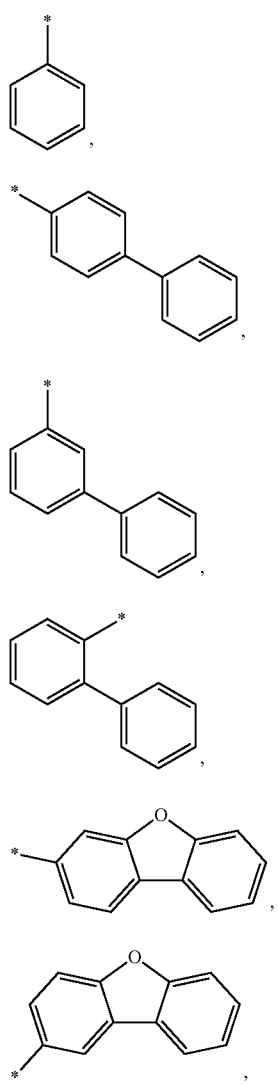

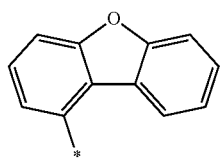

(D7)

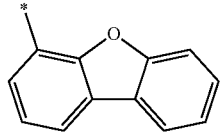

(D8)

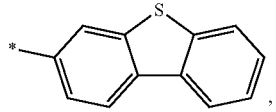

(D9)

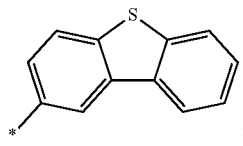

(D10)

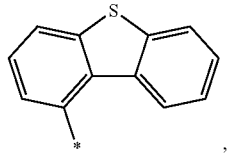

(D11)

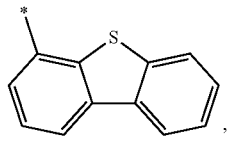

(D12)

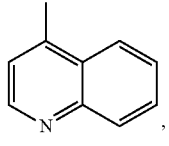

(D13)

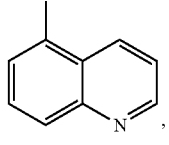

(D14)

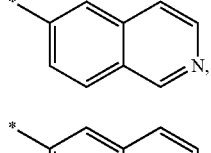

(D15)

(D16)

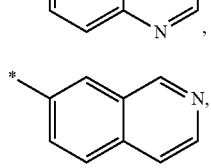

(D17)

-continued
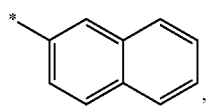 (D18)
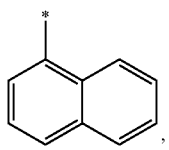 (D19)
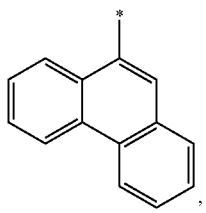 (D20)
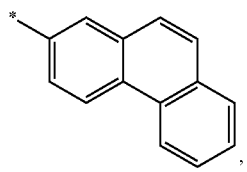 (D21)
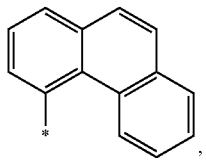 (D22)
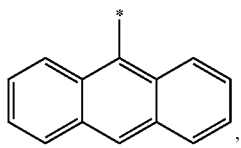 (D23)
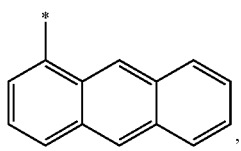 (D24)
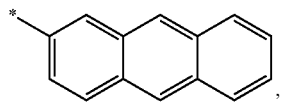 (D25)
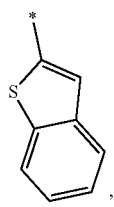 (D26)
-continued
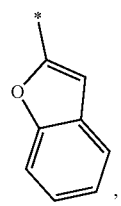 (D27)
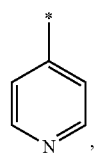 (D28)
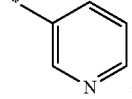 (D29)
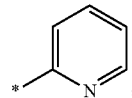 (D30)
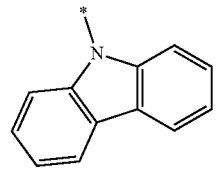 (D31)
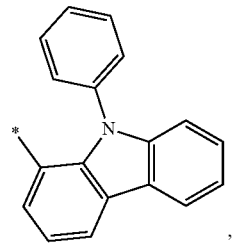 (D32)
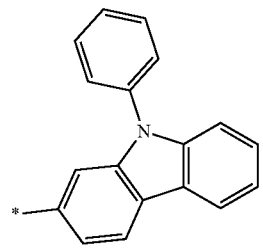 (D33)
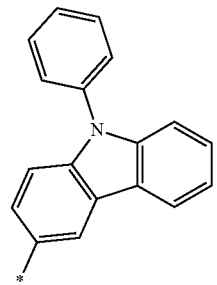 (D34)

-continued
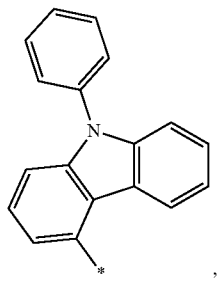
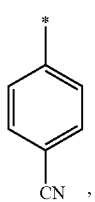
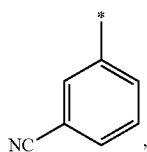
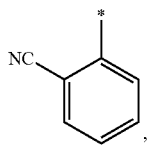
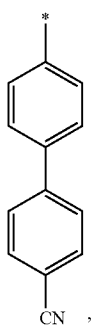
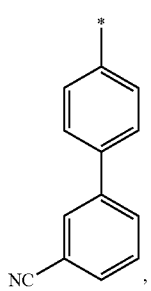
-continued
(D35) 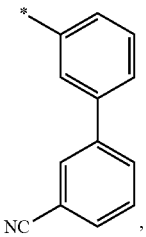
(D36) 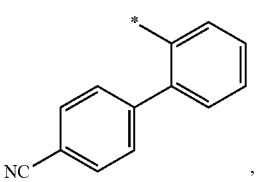
(D37) 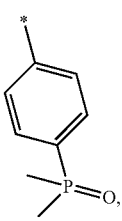
(D38) 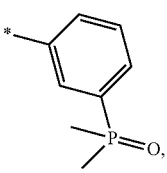
(D39) 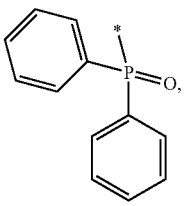
(D40) 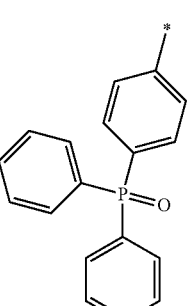
(D41) 
(D42) 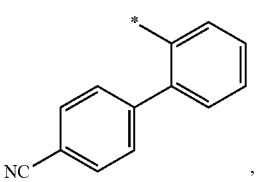
(D43) 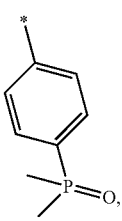
(D44) 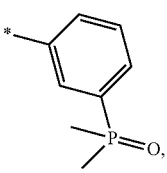
(D45) 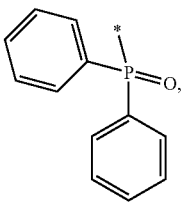
(D46) 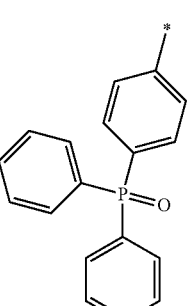
(D47) 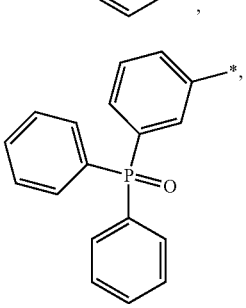

(D48) 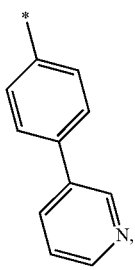
(D49) 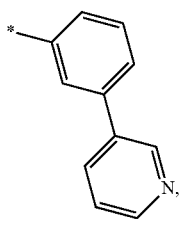
(D50) 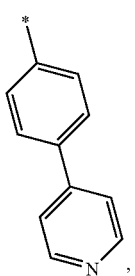
(D51) 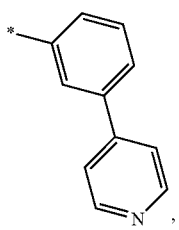
(D52) 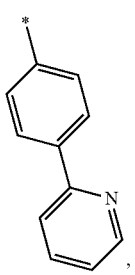
(D53) 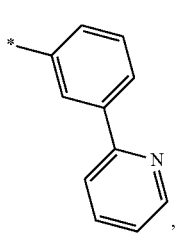
(D54) 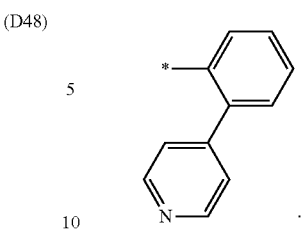
11. The compound of formula 1 according to claim 1, wherein Ar$^1$ is selected from E1 to E14:
(E1) 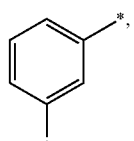
(E2) 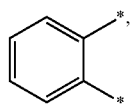
(E3) 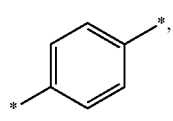
(E4) 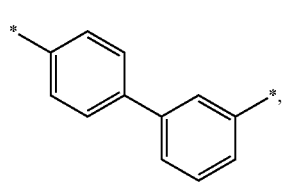
(E5) 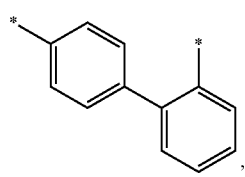
(E6) 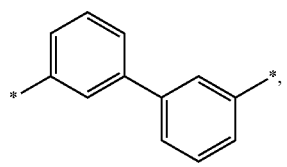
(E7) 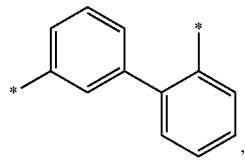
(E8)

-continued
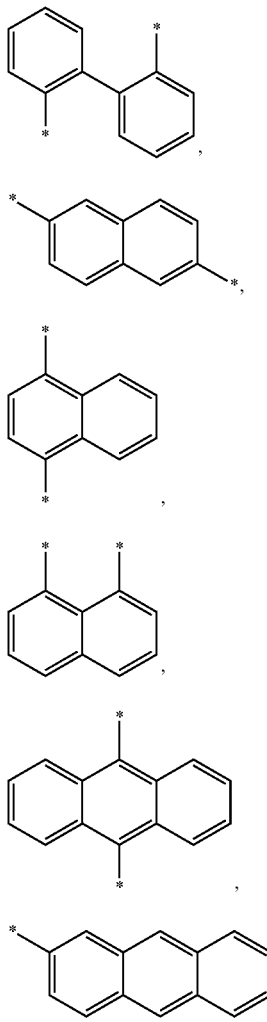
(E9)
(E10)
(E11)
(E12)
(E13)
(E14)
12. The compound of formula 1 according to claim 1, wherein Ar² is selected from F1 to F13:
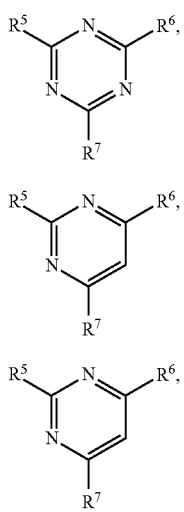
(F1)
(F2)
(F3)
-continued
(F4)
(F5)
(F6)
(F7)
(F8)
(F9)
(F10)

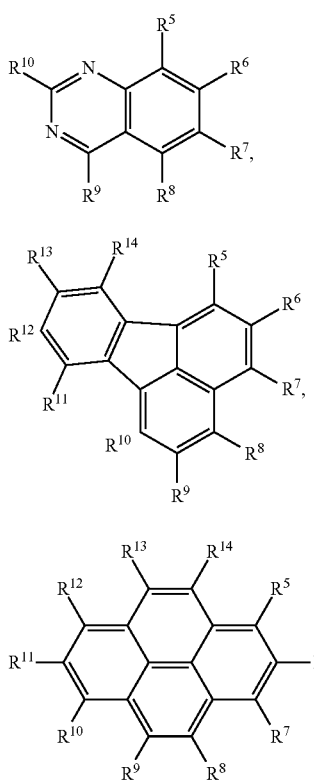

wherein
R[5], R[6], R[7], R[8], R[9], R[10], R[11], R[12], R[13], R[14] are independently selected from single bond, hydrogen, substituted or unsubstituted phenyl, naphthyl, biphenyl, pyridinyl, dibenzofuryl, benzofuranyl, dibenzothienyl, benzothiophenyl, anthracenyl, phenanthryl, or carbazolyl, wherein
the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy; and wherein
one of R[5], R[6], R[7], R[8], R[9], R[10], R[11], R[12], R[13], R[14] represents a single bond only, and the single bond is the single bond that bonds Ar[2] to Ar[1].

13. The compound of formula 1 according to claim 12, wherein R[5], R[6], R[7], R[8], R[9], R[10], R[11], R[12], R[13], R[14] are independently selected from G1 to G72:

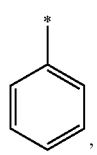

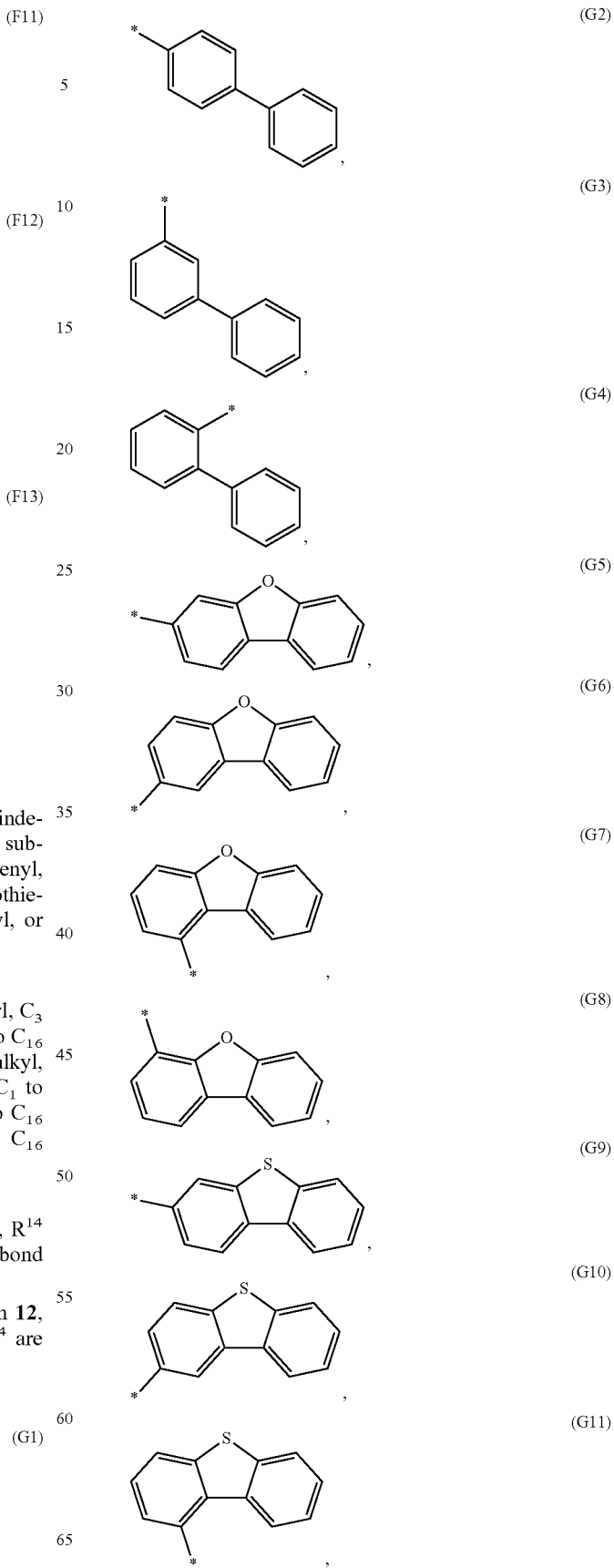

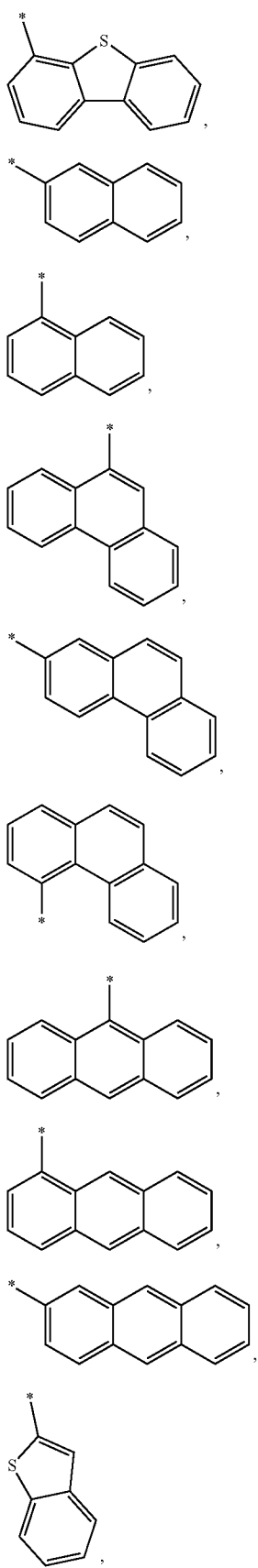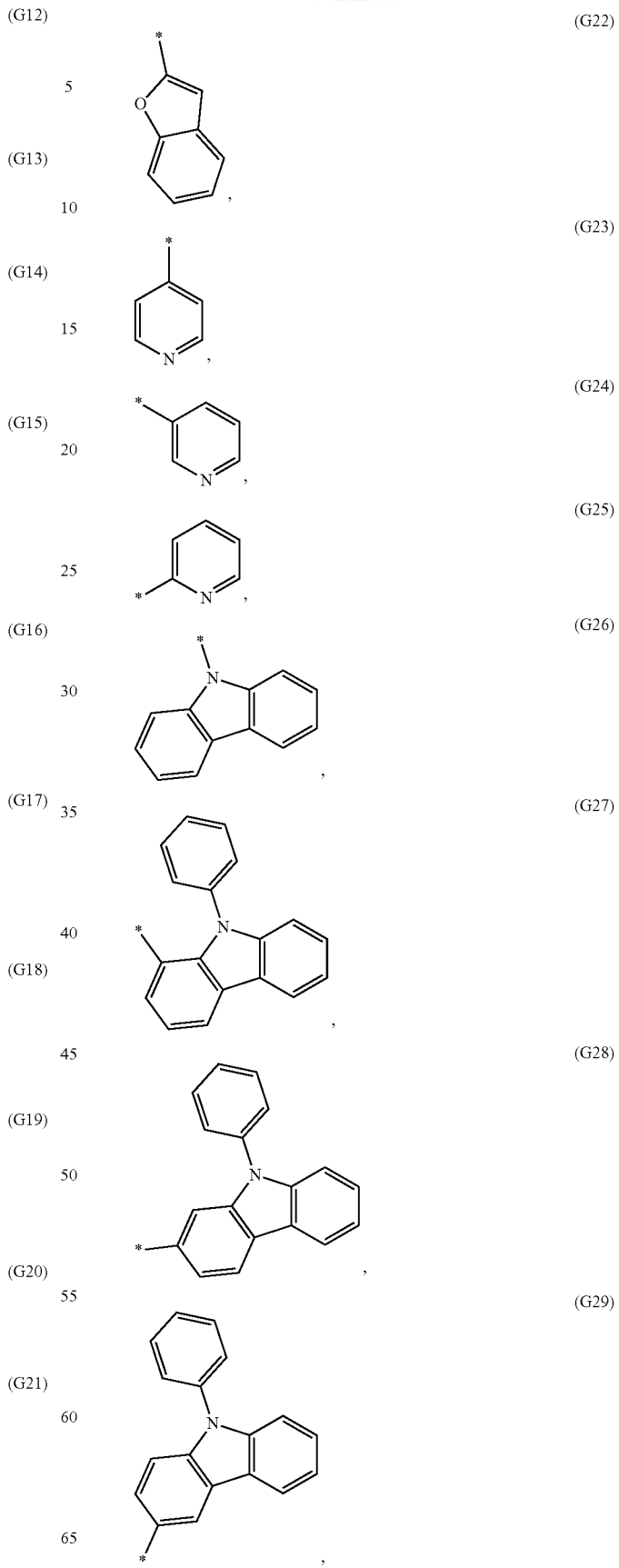

-continued
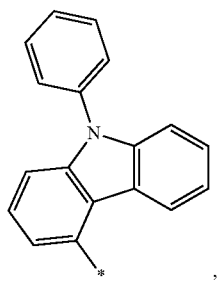 (G30)
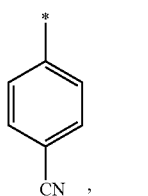 (G31)
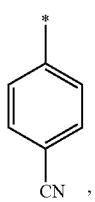 (G32)
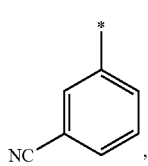 (G33)
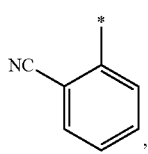 (G34)
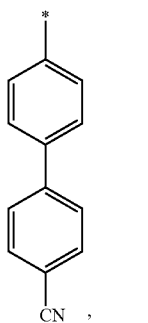 (G35)
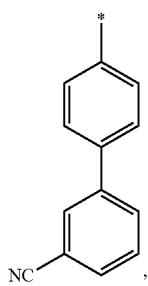 (G36)
-continued
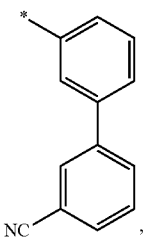 (G37)
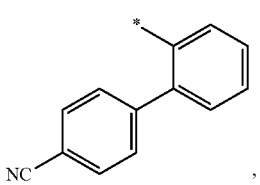 (G38)
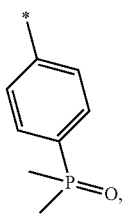 (G39)
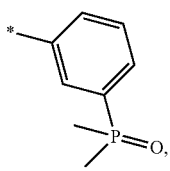 (G40)
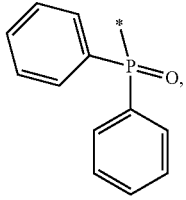 (G41)
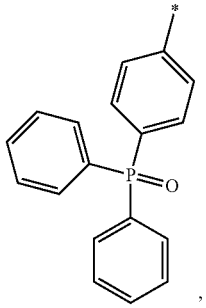 (G42)
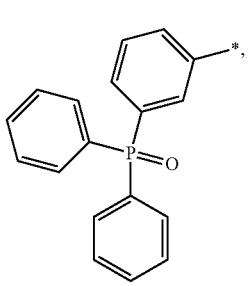 (G43)

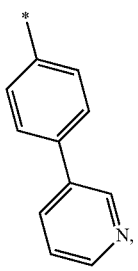 (G44)
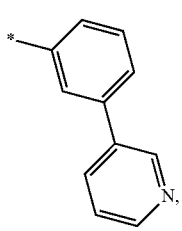 (G45)
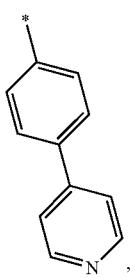 (G46)
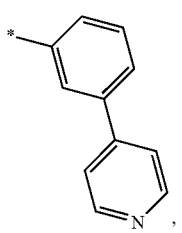 (G47)
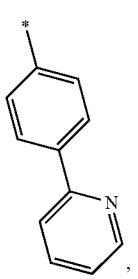 (G48)
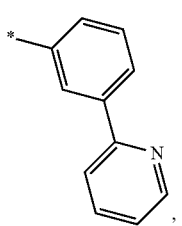 (G49)
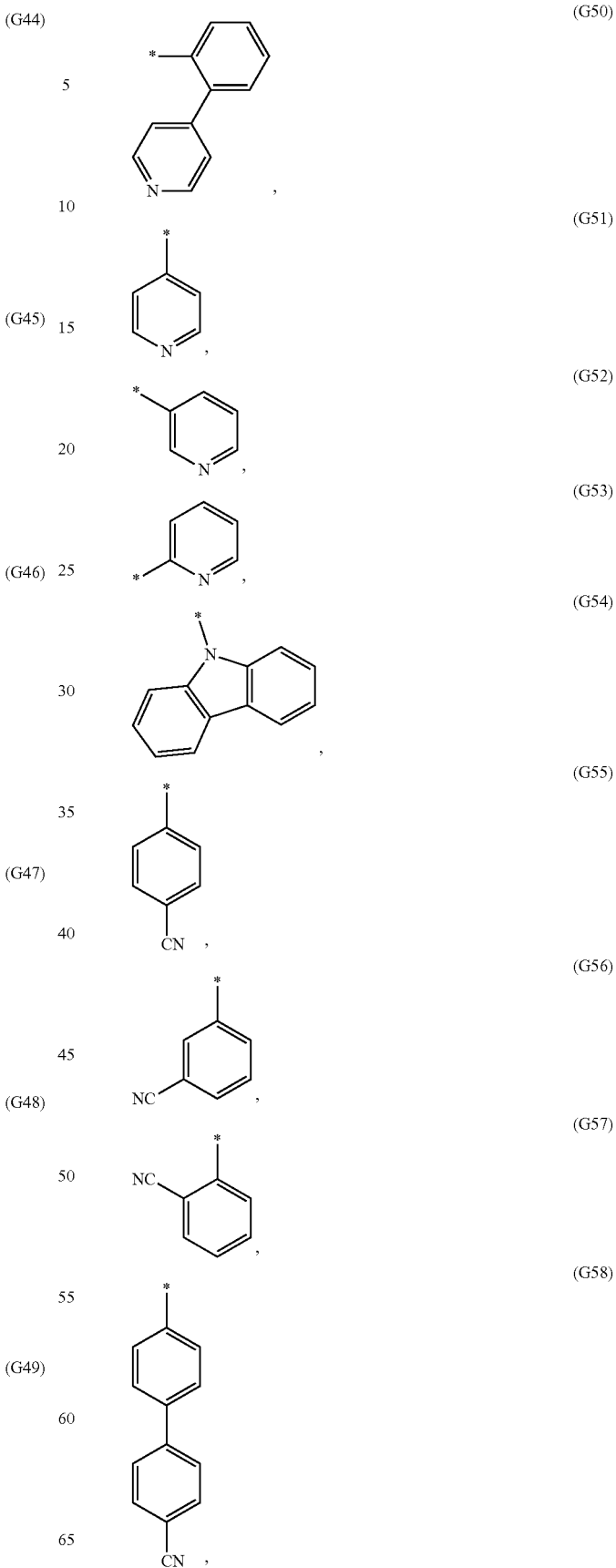

-continued
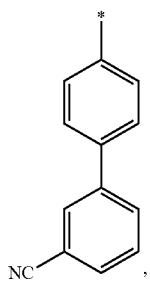
(G59)
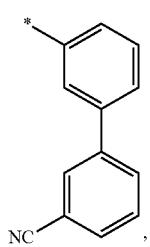
(G60)
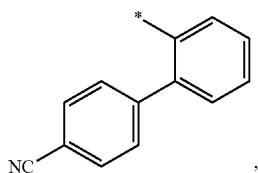
(G61)
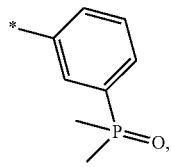
(G62)
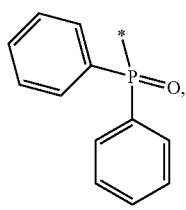
(G63)
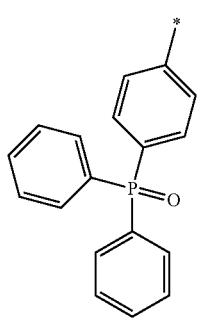
(G64)
-continued
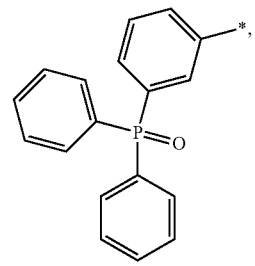
(G65)
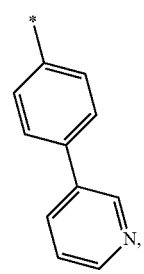
(G66)
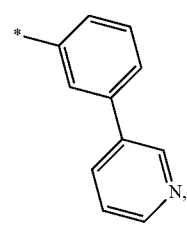
(G67)
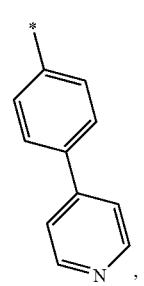
(G68)
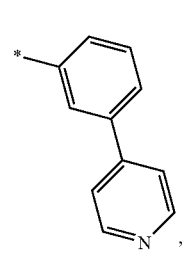
(G69)
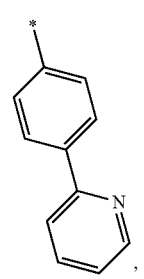
(G70)

123
-continued
(G71)
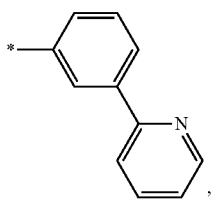
(G72)
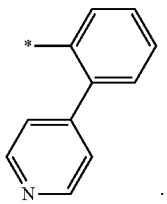
14. The compound of formula 1 according to claim 1, wherein Ar² is selected from H1 to H92:
(H1)
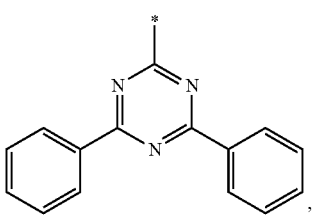
(H2)
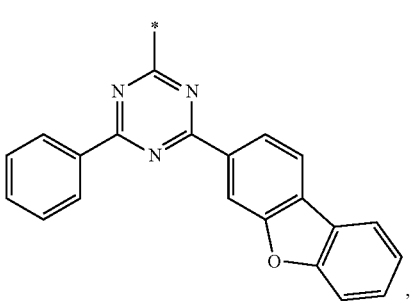
(H3)
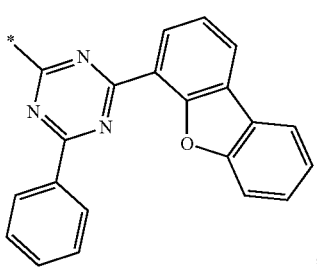
124
-continued
(H4)
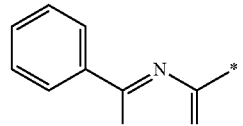
(H5)
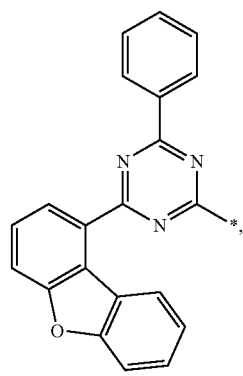
(H6)
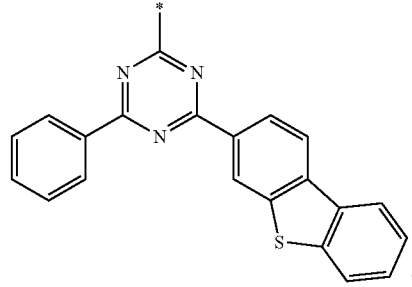
(H7)
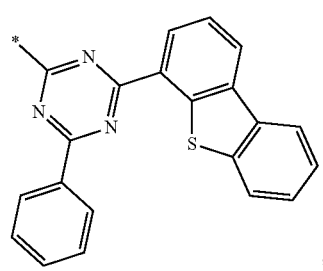

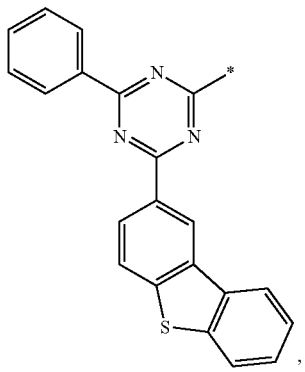 (H8)
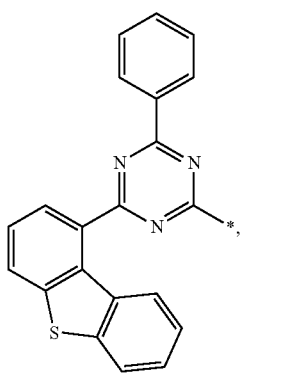 (H9)
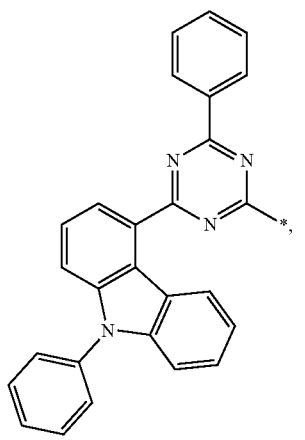 (H10)
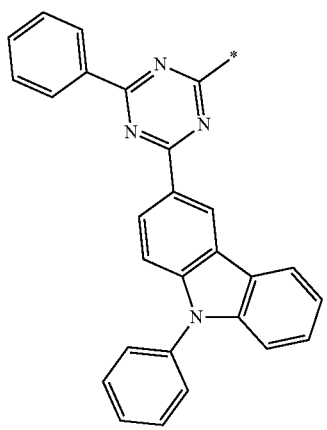 (H11)
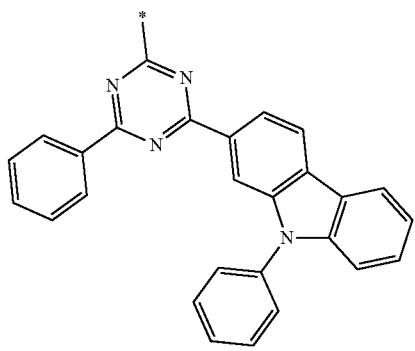 (H12)
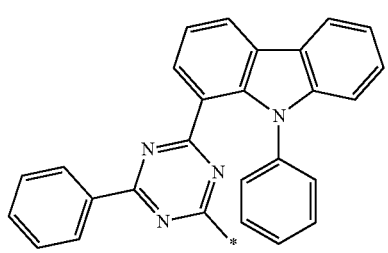 (H13)
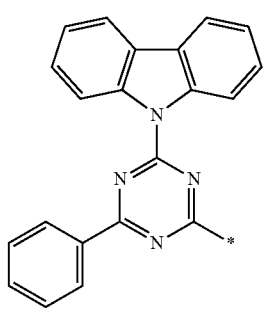 (H14)
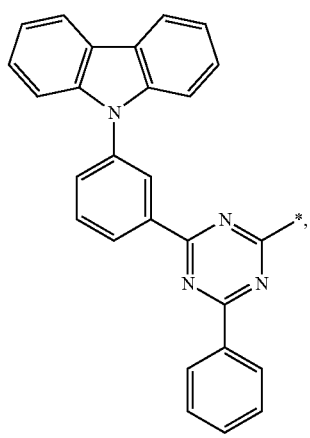 (H15)
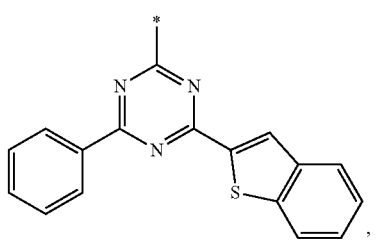 (H16)

(H17) 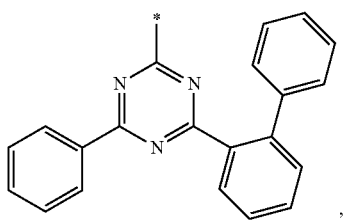
(H18) 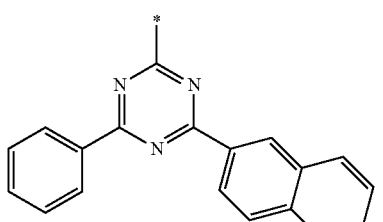
(H19) 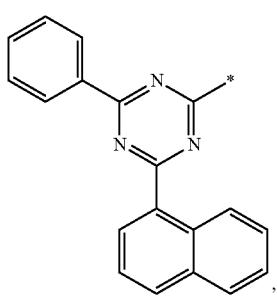
(H20) 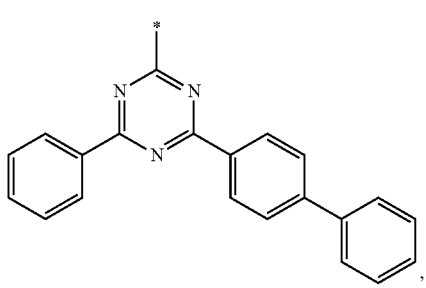
(H21) 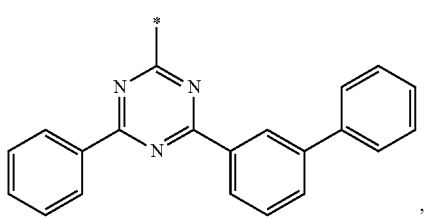
(H22) 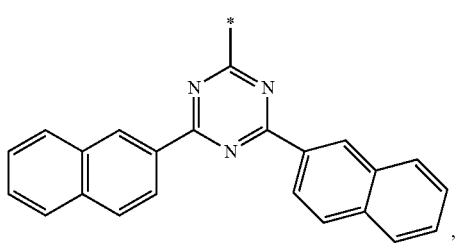
(H23) 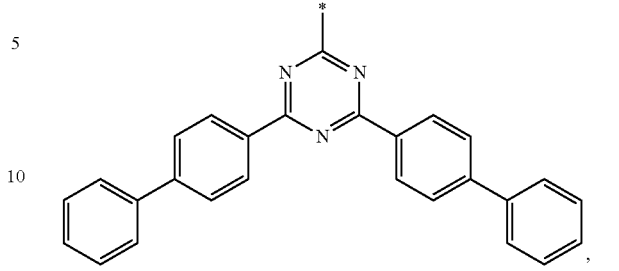
(H24) 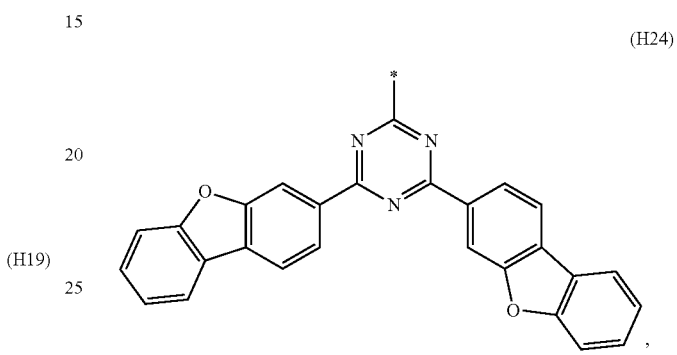
(H25) 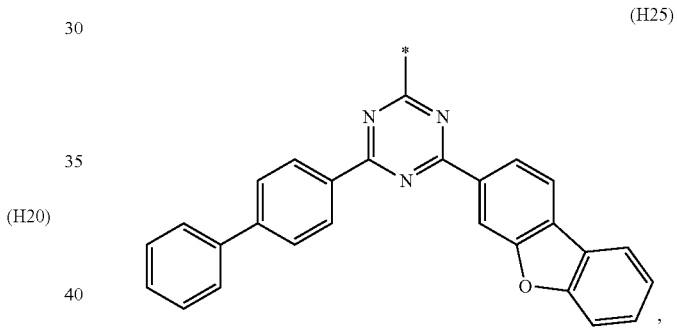
(H26) 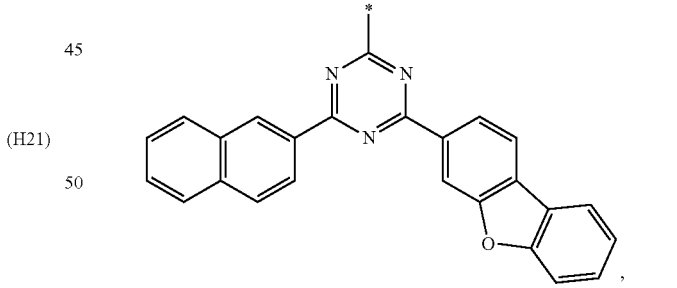
(H27) 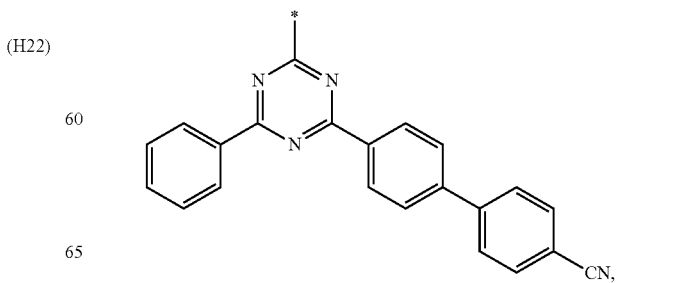

(H28)
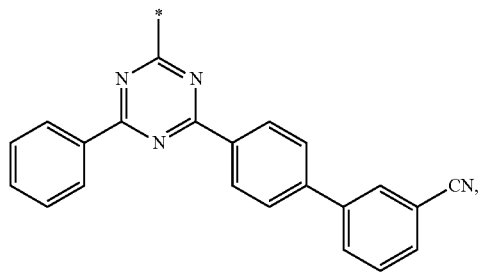
(H29)
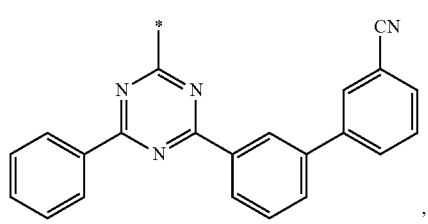,
(H30)
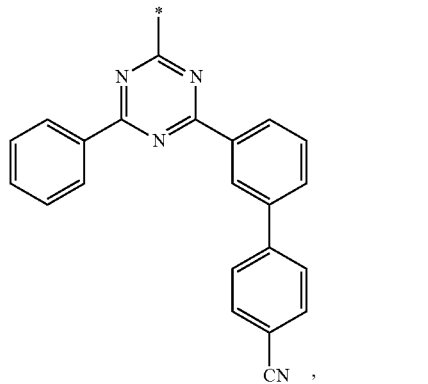,
(H31)
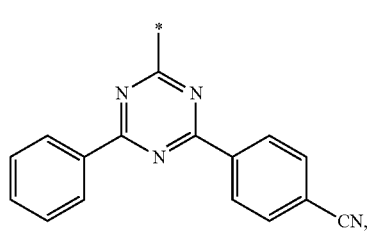,
(H32)
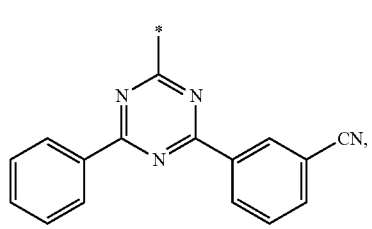,
(H33)
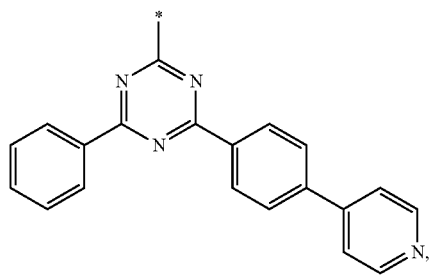,
(H34)
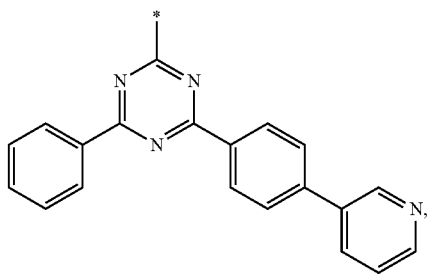
(H35)
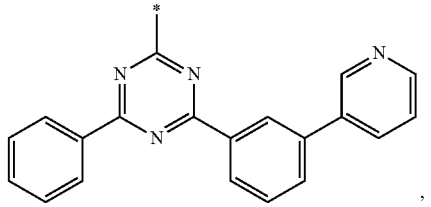,
(H36)
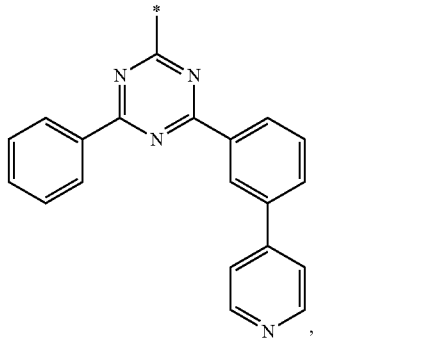,
(H37)
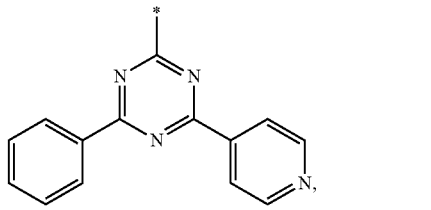,
(H38)
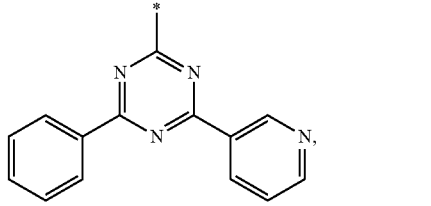,
(H39)
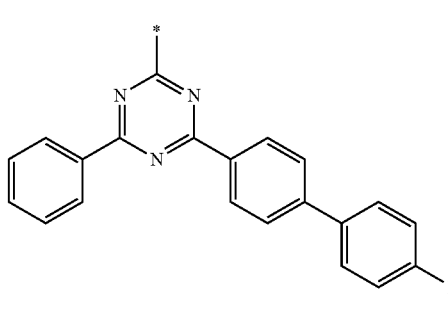, (H40)
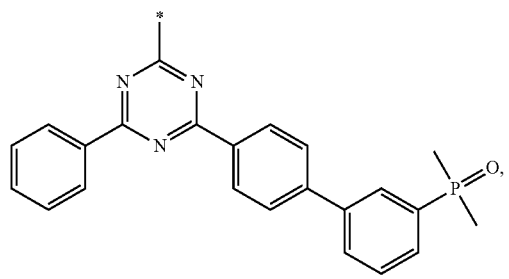
(H41)
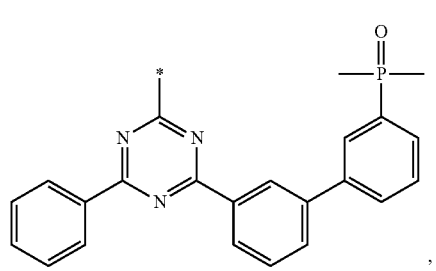
(H42)
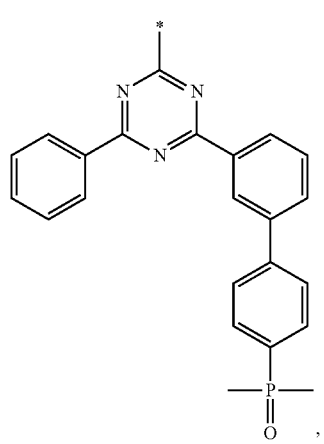
(H43)
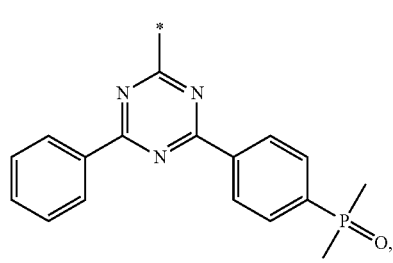
(H44)
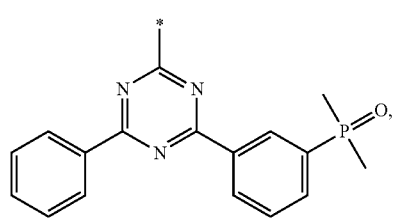
(H45)
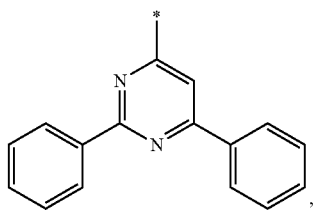
(H46)
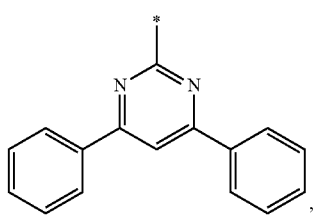
(H47)
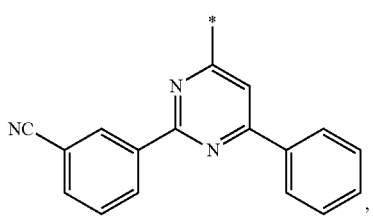
(H48)
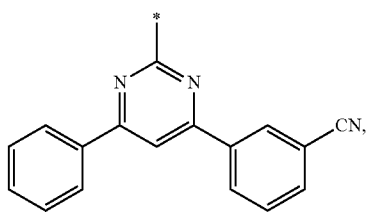
(H49)
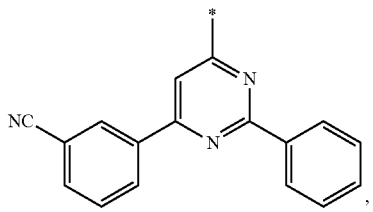
(H50)
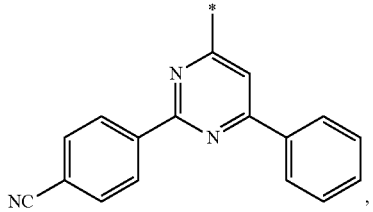
(H51)
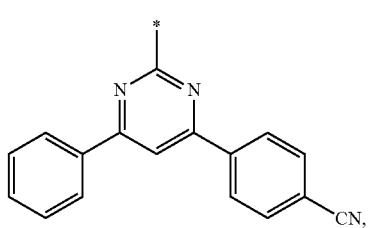

(H52)
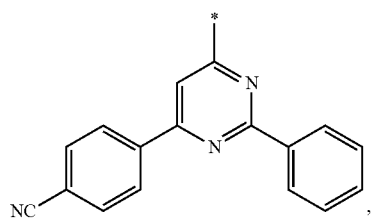
(H53)
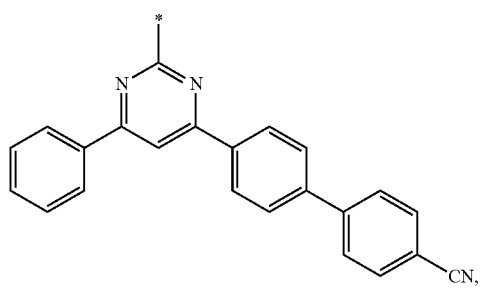
(H54)
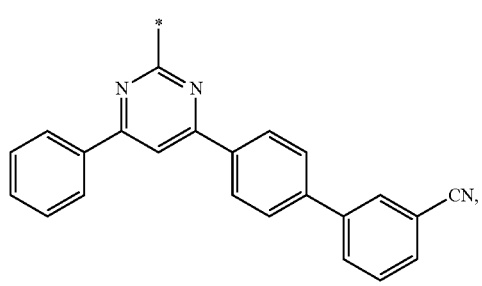
(H55)
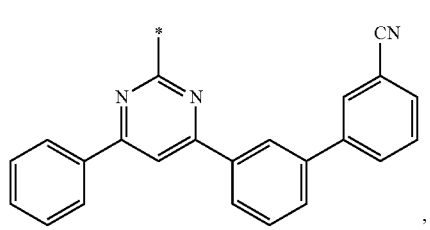
(H56)
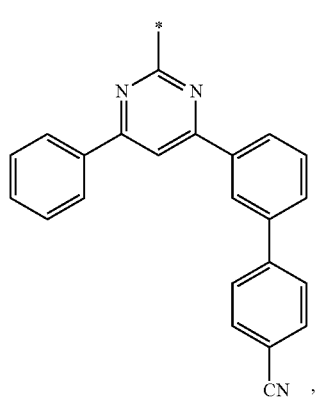
(H57)
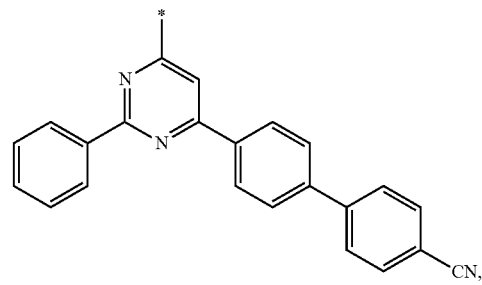
(H58)
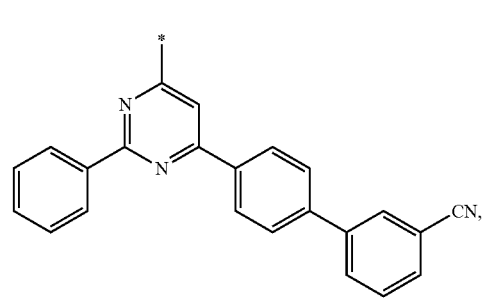
(H59)
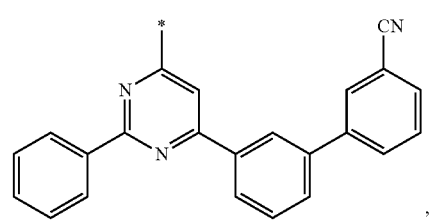
(H60)
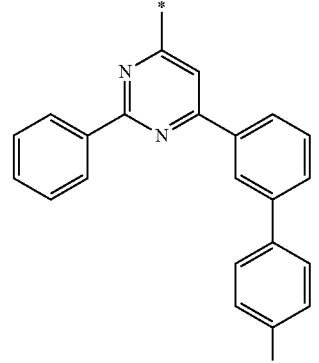
(H61)
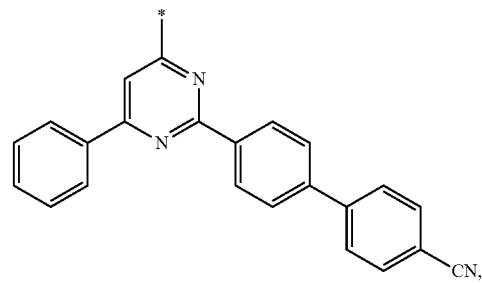

(H62)
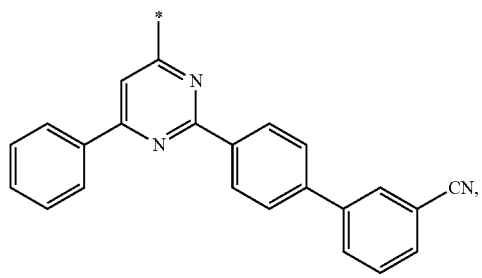
(H63)
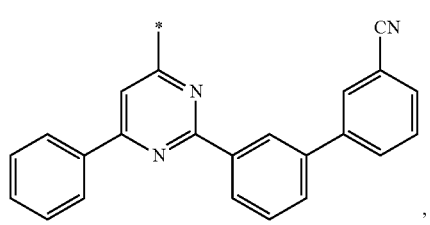
(H64)
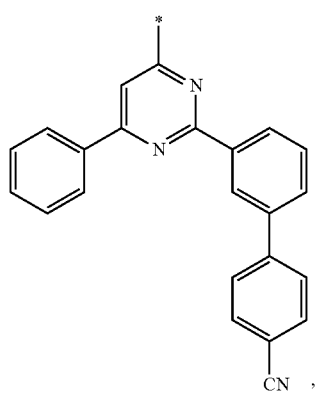
(H65)
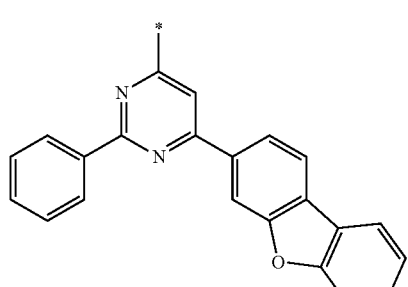
(H66)
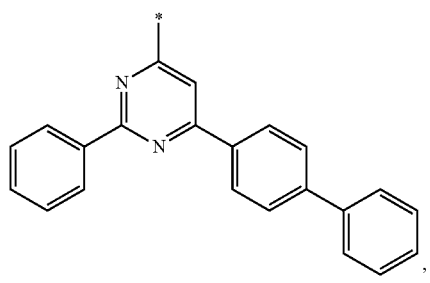
(H67)
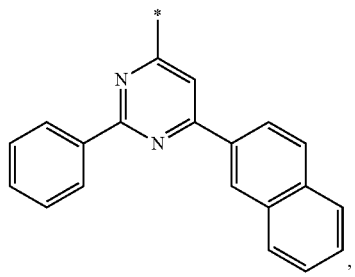
(H68)
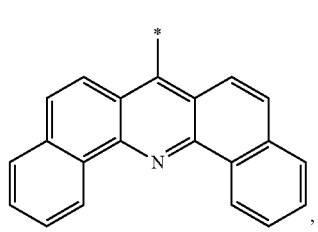
(H69)
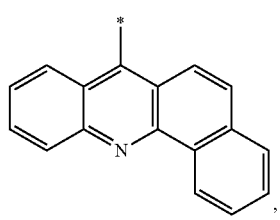
(H70)
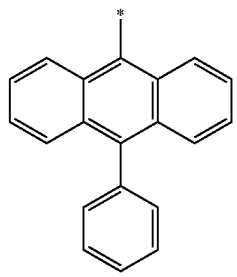
(H71)
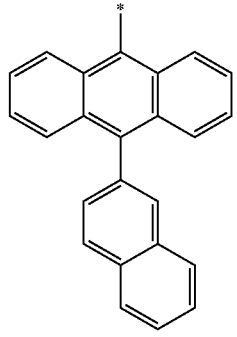

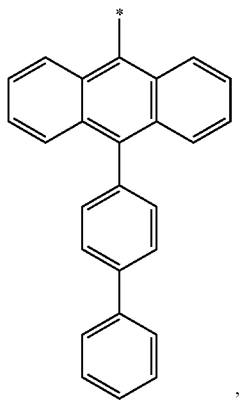 (H72)
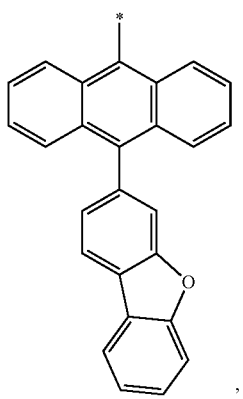 (H73)
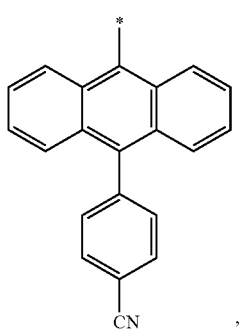 (H74)
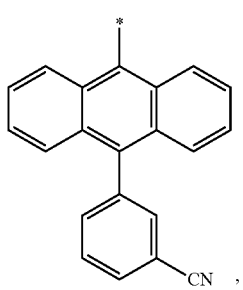 (H75)
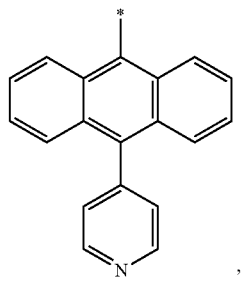 (H76)
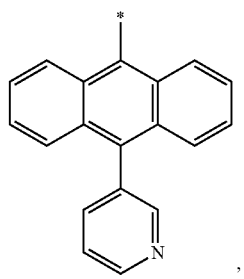 (H77)
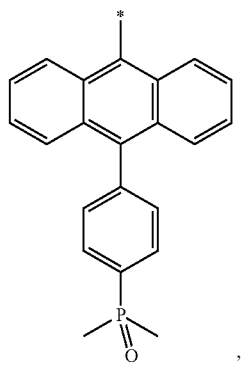 (H78)
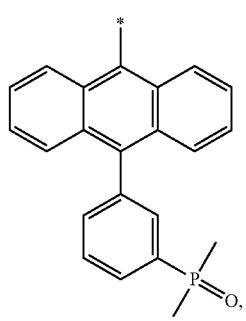 (H79)
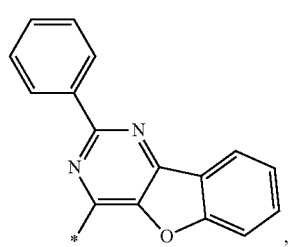 (H80)

-continued
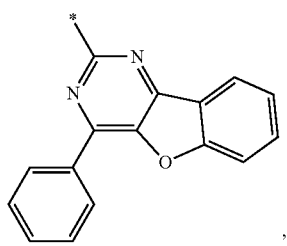
(H81)
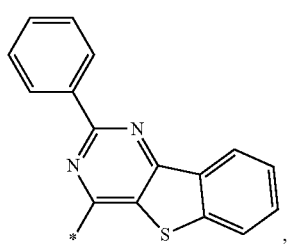
(H82)
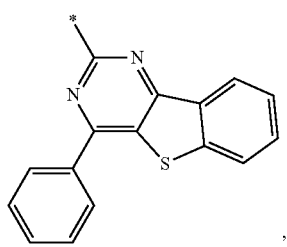
(H83)
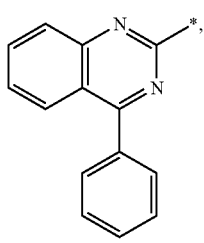
(H84)
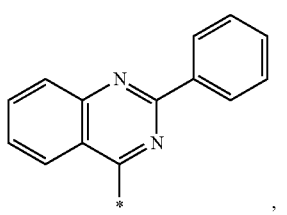
(H85)
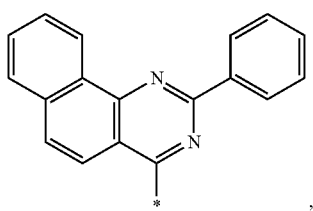
(H86)
-continued
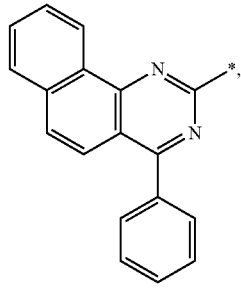
(H87)
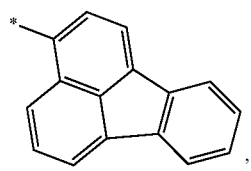
(H88)
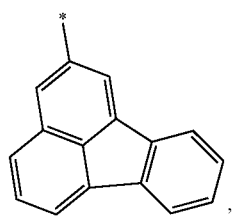
(H89)
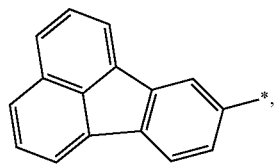
(H90)
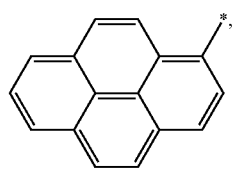
(H91)
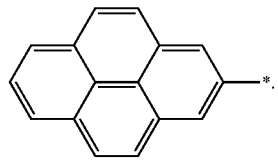
(H92)
15. A compound of any one of structures J1 to J37 or J39 to J53, or a salt thereof:

(J1)
(J2)
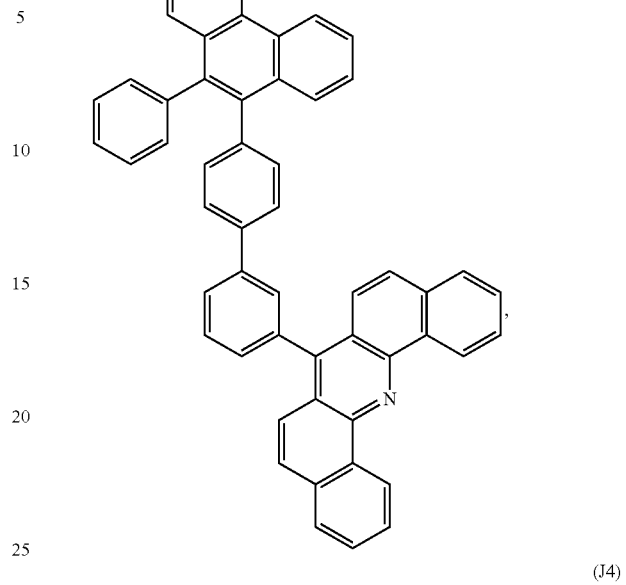
(J3)
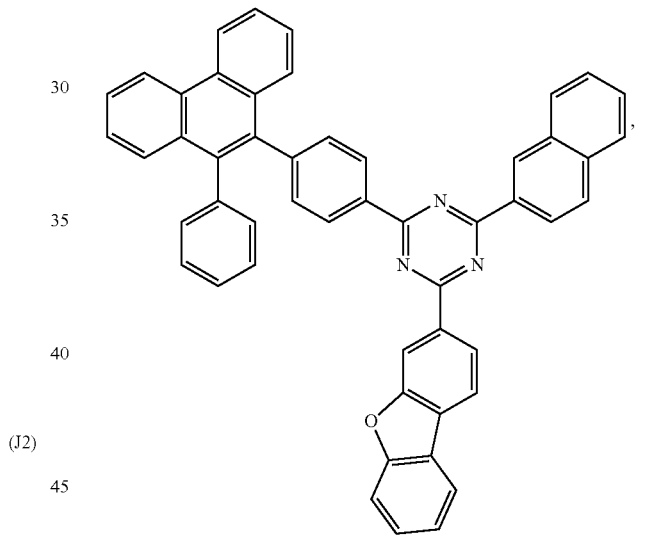
(J4)
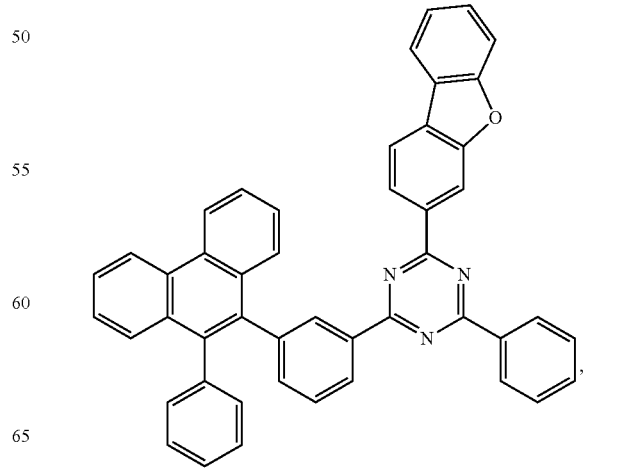
(J5)

(J6)
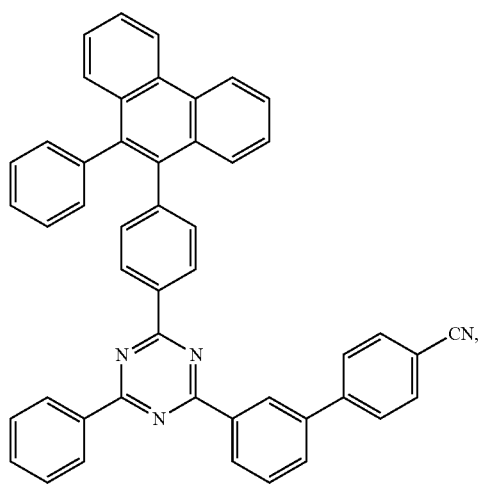
(J9)
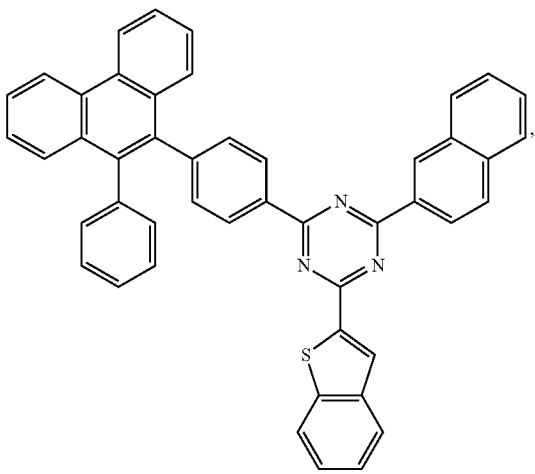
(J7)
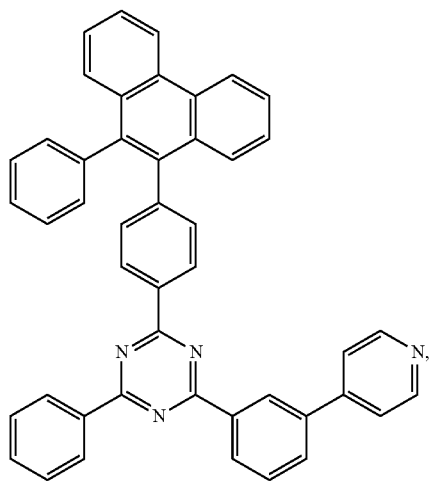
(J10)
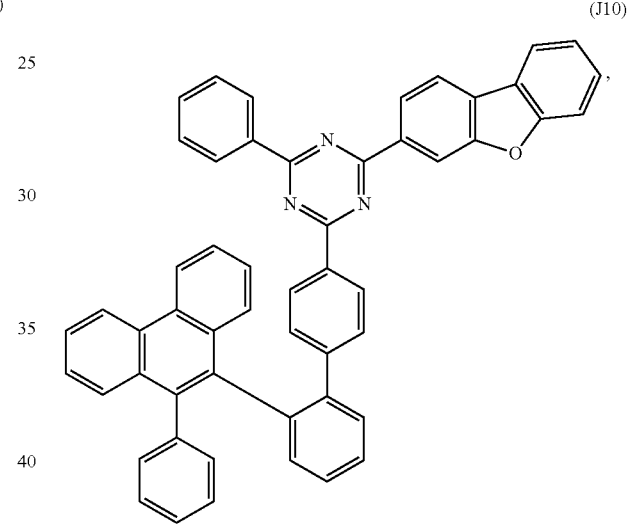
(J8)
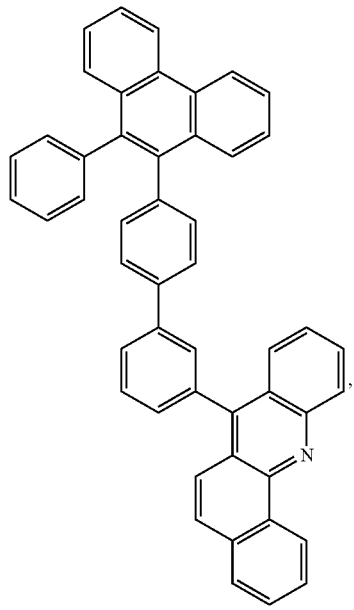
(J11)
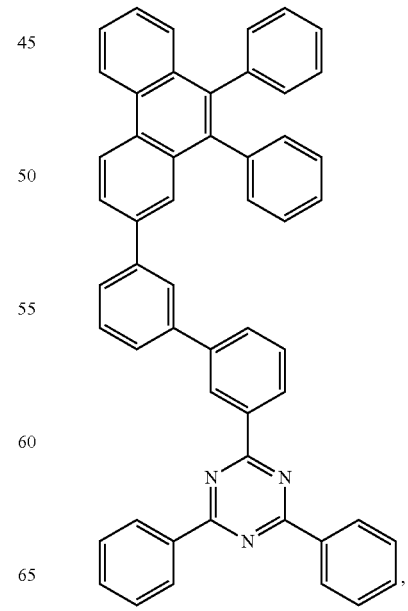

-continued
(J12)
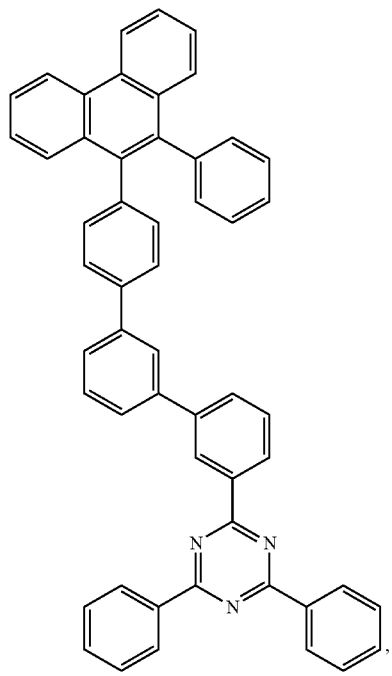
(J13)
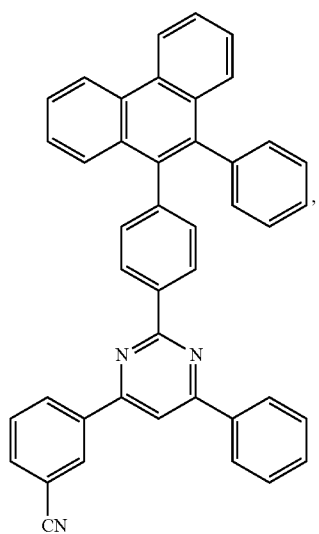
(J14)
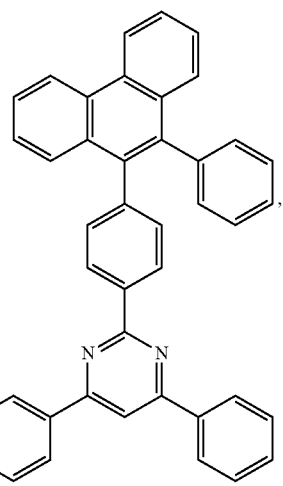
(J15)
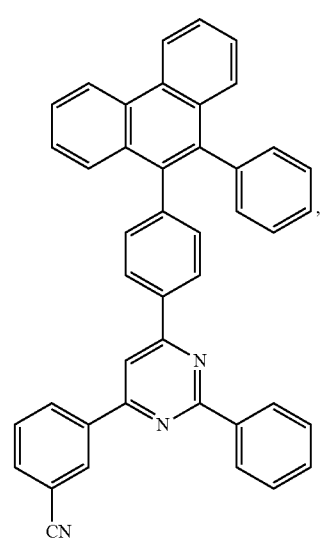
(J16)
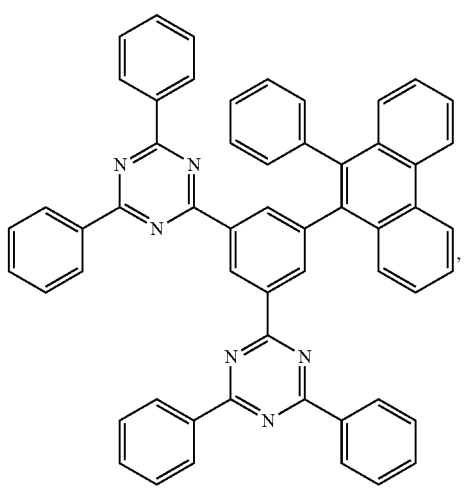

-continued
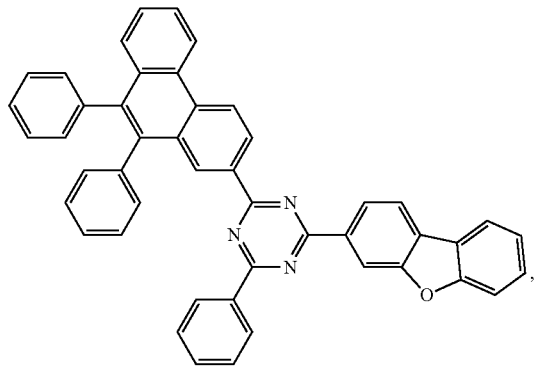
(J17)
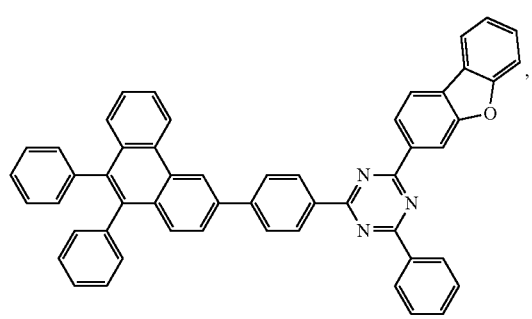
(J18)
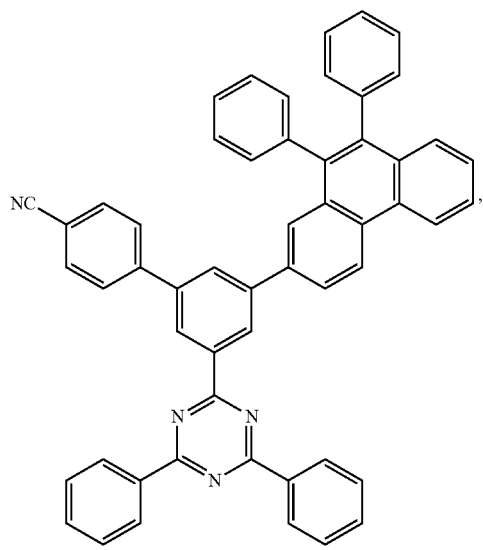
(J19)
-continued
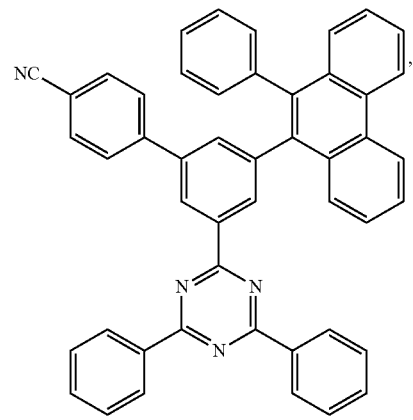
(J20)
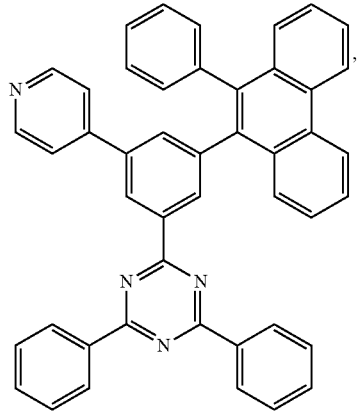
(J21)
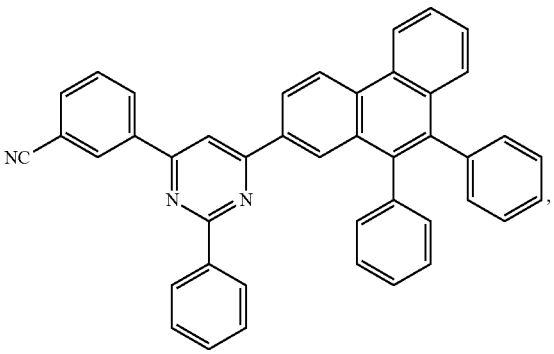
(J22)
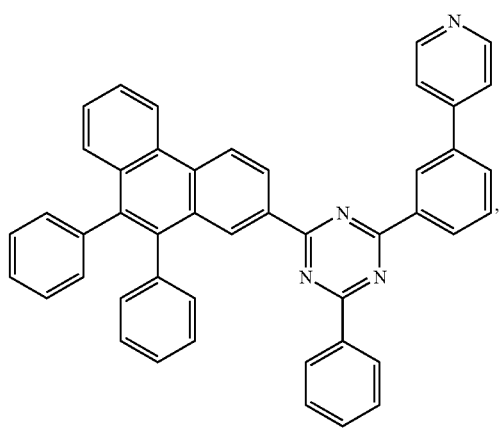
(J23)

(J24)
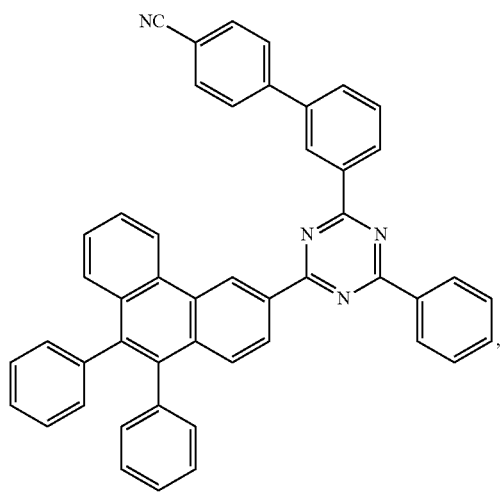
(J25)
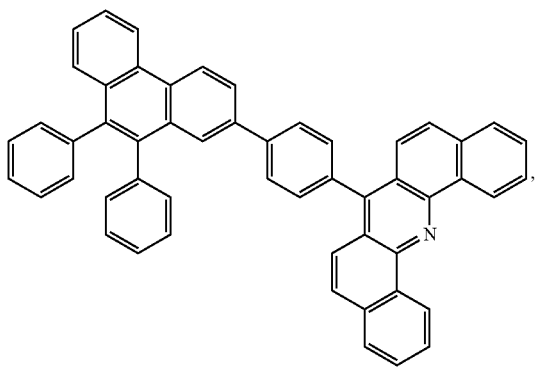
(J26)
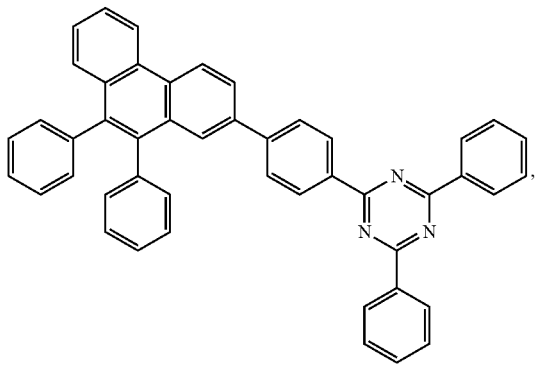
(J27)
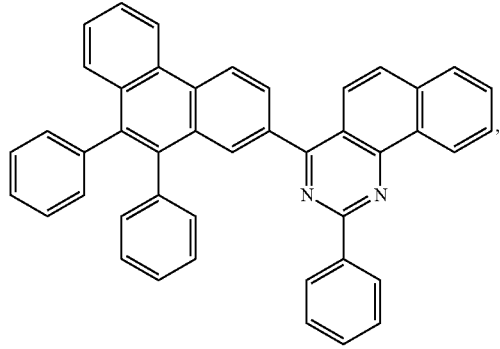
(J28)
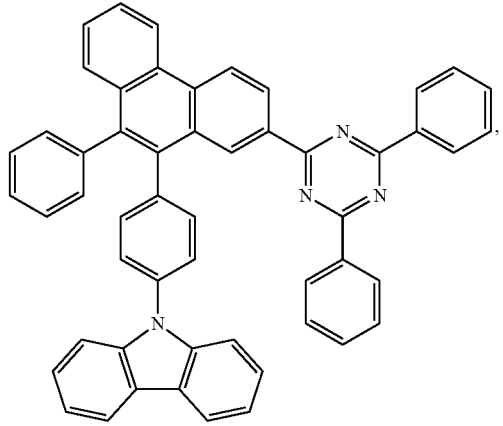
(J29)
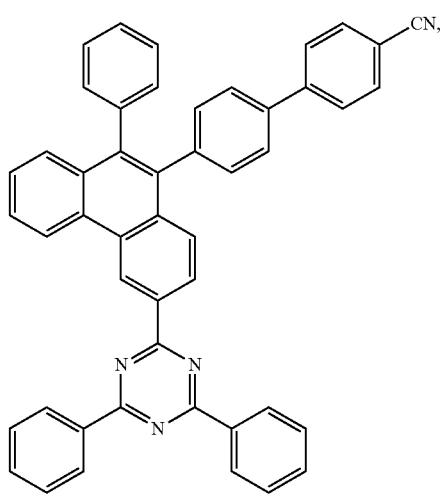
(J30)
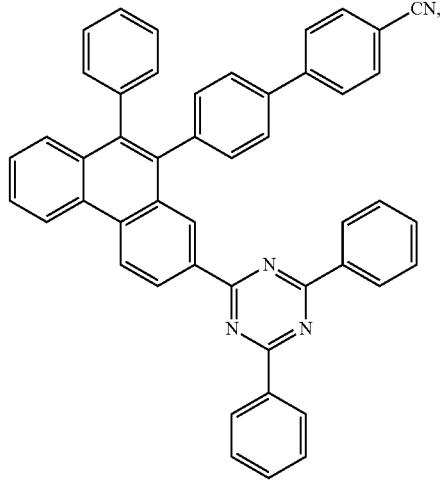

(J31)
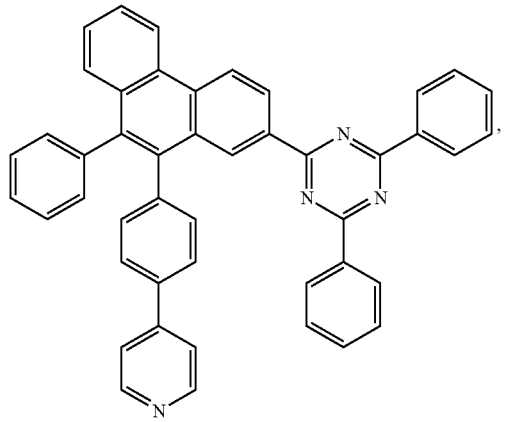
(J32)
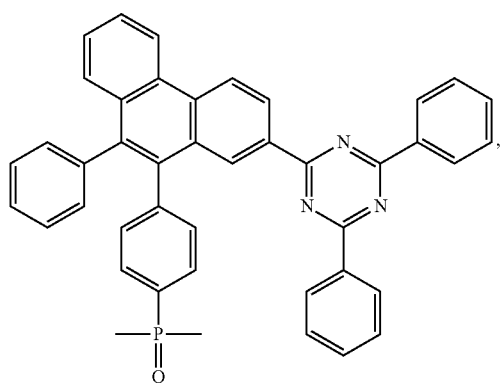
(J33)
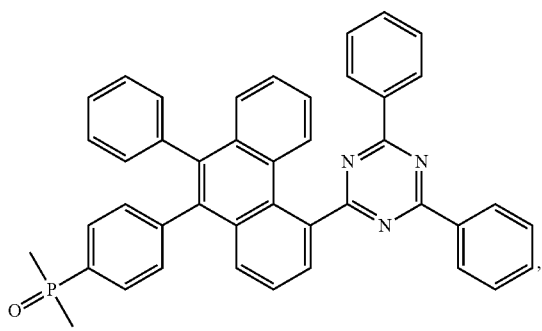
(J34)
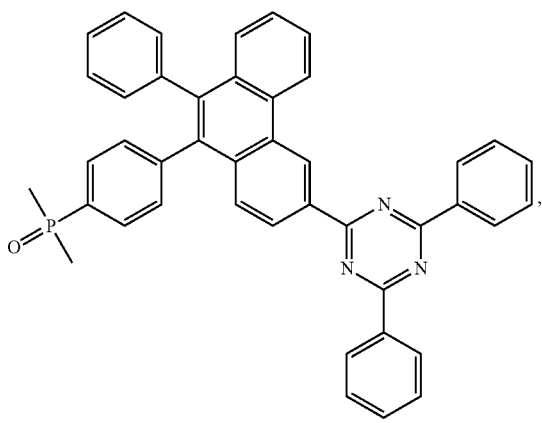
(J35)
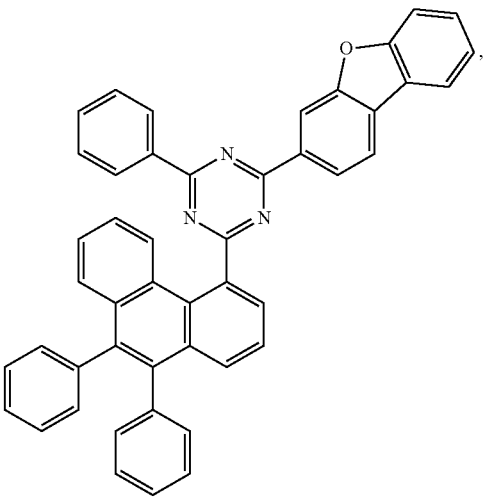
(J36)
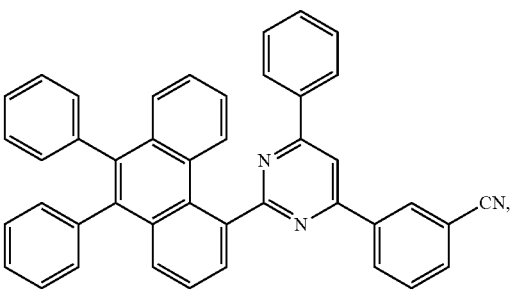
(J37)
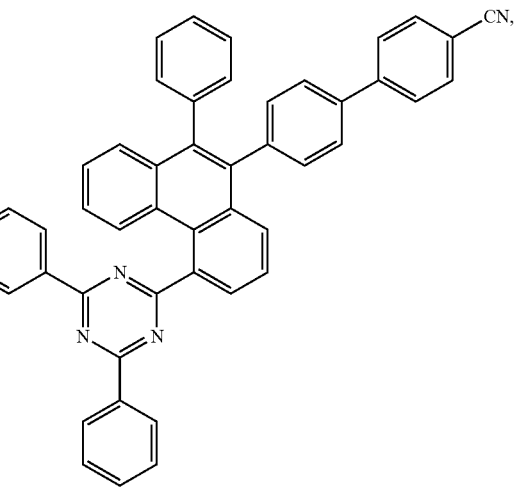
(J39)
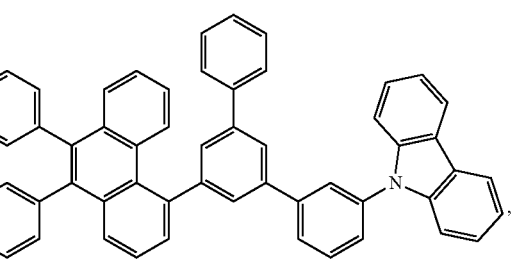

(J40)
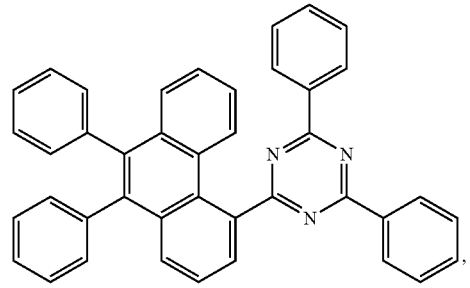
(J44)
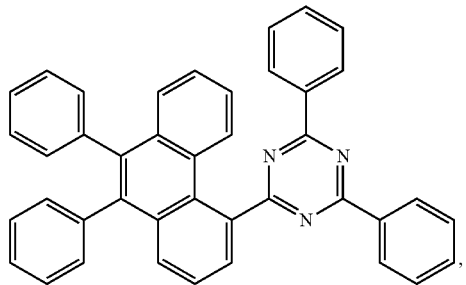
(J41)
(J45)
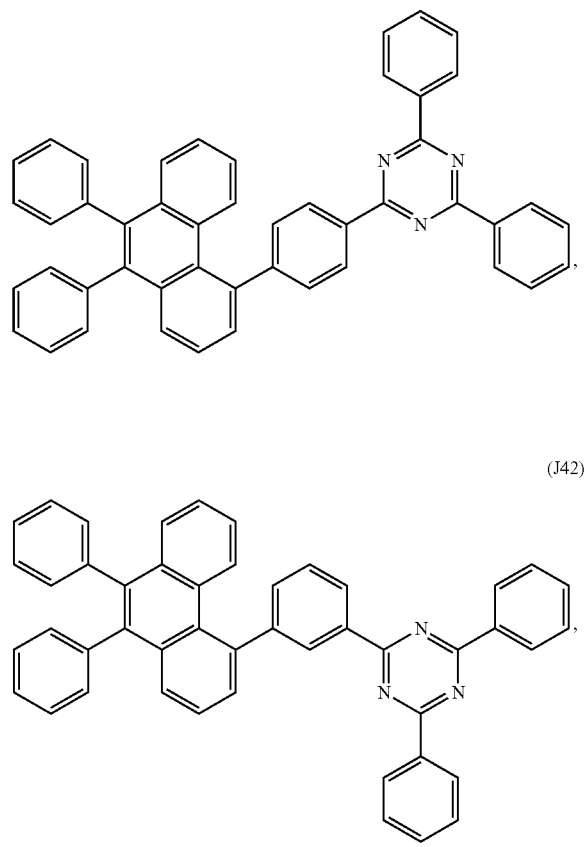
(J42)
(J43)
(J46)
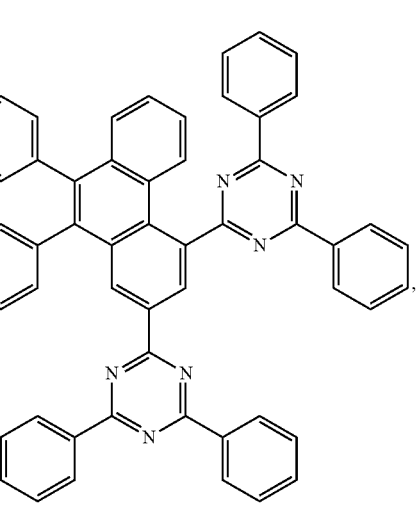

(J47) 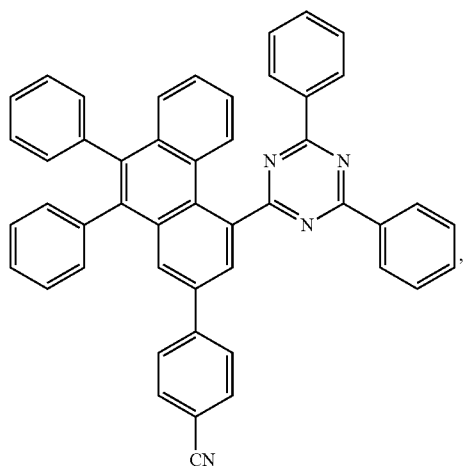
(J48) 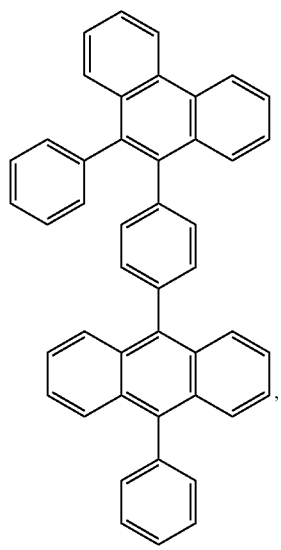
(J49) 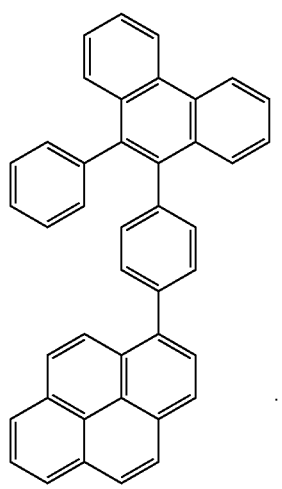
(J50) 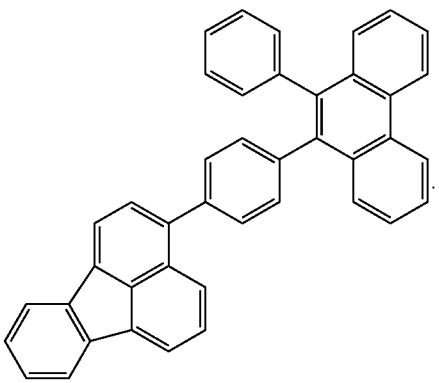
(J51) 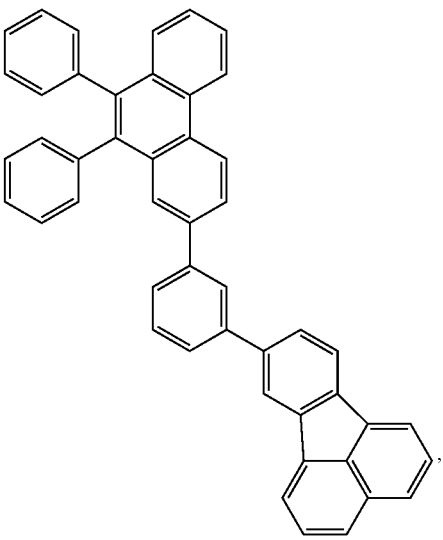
(J52) 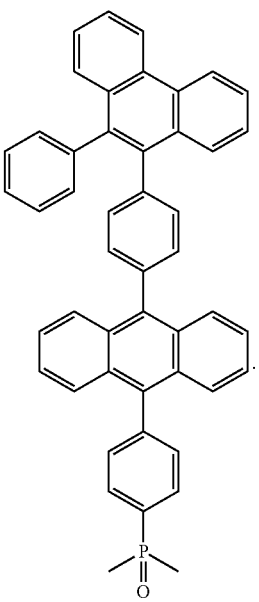

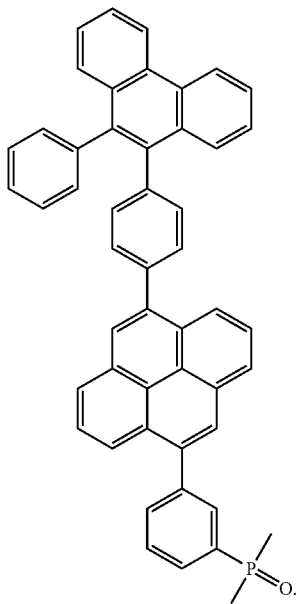

(J53)

16. An organic semiconductor layer comprising at least one compound of formula 1 according to claim 1.

17. The organic semiconductor layer according to claim 16, wherein the organic semiconductor layer further comprises a metal, metal salt or organic metal complex.

18. An organic electronic device comprising an anode layer, a cathode layer and at least one organic semiconductor layer according to claim 16.

19. An organic electronic device according to claim 18 further comprising at least one emission layer, wherein the organic semiconductor layer is arranged between the at least one emission layer and the cathode layer.

20. The organic electronic device according to claim 18, wherein the organic electronic device is selected from the group consisting of a light emitting device, thin film transistor, a battery, a display device and a photovoltaic cell.

21. The compound of formula 1 according to claim 1, wherein $R^1$, $R^2$, $R^3$ and $R^4$ are independently selected from hydrogen, substituted or unsubstituted $C_6$ to $C_{38}$ aryl, substituted or unsubstituted $C_3$ to $C_{36}$ heteroaryl, substituted or unsubstituted $C_1$ to $C_{16}$ alkyl group, —PO(R') 2, D, F, CN, or formula 2;

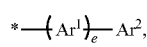

(2)

wherein the substituents are selected from $C_6$ to $C_{18}$ aryl, $C_3$ to $C_{25}$ heteroaryl, —PO(R')$_2$, D, F, CN, $C_1$ to $C_6$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

R' is independently selected from alkyl, aryl or heteroaryl;

a, b, c, d and e are independently 0, 1 or 2, wherein at least one of a, b, c and d is 1 or 2; wherein at least one of $R^1$, $R^2$, $R^3$ and $R^4$ is formula 2;

$Ar^1$ is selected from substituted or unsubstituted $C_6$ to $C_{38}$ arylene, substituted or unsubstituted $C_3$ to $C_6$ or $C_8$ to $C_{36}$ heteroarylene or substituted or unsubstituted $C_1$ to $C_{16}$ alkylene group, wherein the substituents are selected from $C_6$ to $C_{18}$ aryl, $C_3$ to $C_{25}$ heteroaryl, —PO(R')$_2$, D, F, CN, $C_1$ to $C_6$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

$Ar^2$ is selected from substituted or unsubstituted $C_6$ to $C_{38}$ aryl, substituted or unsubstituted $C_3$ to $C_6$ or $C_8$ to $C_{36}$ heteroaryl, or substituted or unsubstituted $C_1$ to $C_6$ alkyl group, wherein the substituents are selected from $C_6$ to $C_{18}$ aryl, $C_3$ to $C_{25}$ heteroaryl, —PO(R')$_2$, D, F, CN, $C_1$ to $C_{16}$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy;

wherein $Ar^1$ does not contain one or more CN substituents when $Ar^2$ is substituted or unsubstituted $C_6$ to $C_{38}$ aryl;

wherein the following compound 3 is excluded:

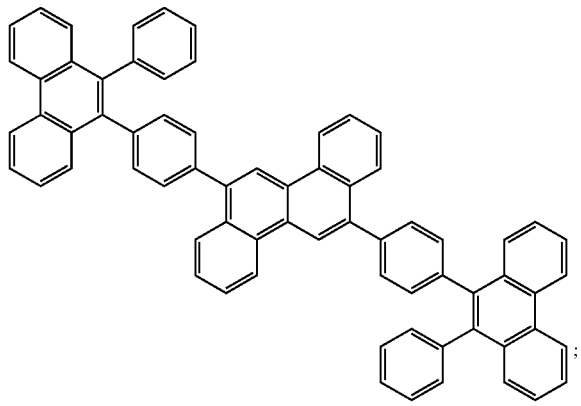

(3)

wherein, when present, $R^1$, $R^2$, or both $R^1$ and $R^2$, independently, (i) comprises a triazine moiety, or (ii) comprises a cyano substituent, or (iii) is formula 2 at the 1-, 2-, or 4-position of the 9,10-diphenylphenanthrene moiety of formula 1, wherein e is 1 or 2, or (iv) a combination thereof;

wherein, when present, $R^3$ (i) is not CN, (ii) is not an unsubstituted phenyl, (iii) is not an unsubstituted ethyl, (iv) is not a 4,6-diphenyl-1,3,5-triazin-2-yl, and (v) does not include a phenanthrenylene moiety; and wherein, when present, $R^4$ (i) is not CN, (ii) is not an unsubstituted phenyl, (iii) is not an unsubstituted ethyl, (iv) is not a 4,6-diphenyl-1,3,5-triazin-2-yl, and (v) (vi) does not include a phenanthrenylene moiety.

22. The compound of formula 1 according to claim 1, wherein the substituents on $R^1$, $R^2$, $R^3$, $R^4$, $Ar^1$ and $Ar^2$ are independently selected from $C_6$ to $C_{18}$ aryl, $C_3$ to $C_{25}$ heteroaryl, —PO(R')$_2$, D, F, CN, $C_1$ to $C_6$ alkyl, partially or perfluorinated $C_1$ to $C_{16}$ alkyl, partially or perdeuterated $C_1$ to $C_{16}$ alkyl, $C_1$ to $C_{16}$ alkoxy, partially or perfluorinated $C_1$ to $C_{16}$ alkoxy, or partially or perdeuterated $C_1$ to $C_{16}$ alkoxy.

23. The compound of formula 1 according to claim 1, wherein at least two of a, b, c and d are 0 or 1; or a and b are 0 and c or d is 1; or c and d are 0 and a or b is 1; or a and c are 0 and b or d is 1; or b and d are 0 and a or c is 1; or at least two of a, b, c and d is 1.

24. The compound of formula 1 according to claim 1, wherein e is selected from 0 or 1.

25. The compound of formula 1 according to claim 1, wherein $R^1$ and $R^2$ or $R^3$ and $R^4$ are selected same when a+b+c+d≥2.

26. The compound of formula 1 according to claim 1, wherein $R^1$ and $R^3$ or $R^2$ and $R^4$ are selected same when a+b+c+d≥2.

27. The organic semiconductor layer according to claim 16, wherein the organic semiconductor layer further comprises alkali borate.

28. A compound of the following structure or a salt thereof:

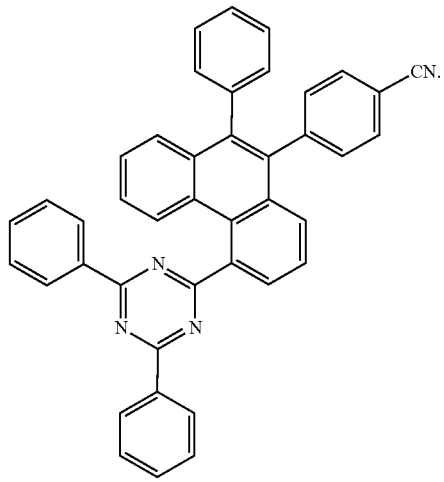

(J38)